(12) United States Patent
Horlow et al.

(10) Patent No.: US 11,898,151 B2
(45) Date of Patent: Feb. 13, 2024

(54) OBTAINING PLANTS HAVING IMPROVED BIOMASS DIGESTIBILITY

(71) Applicant: Institut National de Recherche Pour l'Agriculture, L'Alimentation et L'Environnement, Paris (FR)

(72) Inventors: Christine Horlow, Paris (FR); Marie-Hélène Durand-Tardif, Paris (FR); Gregory Mouille, Chartres (FR); Peter Rogowsky, Lyons (FR)

(73) Assignee: Institut National de Recherche Pour l'Agriculture, l'Alimentation et l'Environnement, Paris (FR)

( * ) Notice: Subject to any disclaimer, the term of this patent is extended or adjusted under 35 U.S.C. 154(b) by 172 days.

(21) Appl. No.: 17/427,992

(22) PCT Filed: Feb. 7, 2020

(86) PCT No.: PCT/EP2020/053140
§ 371 (c)(1),
(2) Date: Aug. 3, 2021

(87) PCT Pub. No.: WO2020/161306
PCT Pub. Date: Aug. 13, 2020

(65) Prior Publication Data
US 2022/0119835 A1    Apr. 21, 2022

(30) Foreign Application Priority Data
Feb. 8, 2019  (FR) ...................................... 1901260

(51) Int. Cl.
*C12N 15/82*  (2006.01)
*C12N 15/01*  (2006.01)

(52) U.S. Cl.
CPC ......... *C12N 15/8255* (2013.01); *C12N 15/01* (2013.01)

(58) Field of Classification Search
None
See application file for complete search history.

(56) References Cited

FOREIGN PATENT DOCUMENTS

| WO | 2007/065878 A2 | 6/2007 |
| WO | 2007/085483 A1 | 8/2007 |

OTHER PUBLICATIONS

International Search Report issued in corresponding International Patent Application No. PCT/EP2020/053140 dated Mar. 18, 2020.
Ramirez et al., "Growth- and stress-related defects associated with wall hypoacetylation are strigolactone-dependent," Plant Direct, 2: 1-11 (2018).
Yuan et al., "The *Arabidopsis* DUF231 Domain-Containing Protein ESK1 Mediates 2-O- and 3-O-Acetylation of Xylosyl Residues in Xylan," Plant & Cell Physiology, 54 (7): 1186-1199 (2013).
Xiong et al., "Xylan O-Acetylation Impacts Xylem Development and Enzymatic Recalcitrance as Indicated by the *Arabidopsis* Mutant tbl29," Molecular Plant, 6 (4): 1373-1375 (2013).
Bensussan et al., "Suppression of Dwarf and irregular xylem Phenotypes Generates Low-Acetylated Biomass Lines in *Arabidopsis*," Plant Physiology, 168: 452-463 (2015).

*Primary Examiner* — Brent T Page
(74) *Attorney, Agent, or Firm* — Morgan, Lewis & Bockius LLP

(57) ABSTRACT

The present invention relates to a plant obtained by mutagenesis, such that the expression and/or the activity of the ESK1 protein and the expression and/or the activity of the TPS7 protein are diminished compared to a non-mutagenated plant. Said plant with biomass that has better digestibility maintains satisfactory growth. A further aim of the present invention is a method for preparing said plant, as well as the use of said plant for the production of biofuel.

9 Claims, 15 Drawing Sheets
Specification includes a Sequence Listing.

```
                                                                    640
ESK3_Zm00001d022582_T01 (450) GCCGC----CGCCTCCTCCCAGTTGCGG----GTGCGACCTGTACCGGGGG GCAGACGTGCGACCTGTACCGGGG ESK6-CR2#
ESK6_Zm00001d028751_FG003 (532) GCCGGCGCTGCCGGGTGGTGAGCGTGAGACGTGCCAGAACGTGCCGACCTGTACCGGGACGTGGGCAGCTGGT TGCCGG----GTGCGACCTGTACCGGGT ESK3-CR8#
                                                                                                                            720
                          641                                CCAGGTTGCGG GTGCGACCTGT
                                                                                      GTGCGACCTGTGGACCGGGT CGGTGGGGTCGGTGGACGTTGACGCGGGCGA
                                                                                                           CCAGAACGTGCCGACCTGTACCGGGACGTGGGCAGCTGGGTGTACGACGAGT--GA
```

Figure 7

Figure 8:
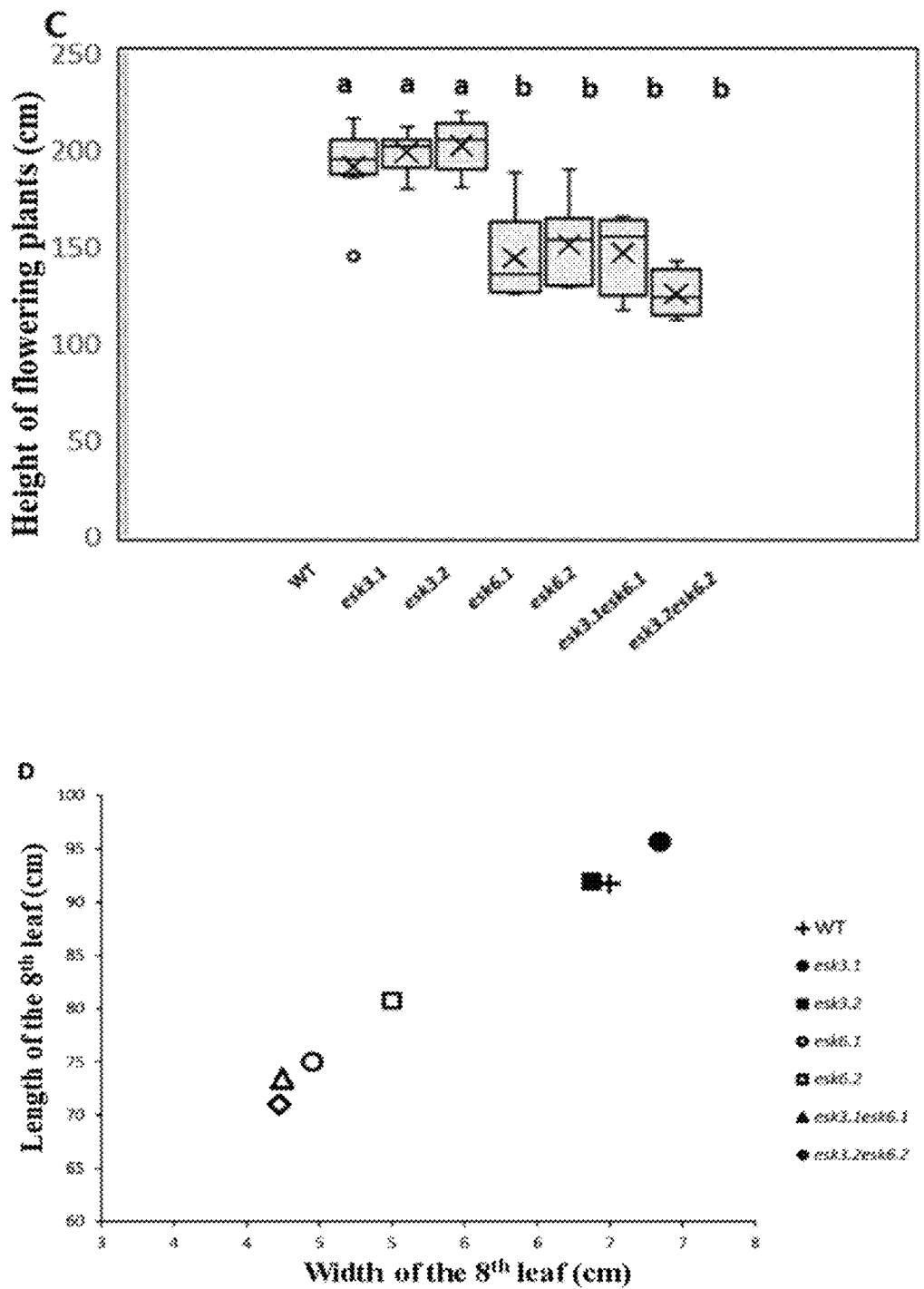

A
B
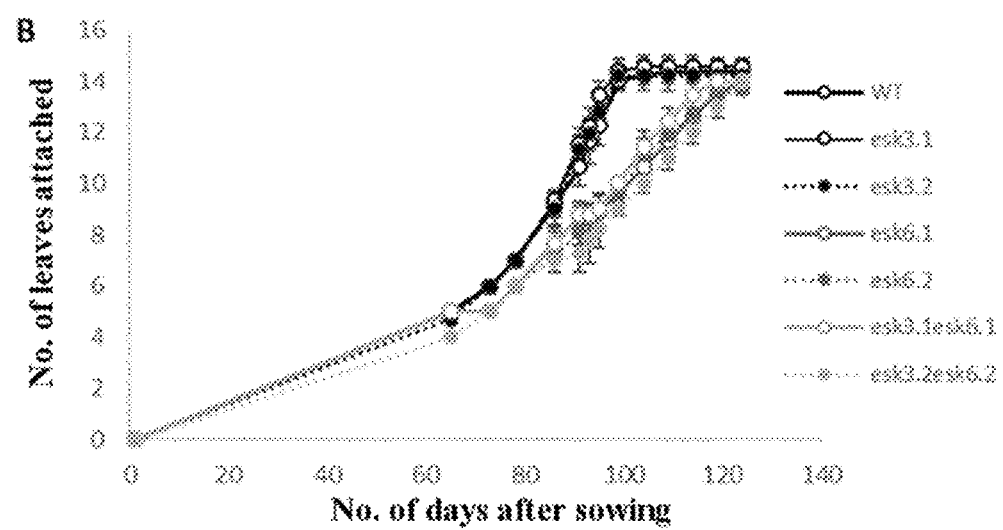
Figure 8

B

| Genotypes | Lignin Klason in %RP | Std Error |
|---|---|---|
| WT | 13,90 | 0,47 |
| esk3.1 | 14,31 | 0,40 |
| esk3.2 | 14,99 | 0,50 |
| esk6.1 | 14,42 | 0,34 |
| esk6.2 | 13,87 | 0,43 |
| esk3.1esk6.1 | 14,67 | 0,65 |
| esk3.2esk6.2 | 14,26 | 0,20 |

C

OBTAINING PLANTS HAVING IMPROVED BIOMASS DIGESTIBILITY

SEQUENCE LISTING SUBMISSION VIA EFS-WEB

A computer readable text file, entitled "SequenceListing.txt," created on Jul. 15, 2021 with a file size of 195,753 bytes contains the sequence listing for this application and is hereby incorporated by reference in its entirety.

The present invention relates to the field of the plant biomass production.

In particular, it relates to the preparation of plants that have a biomass having an improved digestibility (a property also referred to as degradability) and that conserve a satisfactory growth.

The fossil fuels such as oil, coal and gas are still the main source of energy for all sectors. In the field of the transport, the oil still predominates. However, these hydrocarbons are very polluting for the environment, in particular in that they release a lot of $CO_2$ during their combustion, a carbon stock that was previously buried. In addition, the deposits are becoming increasingly scarce and the extraction is becoming more and more expensive (https://www.planete-energies-.com/fr/medias/decryptages/les-energies-fossiles).

The biofuels could be part of the answer to oil reserves dwindling. The first generation biofuels are derived from simple sugars and oils present in the plants, which are transformed into ethanol and bio-ester. The second generation biofuels (Sims et al., 2010) are produced from lignocellulosic biomass; this biomass consists of all of the cell walls of the plants. The advantage of these second generation biofuels is that their production does not compete with the human food. The lignocellulosic biomass used for the second generation biofuels can be extracted from the crop residues such as those of the corn.

The cost of producing biofuel from this lignocellulosic biomass is still relatively high, although the raw material is cheap. In addition, the biomass used as fodder for the domestic animals does not have an optimal digestibility.

Within the plants, some tissues are richer than others in lignocellulosic biomass. This is in particular true for the tissues of the xylem, which are essentially composed of vessels that conduct raw sap and fibres. The xylem is a carbon sink; the simple sugars produced by the photosynthesis are stored in the xylem in the form of bio-polymers constituting the xylem wall.

The plant polymers are complex and bound together, which makes them difficult to digest by the animals or to their exploitation in the chemical industry, laborious and relatively polluting.

Furthermore, the exploitation of the lignocellulosic biomass is a method that requires a first pre-treatment step aimed at "breaking" the cellulose/hemicellulose/lignin matrix that forms the structure of the secondary lignified walls, which are composed of a complex tangle of cellulose fibrils embedded in a lignin and hemicellulose matrix. This dense mesh can therefore hinder the access of the digestive enzymes to the polysaccharides of interest such as the cellulose, a hexose polymer, or the hemicelluloses, such as the xylan, a pentose polymer.

Obtaining more easily digestible plant lines with an identical size and growth to their wild type equivalent is thus a current issue (Kalluri et al., 2014). Among the strategies implemented to achieve this, there are strategies to reduce the lignin content or the modification of their chemical structure (decorations, bonding to the other polymers), which leads to defects of vigour incompatible with their cultivation (Mottiar et al., 2016). Other strategies, in particular those tested and inventoried by Bhatia and colleagues (Bhatia et al., 2017) consist of the modification of the bonding between the polymers as well as the modification of the decorations of the hemicelluloses.

Previous work has led to identify *Arabidopsis thaliana* mutants that are tolerant to freezing without a prior acclimation period, named eskimo 1 (esk1) (Xin et al., 1998). Plants having the mutated esk1 gene were then characterized by their insensitivity to water stress (Bouchabke-Coussa et al., 2008), their dwarf phenotype (Lefebvre et al., 2011) as well as a low level of acetylation of the xylans (Yuan et al., 2013).

This low acetylation of the xylans observed in the esk1 mutant leads to a better enzymatic digestibility of the walls (Bensussan et al., 2015), which represents a valuable advantage for the transformation of the plants of agronomic interest, in particular for the production of biofuels or for the animal feed.

However, even under optimal cultivation conditions, this mutant is characterized in particular by a dwarf phenotype and the plants carrying the esk1 mutation produce very little biomass, which considerably limits their interest for the production, whether for the animal feed or the biofuel production.

In this context, further studies focused on the identification of new lines having a good degradability of their wall but having an improved growth; these studies led to the identification of a double mutant (kak and esk1-5 genes) that conserve a low level of acetylation of the xylans but in which the dwarf phenotype is suppressed (Bensussan et al., 2015).

The inventors have now identified a new mutation which, in combination with the mutation of the esk1 gene, leads to a line that conserve a low level of acetylation of the xylans and has an improved biomass production (suppression of the dwarf phenotype).

More specifically, they identified the tps7 gene as a gene responsible for the suppression of the phenotype of the dwarfism in the esk1 mutants. They then highlight that the *Arabidopsis thaliana* plants carrying the mutations in the esk1 and tps7 genes had a digestibility of the biomass improved compared to the wild *Arabidopsis thaliana* plants. In addition, they also highlight that the esk1, tps7 and kak triple mutant *Arabidopsis thaliana* plants and the esk1, tps7 and tps6 triple mutant *Arabidopsis thaliana* plants also have a better digestibility of the biomass compared to the wild *Arabidopsis thaliana* plants.

In *Arabidopsis*, there are 21 putative genes of biosynthesis of the trehalose distributed into three classes according to their homology with the ScTPS1 and ScTPS2 yeast genes (Ramon et al., 2009). The class 1 and 2 genes encode bipartite proteins, the TPS (trehalose-6-phosphate synthase) domain and the TPP (trehalose-6-phosphate phosphatase) domain. Thus, the trehalose-6-phosphate (T6P), a precursor of the trehalose, is produced from glucose-UDP and glucose-9-phosphate, thanks to the TPS enzyme. Then the T6P is further metabolized to trehalose by the TPP enzyme (Lunn et al., 2014, O'Hara et al., 2013; Vandesteene et al., 2012). The tps7 gene, which encodes a trehalose-6-phosphate synthase 7 (TPS7), belongs to the class 2 of the putative genes of biosynthesis of the trehalose.

Thus the present invention relates to a plant obtained by mutagenesis such as:
the expression and/or the activity of the protein designated ESK1, and the expression and/or the activity of the protein designated TPS7, are decreased, as compared to a non-mutagenized parent plant, and the decrease in the expression and/or the activity of the ESK1 and TPS7 proteins having been achieved by at least one mutation in each of the genes encoding the ESK1 and TPS7 proteins, and such that:

the non-mutagenized ESK1 protein has at least 50% identity with the sequence SEQ ID NO: 1 and comprising the acyl esterase and transmembrane domains, and the non-mutagenized TPS7 protein has at least 60% identity with the sequence SEQ ID NO: 2 and comprising the TPS and TPP domains.

The person skilled in the art is familiar with the approach to be taken for obtaining the best ortholog in a species of interest, and this via the "PLAZA" tool described in Example 2, via the "PANTHER" tool (Mi et al., 2017), described below or via phylogenetic analyses, such as those conducted by Paul et al., 2018.

The first step using the "PANTHER" tool consists in entering the identity of the gene (gene ID) on the TAIR website (http://www.*arabidopsis*.org). The second step consists in selecting "gene and orthologs" on the PANTHER website (http://www.pantherdb.org/), then entering the gene ID and pressing "search". Among the proposed orthologs, the LOD "least ortholog divergent" must be chosen; they correspond to the best orthologs of a given protein.

The non-mutagenized ESK1 protein as defined in the present invention has at least 50% identity with the sequence SEQ ID NO: 1 and in ascending order of preference at least 55%, 60%, 65%, 70%, 75%, 80%, 85%, 90%, 95%, 97%, 98% and 99% identity.

The non-mutagenized TPS7 protein as defined in the present invention has at least 60% identity with the sequence SEQ ID NO: 2 and in ascending order of preference at least 65%, 70%, 75%, 80%, 85%, 90%, 95%, 97%, 98% and 99% identity.

The present invention is applicable to all the monocotyledon or dicotyledon plants. In a non-limiting way, it can be applied to the cereal plants, the ornamental plants, the fruit trees and the non-fruit trees.

The best ortholog for each of the ESK1 and TPS7 proteins in the plants of interest listed above is found via the PLAZA tool or via the PANTHER tool. The best orthologs for the ESK1 and TPS7 proteins in the corn are as follows: ZmESK1 (Zm00001d028751) and ZmTRPS7 (Zm00001d043469).

The plant according to the invention may be a dicotyledon plant such as *Arabidopsis thaliana*, the poplar (*Populus trichocarpa*) or the vine (*Vitis vinifera*). Preferably, the plant according to the invention is a monocotyledon such as the wheat, the corn (*Zea mays*), the *sorghum* (*Sorghum bicolor*) or the rice (*Oryza sativa*), even more preferably the corn.

The protein designated ESK1, also referred to as TBL29, whose the expression and/or the activity is decreased in the plant according to the invention is defined with reference to the *Arabidopsis thaliana* ESK1 protein of SEQ ID NO: 1; indeed, depending on the plant species considered, the person skilled in the art is able to identify the ortholog of the protein designated ESK1 which comprises:

an acyl-esterase domain, required for their enzymatic activity (Anantharaman et al., 2010 and Gille et al., 2012), comprising the conserved pattern GDSL of sequence SEQ ID NO: 4 and the conserved pattern of sequence SEQ ID NO: 5, located at positions corresponding respectively to the positions 214-217 and 462-465 of the sequence SEQ ID NO: 1, when said ESK1 protein is aligned with said sequence SEQ ID NO: 1, and a transmembrane domain in $NH_2$, allowing an anchoring to the inner membrane of the Golgi apparatus, the likely site of the acetylation of the xylans (Gille et al., 2012 and Yuan et al., 2013). The presence of the transmembrane domain is identified via the TMHMM bioinformatics tool, which is a software for predicting the structure of the membrane proteins.

The conserved pattern GDSL stands for the chain of the glycine, aspartate, serine and leucine amino acids.

A conserved domain or pattern is defined as a chain of amino acids that is identical in the orthologous proteins.

According to a particular embodiment of the invention, the ESK1 protein may be further defined by 3 additional conserved patterns of sequences:

SEQ ID NO: 6 located at positions corresponding to the positions 211-224 of the sequence SEQ ID NO: 1, when said ESK1 protein is aligned with said sequence SEQ ID NO: 1 and which comprises the conserved pattern GDSL, of sequence SEQ ID NO: 4, RKD located at positions corresponding to the positions 433-435 of the sequence SEQ ID NO: 1, when said ESK1 protein is aligned with said sequence SEQ ID NO: 1, and SEQ ID NO: 7 located at positions corresponding to the positions 461-470 of the sequence SEQ ID NO: 1, when said ESK1 protein is aligned with said sequence SEQ ID NO: 1 and which comprises the conserved pattern of sequence SEQ ID NO: 5.

The conserved pattern RKD stands for the chain of the arginine, lysine and aspartate amino acids.

For example, the ESK1 proteins are derived from *Arabidopsis thaliana* of sequence SEQ ID NO: 1 (ESK1/TBL29), of *Zea mays* (ZmESK1, designated Zm00001d028751) of sequence SEQ ID NO: 8, of *Oryza sativa* (designated Os03g0291800) of sequence SEQ ID NO: 9, of *Populus trichocarpa* (designated POTR_0010s19490) of sequence SEQ ID NO: 10 or of *Sorghum bicolor* (designated Sb01g038450.1) of sequence SEQ ID NO: 11.

According to an embodiment of the present invention, the plant according to the invention is a dicotyledon and said ESK1 protein has at least 65% identity with SEQ ID NO: 1 and in ascending order of preference at least 70%, 75%, 80%, 85%, 90%, 95%, 97%, 98% and 99% identity with SEQ ID NO: 1 and comprises the conserved patterns of sequences GDSL, of sequence SEQ ID NO: 4 and SEQ ID NO: 5 located at positions corresponding respectively to the positions 214-217 and 462-465 of the sequence SEQ ID NO: 1, when said ESK1 protein is aligned with said sequence SEQ ID NO: 1.

According to another embodiment of the present invention, the plant according to the invention is a monocotyledon and said ESK1 protein has at least 50% identity with SEQ ID NO: 1 and in ascending order of preference at least 55%, 60%, 65%, 70%, 75%, 80%, 85%, 90%, 95%, 97%, 98% and 99% identity with SEQ ID NO: 1 and comprises the conserved domains of sequences GDSL, of sequence SEQ ID NO: 4 and SEQ ID NO: 5 located at positions corresponding respectively to the positions 214-217 and 462-465 of the sequence SEQ ID NO: 1, and may also comprise at least one of the conserved domains of sequences SEQ ID NO: 6, RKD and SEQ ID NO: 7 located at positions corresponding respectively to the positions 211-224, 433-435 and 461-470 of the sequence SEQ ID NO: 1, when said ESK1 protein is aligned with said sequence SEQ ID NO: 1.

The protein designated TPS7 whose the expression and/or the activity is decreased in the plant according to the invention is defined with reference to the *Arabidopsis thaliana* TPS7 protein of SEQ ID NO: 2; indeed, depending on the plant species considered, the person skilled in the art is able to identify the ortholog of the protein designated TPS7 as follows which has:

- a TPS domain (Yang et al., 2012), comprising the conserved pattern of sequence SEQ ID NO: 12 and the conserved pattern of sequence SEQ ID NO: 13, located at positions corresponding respectively to the positions 203-207 and 226-236 of the sequence SEQ ID NO: 2, when said TPS7 protein is aligned with said sequence SEQ ID NO: 2, and
- a TPP domain (Yang et al., 2012), comprising the conserved patterns of sequence SEQID NO: 14, 15 and 16, located at positions corresponding respectively to the positions 649-654, 777-787 and 807-815 of the sequence SEQ ID NO: 2, when said TPS7 protein is aligned with said sequence SEQ ID NO: 2.

For example, the TPS7 proteins are derived from *Arabidopsis thaliana* of sequence SEQ ID NO: 2 (AtTPS7), from *Zea mays* (Zmtrps7, designated Zm00001d043469) of sequence SEQ ID NO: 17, from *Oryza sativa* (designated Os01g0749400) of sequence SEQ ID NO: 18, from *Vitis vinifera* (designated VIT_12s0028g01670) of sequence SEQ ID NO: 19, from *Populus trichocarpa* (designated POPTR_0011G70900) of sequence SEQ ID NO: 20, or from *Sorghum bicolor* (designated SB03G034640) of sequence SEQ ID NO: 21.

According to an embodiment of the present invention, the plant according to the invention is a dicotyledon and said TPS7 protein has at least 70% identity with SEQ ID NO: 2 and in ascending order of preference at least 75%, 80%, 85%, 90%, 95%, 97%, 98% and 99% identity with SEQ ID NO: 2 and comprises the conserved patterns of sequences SEQ ID NO: 12 and SEQ ID NO: 13 located at positions corresponding respectively to the positions 203-207 and 226-236 of the sequence SEQ ID NO: 2, when said TPS7 protein is aligned with said sequence SEQ ID NO: 2.

According to another embodiment of the present invention, the plant according to the invention is a monocotyledon and said TPS7 protein has at least 60% identity with SEQ ID NO: 2 and in ascending order of preference at least 65%, 70%, 75%, 80%, 85%, 90%, 95%, 97%, 98% and 99% identity with SEQ ID NO: 2 and comprises the conserved patterns of sequences SEQ ID NO: 12 and SEQ ID NO: 13 located at positions corresponding respectively to the positions 203-207 and 226-236 of the sequence SEQ ID NO: 2, and may also comprise at least one of the conserved patterns of sequences SEQ ID NO: 14, 15 and 16 located at positions corresponding respectively to the positions 649-654, 777-787 and 807-815 of the sequence SEQ ID NO: 2, when said TPS7 protein is aligned with said sequence SEQ ID NO: 2.

According to a first particular embodiment, the plant according to the invention such that the expression and/or the activity of the ESK1 and TPS7 proteins are decreased is further such that the expression and/or the activity of the protein designated KAK is decreased, as compared to a non-mutagenized parent plant, the decrease in the expression and/or the activity of the KAK protein having been achieved by at least one mutation in the gene encoding the KAK protein, and such that the non-mutagenized KAK protein has at least 60% identity with the sequence SEQ ID NO: 3 and comprising the armadillo replicates and a HECT domain.

The non-mutagenized KAK protein as defined in the present invention has at least 60% identity with the sequence SEQ ID NO: 3 and in ascending order of preference at least 65%, 70%, 75%, 80%, 85%, 90%, 95%, 97%, 98% and 99% identity.

The best ortholog for the KAK protein in the plants of interest listed above is found via the PLAZA tool or via the PANTHER tool. The best ortholog for the KAK protein in the corn is ZmKAK1.

The KAK protein whose the expression and/or the activity is decreased in the plant according to the invention is defined with reference to the *Arabidopsis thaliana* KAK protein of SEQ ID NO: 3; indeed, depending on the plant species considered, the person skilled in the art is able to identify the ortholog of the protein designated KAK as follows which has:

- armadillo replicates in $NH_2$, defined as a bonding domain to the target proteins, which will be addressed to the proteasome (Sharma et al., 2016) comprising the conserved patterns of sequences SEQ ID NO: 22 and 23, located at positions corresponding to the positions 291-309 and 311-341 of the sequence SEQ ID NO: 3, when said KAK protein is aligned with said sequence SEQ ID NO: 3, and
- a HECT domain in COOH, bonding ubiquitin units that will subsequently be bound to the targets for the addressing to the proteasome (El Refy et al., 2003), comprising the conserved pattern of sequence SEQ ID NO: 24, located at positions corresponding to the position 1845-1867 of the sequence SEQ ID NO: 3, when said KAK protein is aligned with said sequence SEQ ID NO: 3.

The presence of the armadillo replicates and the HECT domain is identified via the "Protein Sequence Analysis and Classification" bioinformatics tool from InterPro 68.0 (EMBL-EBI), found using the website https://www.ebi.ac.uk/interpro/.

According to a particular embodiment of the invention, the KAK protein may be further defined by 2 additional conserved patterns of sequences:

- SEQ ID NO: 25 located at positions corresponding to the positions 1466-1490 of the sequence SEQ ID NO: 3, when said KAK protein is aligned with said sequence SEQ ID NO: 3, and
- SEQ ID NO: 26 located at positions corresponding to the positions 1496-1521 of the sequence SEQ ID NO: 3, when said KAK protein is aligned with said sequence SEQ ID NO: 3.

For example, the KAK proteins are derived from *Arabidopsis thaliana* of sequence SEQ ID NO: 3 (AtKAK), from *Zea mays* (ZmUPL3, also designated ZmKAK1 and Zm00001d004139) of sequence SEQ ID NO: 27, from *Vitis vinifera* (designated VIT_03s0038g02340) of sequence SEQ ID NO: 28, from *Populus trichocarpa* (designated POPTR_0009s13670) of sequence SEQ ID NO: 29, or from *Sorghum bicolor* (designated Sb06g003290.1) of sequence SEQ ID NO: 30.

According to an embodiment of the present invention, the plant according to the invention is a dicotyledon and said KAK protein has at least 70% identity with SEQ ID NO: 3 and in ascending order of preference at least 75%, 80%, 85%, 90%, 95%, 97%, 98% and 99% identity with SEQ ID NO: 3 and comprises the conserved patterns of sequences SEQ ID NO: 22, 23 and 24 located at positions corresponding respectively to the positions 291-309, 311-341 and 1845-1867 of the sequence SEQ ID NO: 3, when said KAK protein is aligned with said sequence SEQ ID NO: 3.

According to another embodiment of the present invention, the plant according to the invention is a monocotyledon and said KAK protein has at least 60% identity with SEQ ID NO: 3 and in ascending order of preference at least 65%, 70%, 75%, 80%, 85%, 90%, 95%, 97%, 98% and 99% identity with SEQ ID NO: 3 and comprises the conserved patterns of sequences SEQ ID NO: 22, 23 and 24 located at positions corresponding respectively to the positions 291-309, 311-341 and 1845-1867 of the sequence SEQ ID NO: 3, and may also comprise at least one of the conserved patterns of sequences SEQ ID NO: 25 and 26 located at positions corresponding respectively to the positions 1466-1490 and 1496-1521 of the sequence SEQ ID NO: 3, when said KAK protein is aligned with said sequence SEQ ID NO: 3.

According to a second particular embodiment, the plant according to the invention such that the expression and/or the activity of the ESK1 and TPS7 proteins is decreased is further such that the expression and/or the activity of the protein designated TPS6 is decreased, as compared to a non-mutagenized parent plant, the decrease in the expression and/or the activity of the TPS6 protein having been achieved by at least one mutation in the gene encoding the TPS6 protein, and such that the non-mutagenized TPS6 protein has at least 60% identity with the sequence SEQ ID NO: 65 and preferably comprising the TPS and TPP domains.

The non-mutagenized TPS6 protein as defined in the present invention has at least 60% identity with the sequence SEQ ID NO: 65 and in ascending order of preference at least 65%, 70%, 75%, 80%, 85%, 90%, 95%, 97%, 98% and 99% identity.

The best ortholog for the TPS6 protein in the plants of interest listed above is found via the PLAZA tool or via the PANTHER tool. The best ortholog for the TPS6 protein in the corn is Zm00001d028267.

The TPS6 protein whose the expression and/or the activity is decreased in the plant according to the invention is defined with reference to the TPS6 protein of *Arabidopsis thaliana* of SEQ ID NO: 65; indeed, depending on the plant species considered, the person skilled in the art is able to identify the ortholog of the protein designated TPS6 as follows which has:

- a TPS domain (Yang et al., 2012), comprising the conserved pattern of sequence SEQ ID NO: 12 and the conserved pattern of sequence SEQ ID NO: 13, located at positions corresponding respectively to the positions 213-217 and 235-246 of the sequence SEQ ID NO: 65, when said TPS6 protein is aligned with said sequence SEQ ID NO: 65, and
- a TPP domain (Yang et al., 2012), comprising the conserved patterns of sequence SEQ ID NO: 14, 15 and 16, located at positions corresponding respectively to the positions 666-671, 794-804 and 824-832 of the sequence SEQ ID NO: 65, when said TPS6 protein is aligned with said sequence SEQ ID NO: 65.

As an example, the TPS6 proteins are derived from *Arabidopsis thaliana* of sequence SEQ ID NO: 65 (designated AtTPS6 or AT1G68020), from *Zea mays* (Zm00001d028267, also designated GRMZM2G099860) of sequence SEQ ID NO: 66, from *Vitis vinifera* (designated VIT_00011634001) of sequence SEQ ID NO: 68, from *Populus trichocarpa* (designated POPTR_010G104500v3) of sequence SEQ ID NO: 69, or from *Sorghum bicolor* (designated SORBI_3001G450800) of sequence SEQ ID NO: 67.

According to an embodiment of the present invention, the plant according to the invention is a dicotyledon and said TPS6 protein has at least 70% identity with SEQ ID NO: 65 and in ascending order of preference at least 75%, 80%, 85%, 90%, 95%, 97%, 98% and 99% identity with SEQ ID NO: 65 and comprises the conserved pattern of sequence SEQ ID NO: 12 and the conserved pattern of sequence SEQ ID NO: 13, located at positions corresponding respectively to the positions 213-217 and 235-246 of the sequence SEQ ID NO: 65 when said TPS6 protein is aligned with said sequence SEQ ID NO: 65.

According to another embodiment of the present invention, the plant according to the invention is a monocotyledon and said TPS6 protein has at least 60% identity with SEQ ID NO: 65 and in ascending order of preference at least 65%, 70%, 75%, 80%, 85%, 90%, 95%, 97%, 98% and 99% identity with SEQ ID NO: 65 and comprises the conserved pattern of sequence SEQ ID NO: 12 and the conserved pattern of sequence SEQ ID NO: 13, located at positions corresponding respectively to the positions 213-217 and 235-246 of the sequence SEQ ID NO: 65 when said TPS6 protein is aligned with said sequence SEQ ID NO: 65 and may also comprise the conserved patterns of sequence SEQ ID NO: 14, 15 and 16, located at positions corresponding respectively to the positions 666-671, 794-804 and 824-832 of the sequence SEQ ID NO: 65, when said TPS6 protein is aligned with said sequence SEQ ID NO: 65.

Unless otherwise specified, the alignment between two peptide sequences and the calculation of the identity percentages are performed along the entire length of the peptide sequences using the computer program "needle" (Needleman et al., 1970) using the default parameters: "Matrix": EBLOSUM62, "Gap penalty": 10.0 and "Extend penalty": 0.5.

The reduction of the expression and/or the activity in a plant of the ESK1, TPS7 proteins and optionally KAK or TPS6 as defined above, can be achieved in different ways detailed below.

The term "decrease of the expression of a protein in a plant obtained by mutagenesis" refers to the decrease in the amount of protein produced by the plant obtained by mutagenesis as compared to a non-mutagenized parent plant in which the expression of said protein is not decreased.

The methods used to measure the decrease in the expression of a protein in a plant comprise for example the technique of the western blot.

The term "decrease of the activity of a protein in a plant obtained by mutagenesis" refers to the decrease of the activity of the protein produced by the plant obtained by mutagenesis as compared to a non-mutagenized parent plant in which the activity of said protein is not decreased.

The methods used to measure the decrease in the activity of a protein in a plant comprise, for example, the measurement of the enzymatic activity, by sugar assay, infrared, mass spectrometry or visual tests.

In this case, the decrease in the expression of each of the ESK1, TPS7, KAK and TPS6 proteins is measured by western blot and is compared respectively to the expression of the ESK1, TPS7, KAK and TPS6 proteins of a non-mutagenized plant.

In this case, the decrease in the ESK1 activity is measured by acetate assay or by infrared or by MS Maldi-TOF and is compared to the ESK1 protein of a non-mutagenized plant.

In this case, the decrease in the TPS7 activity is measured by sugar assay or by mass spectrometry and is compared to the TPS7 protein of a non-mutagenized plant.

In this case, the decrease in the KAK activity is measured by a visual test by observing the hyperbranched trichomes and is compared to the KAK protein of a non-mutagenized plant.

In this case, the decrease in the TPS6 activity is measured by sugar assay or by mass spectrometry and is compared to the TPS6 protein of a non-mutagenized plant.

The plant material (protoplasts, callus, cuttings, seeds, etc.) obtained from the plants according to the invention is also related to the present invention. The invention also covers the products obtained from plants according to the invention, in particular fodder, wood, leaves, stems, roots, etc.

The plants according to the invention are such that they have an improved digestibility. The plants in which the expression and/or the activity of the ESK1 and TPS7 proteins is decreased show an intermediate biomass production between that of the esk1 mutant and the wild type. The plants in which the expression and/or the activity of the ESK1, TPS7 and KAK proteins is decreased and those in which the expression and/or the activity of the ESK1, TPS7 and TPS6 proteins is decreased have an intermediate or equivalent biomass to that of a wild type plant.

The amount of biomass is calculated by measuring the dry weight per kg of fresh weight from ten plants.

The digestibility is assessed by digesting the parietal compounds with the so-called "Onozuka cellulase" enzymatic cocktail as described in Bensussan et al., 2015. The digestibility protocol corresponds to an in vitro test aimed at estimating the insoluble fibre content after acid hydrolysis.

The invention also relates to a method for preparing a plant with improved digestibility according to the invention in which the expression and/or the activity of the protein designated ESK1, and the expression and/or the activity of the protein designated TPS7, is decreased, said method comprising the steps of mutagenesis of the genes encoding the proteins designated ESK1 and TPS7.

According to a first particular embodiment, this method allows the preparation of a plant such that the expression and/or the activity of the protein designated KAK, is also decreased (in addition to those of ESK1 and TPS7) and comprises an additional step of mutagenesis of the gene encoding the protein designated KAK.

According to a second particular embodiment, this method allows the preparation of a plant such that the expression and/or the activity of the protein designated TPS6, is also decreased (in addition to those of ESK1 and TPS7) and comprises an additional step of mutagenesis of the gene encoding the protein designated TPS6.

The decrease of the expression and/or the activity of each of the ESK1, TPS7, KAK and TPS6 proteins is achieved by mutagenesis of the genes encoding their respective proteins.

For example, a mutation within the encoding sequence of a gene can induce, depending on the nature of the mutation, the expression of an inactive protein, or a protein with an altered activity. A knock-out type mutation where the reading frame has a premature stop codon can also induce a decrease in the expression of this protein.

The mutants can be obtained by deletion, insertion and/or substitution of one or more nucleotides, for example by deletion of all or part of the encoding sequence of the gene encoding the protein or of its promoter or by the insertion of an exogenous sequence within the encoding sequence of the gene encoding the protein or of its promoter.

The mutagenesis can be implemented by the induction of random mutations, for example using physical or chemical agents such as the EMS (Ethyl Methane Sulfonate) or the random insertion mutagenesis, followed by the selection of the mutants with the targeted mutations. The methods of high-throughput mutagenesis followed by the selection of the mutants are well known. For example, the TILLING (Targeting Induced Local Lesions IN Genomes) method is described in particular in McCallum et al. 2000, Colbert et al. 2001, Henikoff et al. 2003 and Till et al. 2003. The TILLING technique has been continuously developed on different grown species as evidenced by many publications such as for example Taheri et al., 2017.

Alternatively, the mutagenesis can be implemented by methods using nucleases (TALEN, CRISPR/Cas9, etc.), described in Shan et al., 2013, Feng et al., 2013, Svitashev et al., 2015 and Char et al., 2017.

For some plants such as the corn, the mutants may be insertion lines, for example chosen from the collection of lines so-called UFMu mutator; the research for the corn lines that have a transposon insertion in the orthologous genes of interest can be carried out using the website https://maizegdb.org/data_center/stock.

The genotyping of the lines is performed according to the recommendations of the authors (McCarty et al., 2013).

In the absence of insertion of transposable elements or TILLING mutants in the selected genes, the CRISPR/Cas9 mutagenesis strategy is performed.

Finally, the inhibition of the expression of the target protein can be achieved by an RNA interference (RNAi) technique, by expression of an antisense RNA or by aptamers.

The present invention relates to a method for increasing the growth of a plant carrying the esk1 mutation, characterized in that it comprises a step of genetically modifying said plant to decrease the expression and/or the activity of the protein designated TPS7.

Preferably, this method also comprises a step of genetically modifying said plant to decrease the expression and/or the activity of the protein designated KAK or a step of genetically modifying said plant to decrease the expression and/or the activity of the protein designated TPS6.

The invention also relates to a use of a plant according to the invention for the production of biofuel.

The invention further relates to a use of a plant according to the invention for the animal nutrition.

Figure 1:
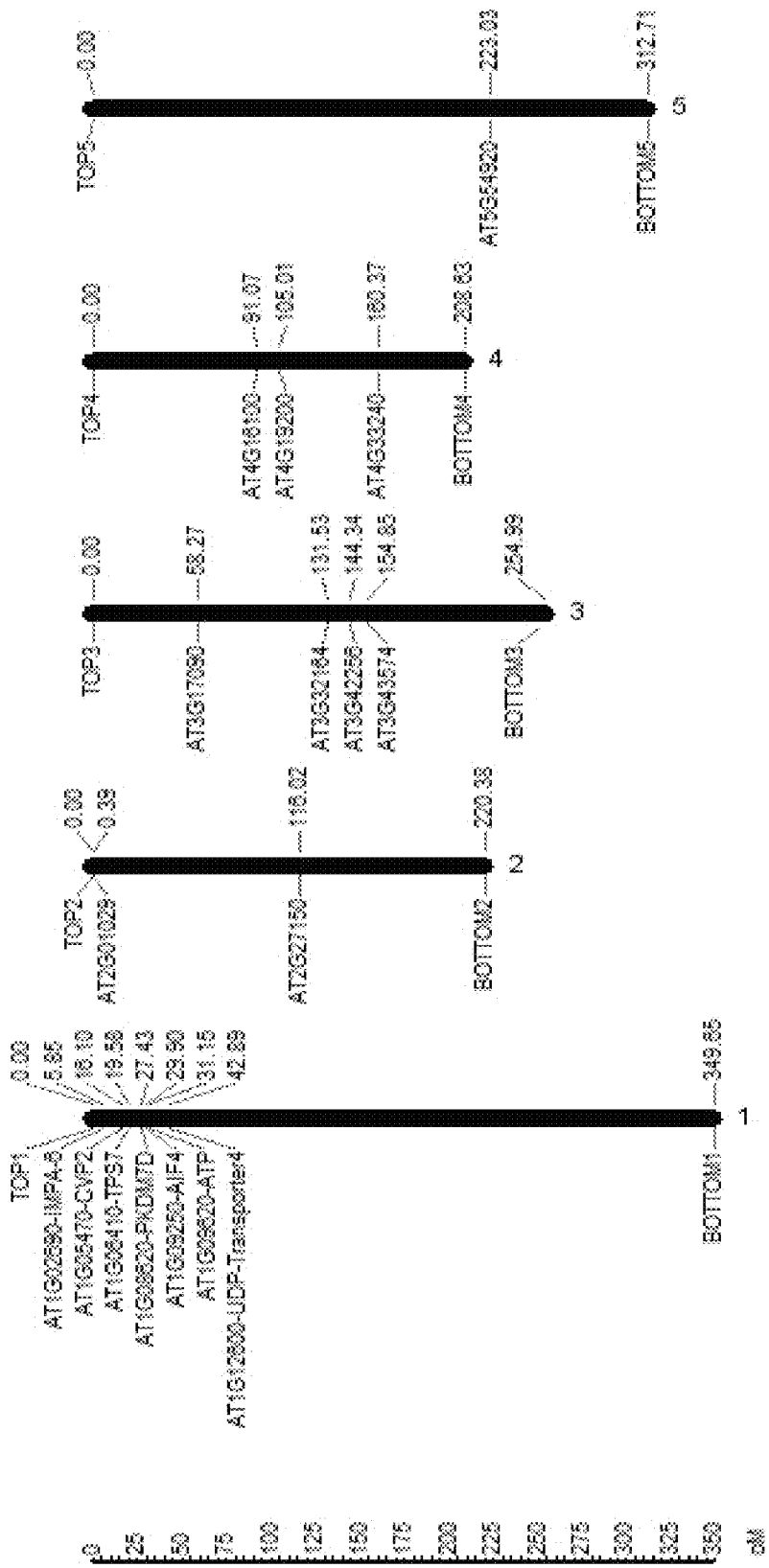

FIG. 1: Physical map of the candidate genes selected for the beem241C line. Beem stands for "biomass enhancement under eskimo 1 mutation". These are mutagenized esk1 mutant lines, whose the dwarfing character is attenuated. Position of the SNP variants from the bioinformatics analysis.

Figure 2:
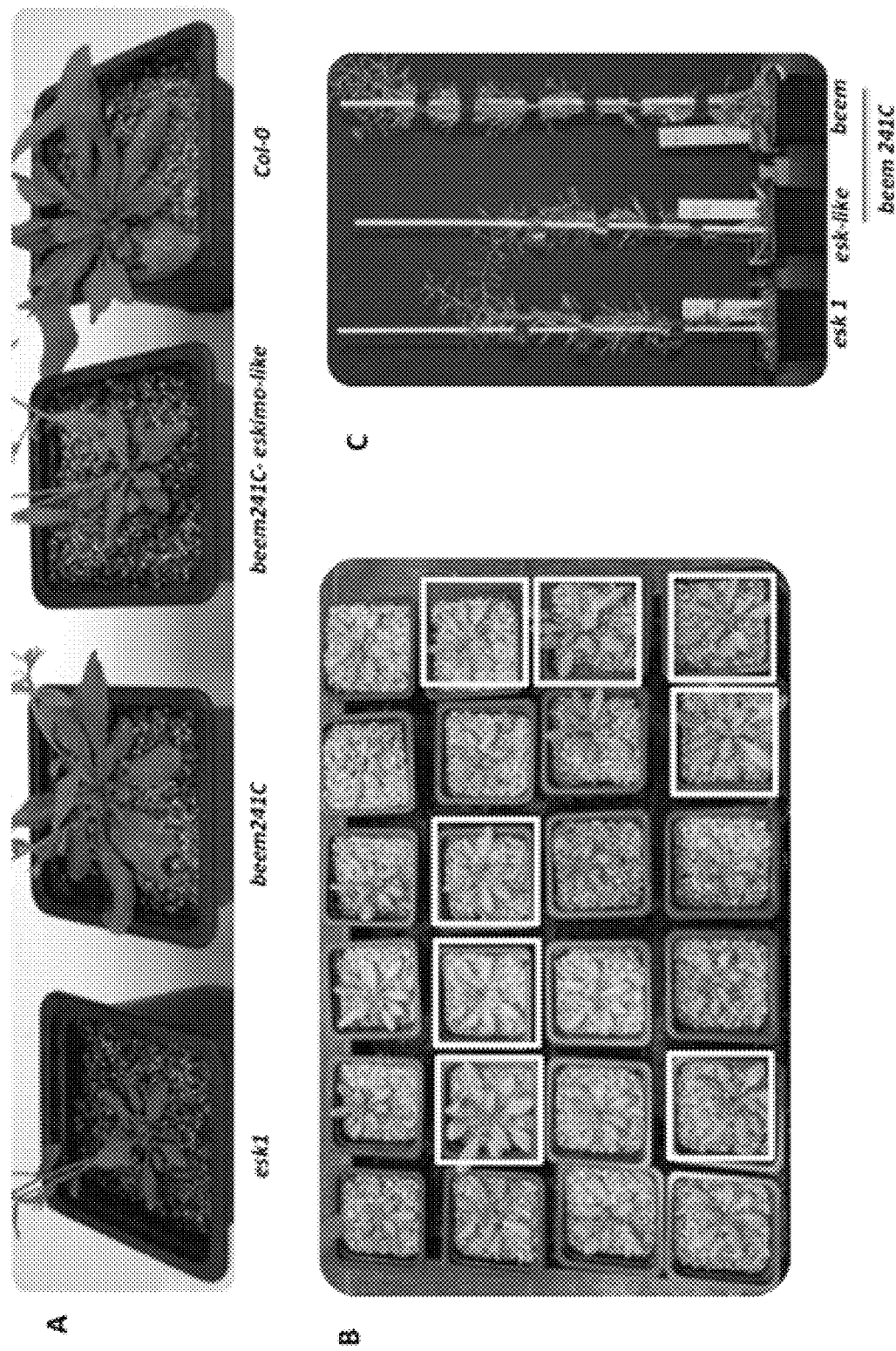

FIG. 2: Phenotype of the esk1, beem241C (esk1 mutant line suppressed or not suppressed for the dwarfism after a chemical mutagenesis) and wild type mutants. (A) Plants representative of each genotype grown under standard conditions: wild type Col-0, suppressed beem241C. eskimo-like beem241C in segregation into the unsuppressed mutagenized population and esk1 (B) Representation of the segregation of beem241C line. The white squares show the plants that exhibit the beem phenotype (C) Comparison of the height of the plants between the esk1 parental mutant and the beem241C suppressed mutant.

Figure 3:
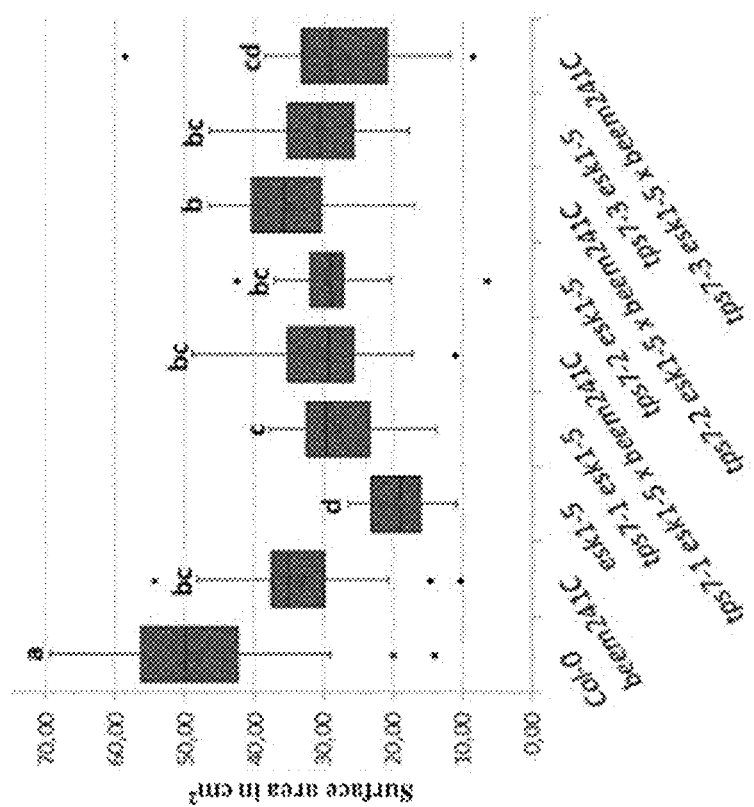

FIG. 3: A Comparison of the surface of the rosettes between different lines. The letter symbolizes the class to which each line belongs, a class determined by a multiple comparison test (Tuckey). The bar in the middle of each box represents the median, the diamond indicates the mean, the ends of each box represent the $1^{st}$ and the $3^{rd}$ quartile of the series, the standard deviation is represented by the vertical bars, the extreme individuals are indicated by a black dot. B Staffing of the Allelism test.

Figure 4:
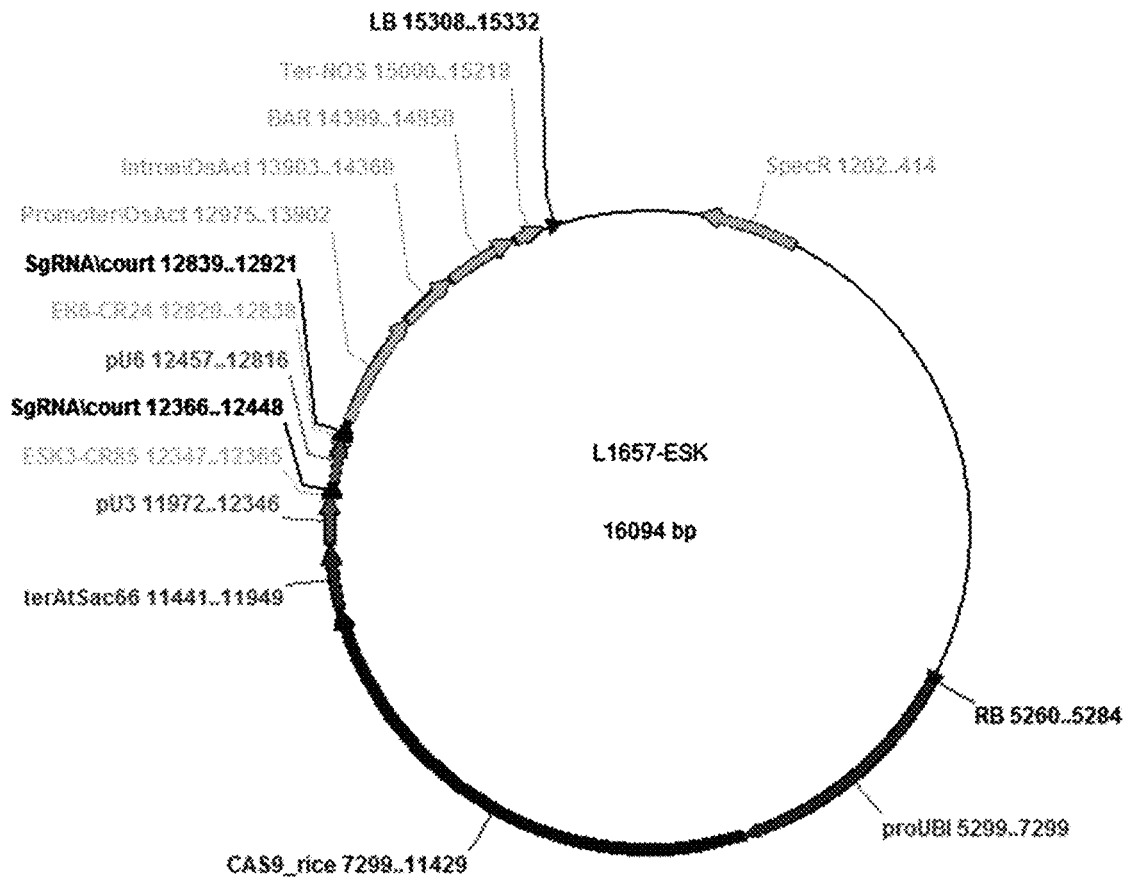

FIG. 4: Graphical representation of the L1657 plasmid.

Figure 5:
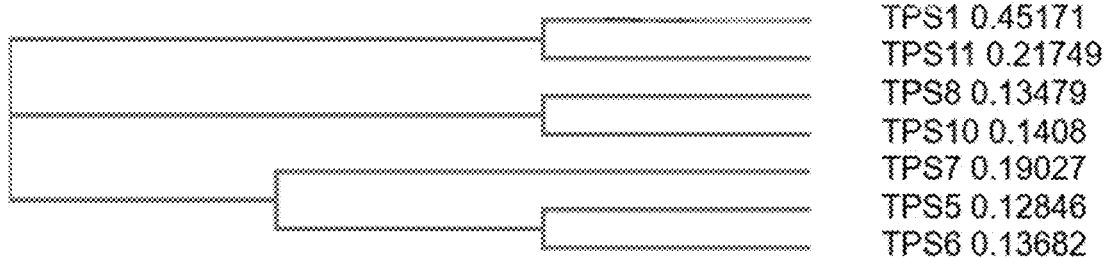

FIG. 5: Phylogenetic tree made with protein sequences of the class 2 TPS genes anchored with the protein of the TPS1 gene. The values indicate the length of the branches.

Figure 6:
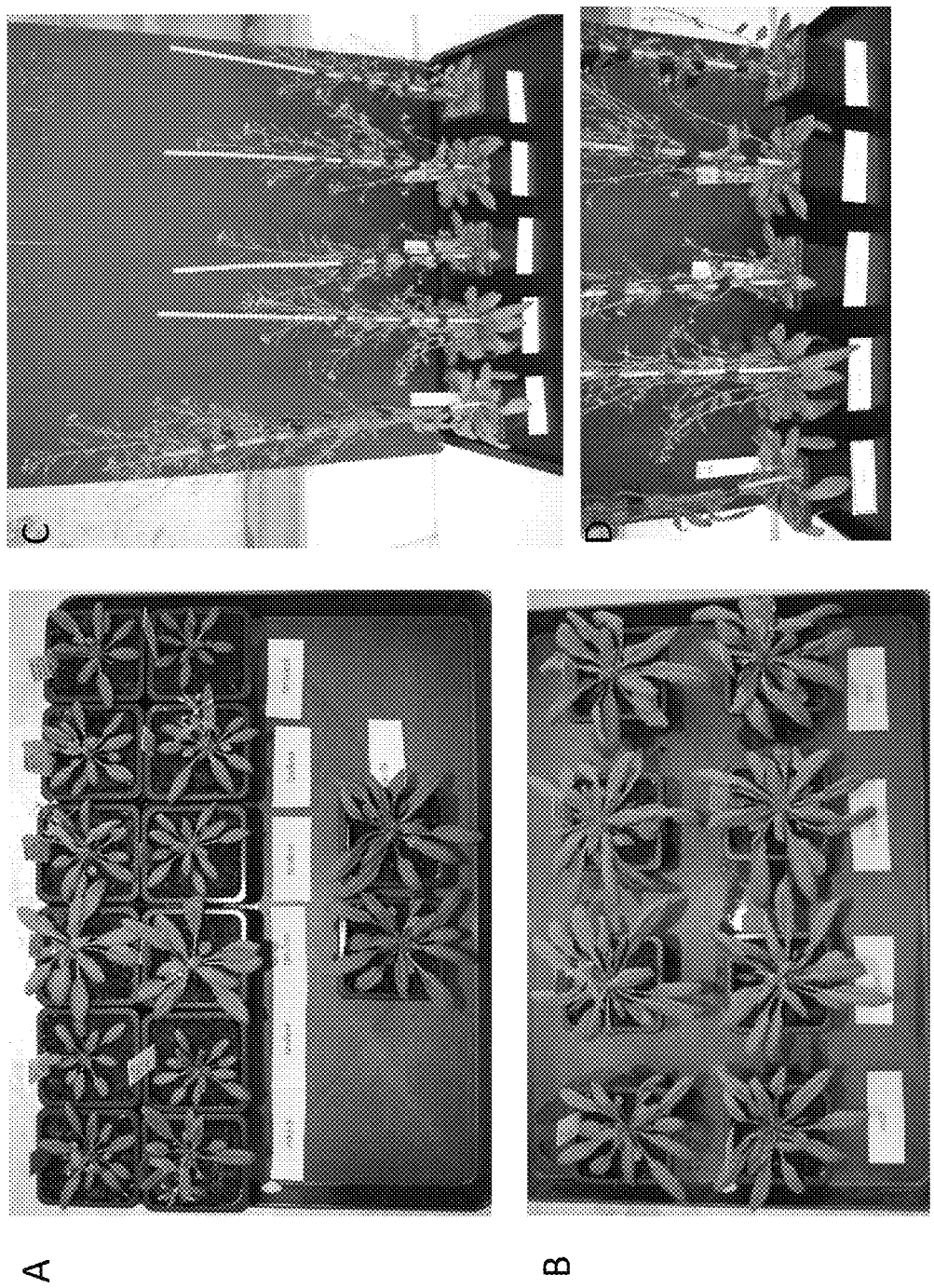

FIG. 6: *Arabidopsis* plants at the flower induction stage and at flowering.

A—Above from left to right: 2 plants of the esk1 mutant, followed by 2 plants of the tps6esk1 double mutant, by 2 plants of the tps7esk1 double mutant, by 2 plants of the tps8esk1 double mutant, by 2 plants of the tps9esk1 double mutant and by 2 plants of the tps10esk1 double mutant. Below are showed 2 wild type plants (Col0).

B— From left to right: 2 wild type (Col0) plants, 2 plants of the tps6 single mutant, 2 plants of the tps6tps7 double mutant and 2 plants of the tps7 single mutant.

C— Flowering plants. From left to right, the Col0 wild type plant, followed by the tps6tps7esk1 triple mutant, the tps6esk1 double mutant, the tps7esk1 double mutant and the esk1 single mutant.

D—View of the rosettes of the whole plants shown in C.

FIG. 7: Position of the CrispR targets on the genomic sequences of the Zm00001d022582 (FSK3) and Zm00001d028751 (ESK6) genes.

FIG. 8: Morphological characterization of the corn plants. A on the left: Observation of the size of the esk3.1, esk6.1 and esk3.1esk6.1 mutant plants compared to the size of the wild type (WT) plant at the flowering stage and the right picture on the right shows a leaf defect visible from the $4^{th}$ leaf. B: Appearance of the ligulate leaves over time. C: Measurement of the height of the plants at the flowering stage. The letters a and b according to the Tukey test indicate that the plants belong to two significantly different groups. D: Distribution of the genotypes depending on the length and width of the $8^{th}$ leaf.

Figure 9:
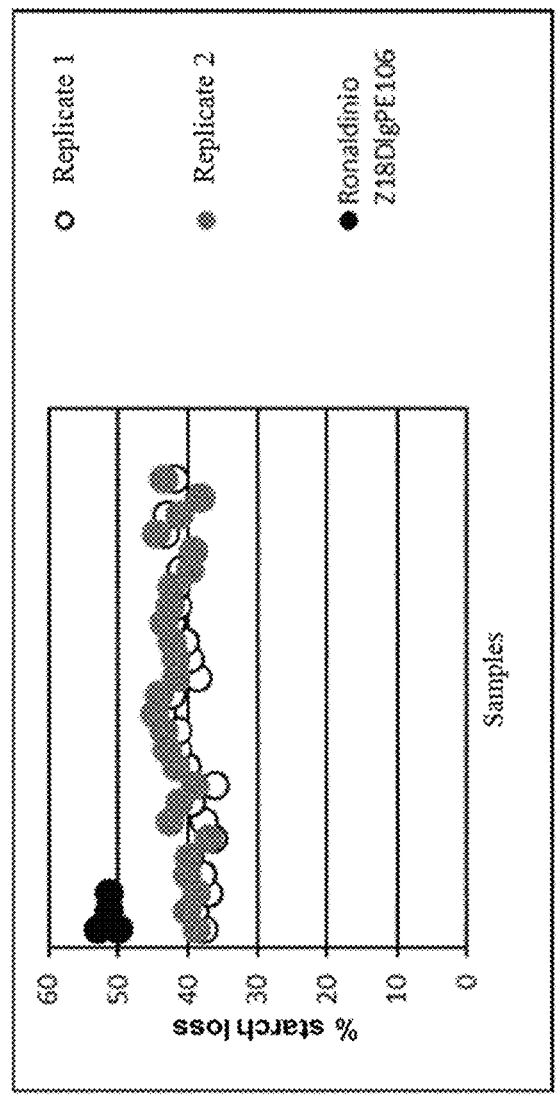

FIG. 9: Result of the amylase treatment performed on the samples. Two technical replicates per sample were performed, the results are compared to those from the standards of the laboratory (grey dots=replicate 1, white dots=replicate 2, black dots=standards).

Figure 10:
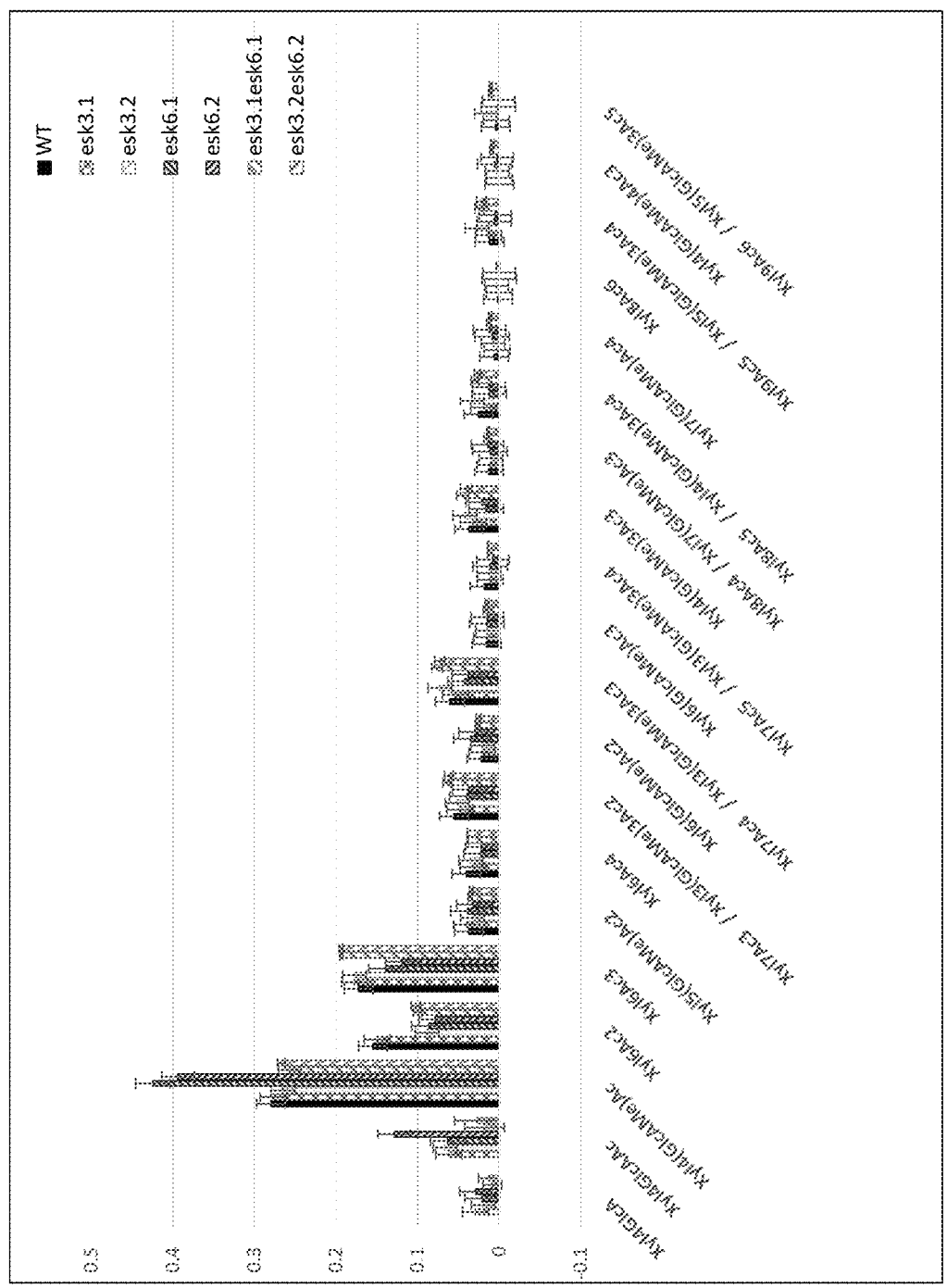

FIG. 10: Oligoxylans obtained after xylanase treatment and MALDI TOF identification. The different oligoxylans are distributed according to their m/z (horizontal axis) and their proportion on the vertical axis. The genotypes are represented by the pictograms, 3 biological repetitions per genotype except for the esk3.2esk6.2 batches (2 biological repetitions).

Figure 11:
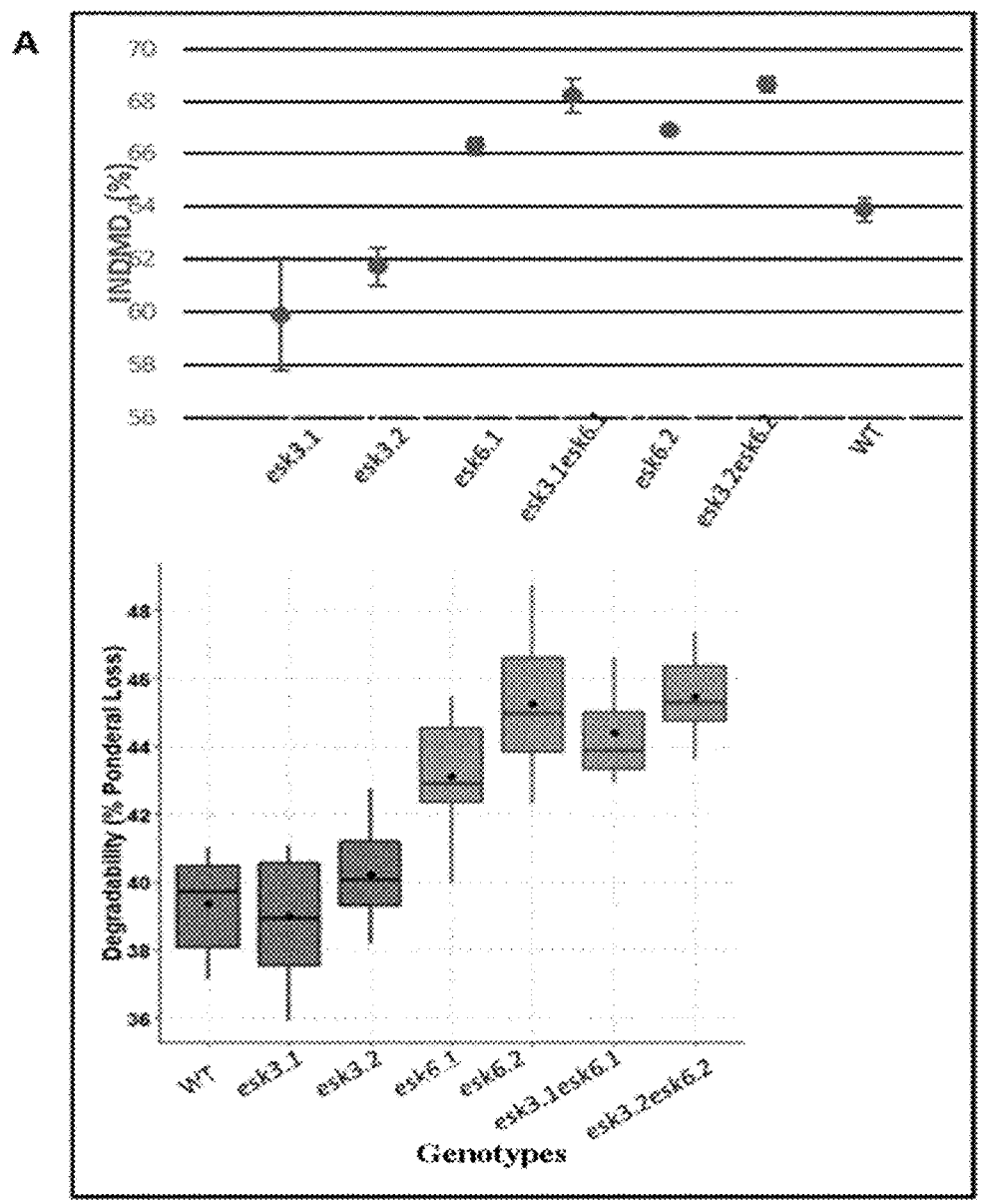
Figure 11:
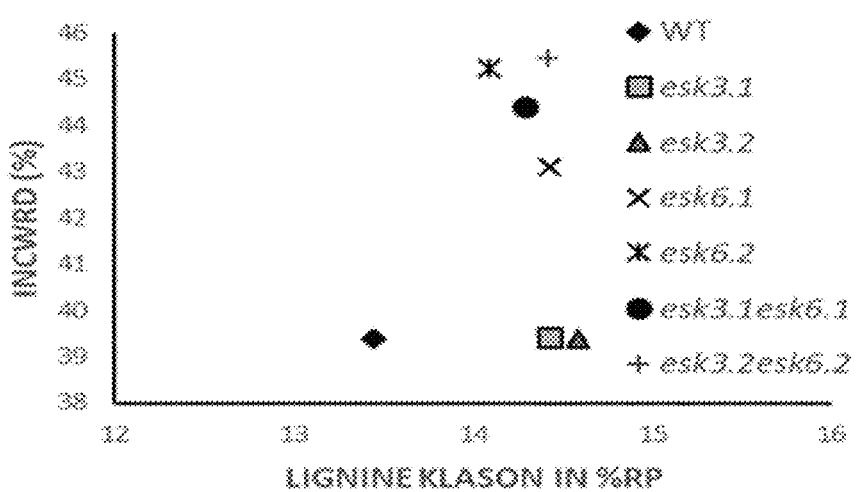

FIG. 11: Evaluation of the in vitro digestibility of the dry matter (INDMD) and the parietal residues (INCWRD) and the lignin contents (klason) of the walls. A: on the top, averages of the digestibility of the dry matter depending on the genotypes (3 biological repetitions×2 technical repetitions per genotype); on the bottom, the digestibility of the parietal residues depending on the genotypes (3 biological repetitions per genotype×3 technical repetitions). The test of Tukey shows that the genotypes are distributed into two significantly distinct groups (a and b). B: table of the values of the lignin content of the parietal residues according to the genotypes. (3 biological repetitions×2 technical repetitions per genotype) C: distribution of the genotypes depending on the digestibility of the parietal residues and of the quantity of lignin.

Figure 12:
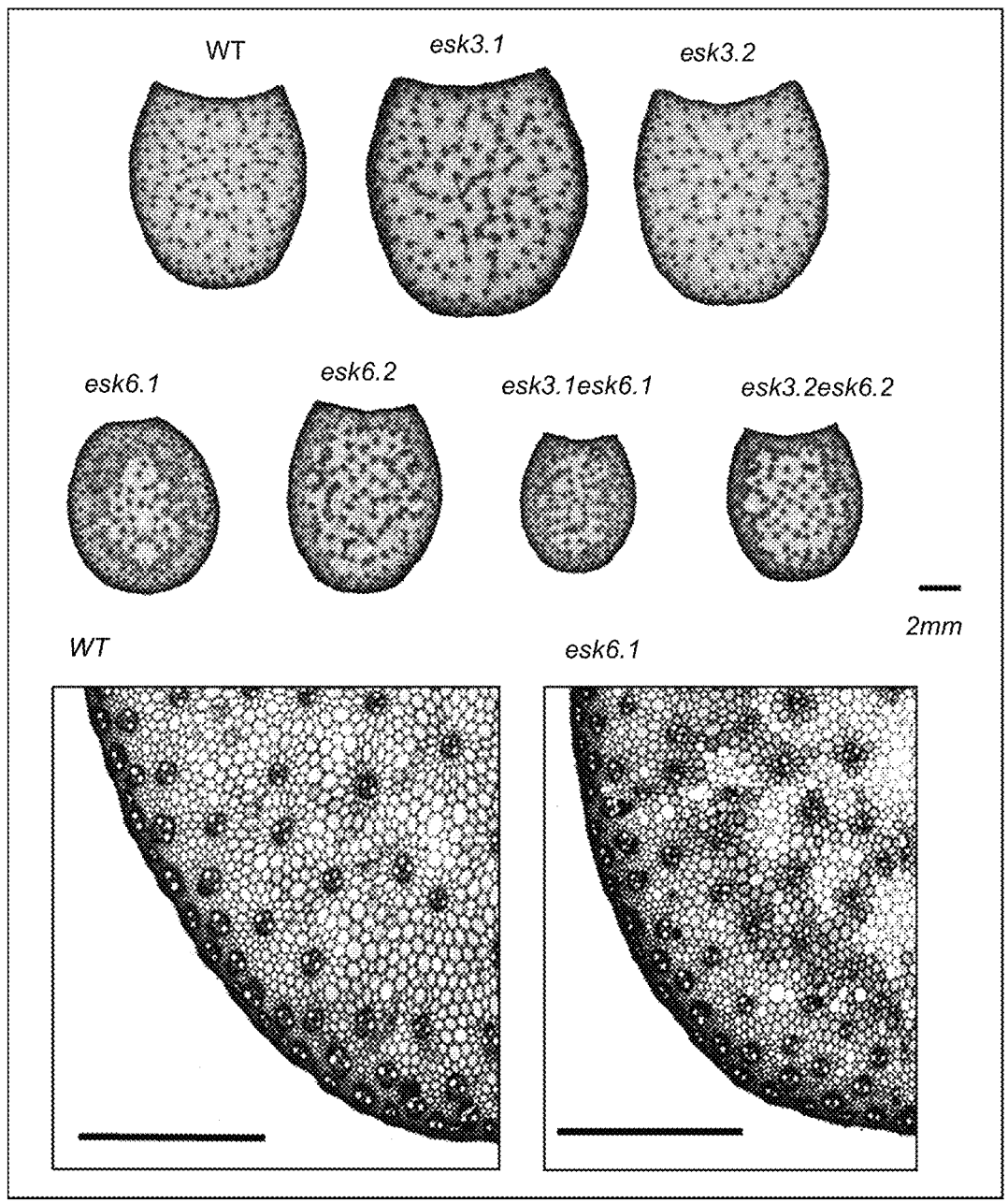

FIG. 12: Cross sections of corn internodes after FASGA staining. The low-lignified tissues are coloured blue and the lignified tissues are coloured pink. On the bottom, magnification of the perivascular regions of the wild type plant and of the esk6.1 mutant which show very blue and large cells around the vessels compared to those of the wild type plant.

Figure 13:
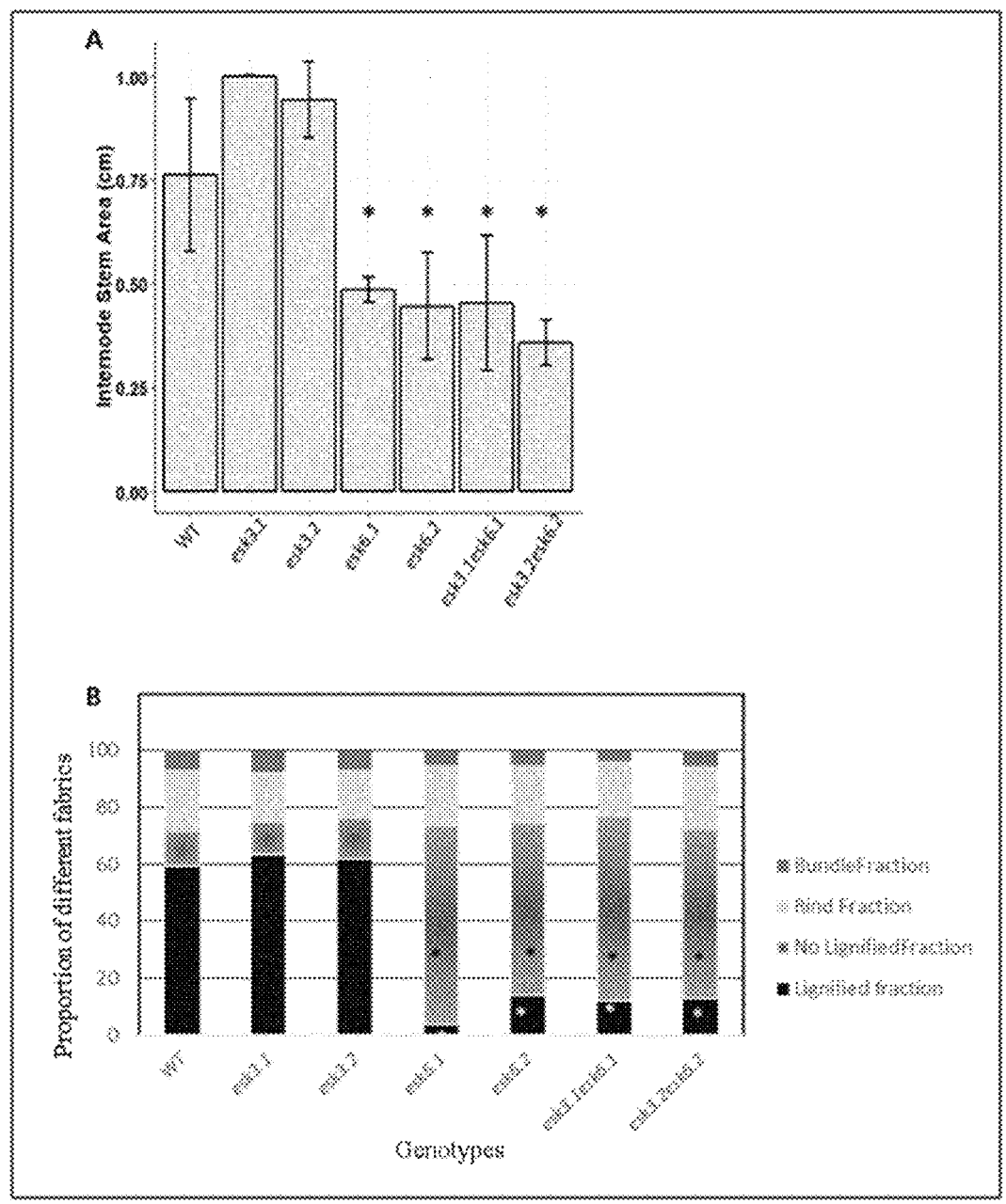

FIG. 13: Measurements of the surfaces of the cross sections of internodes under ear and quantification of the different tissues observed after the FASGA staining. The stars indicate that the differences are significant (n=57).

EXAMPLE 1: HIGHLIGHTING OF THE TPS7 MUTATION AS A SUPPRESSOR OF DWARFISM IN *Arabidopsis thaliana* AND CHARACTERIZATION OF THE ESK1 AND TPS7 DOUBLE MUTANT PLANTS IN *Arabidopsis thaliana*

Materials and Methods

1. Obtaining the "Beem" by Mutagenesis of the Eskimo1 Mutant

After chemical mutagenesis by EMS (3%), homozygous esk1-5 mutant seeds of *Arabidopsis thaliana*, 4500 M1 plants were grown, then groups of 7 M1 plants were performed. 200 M2 seeds per group were then sown and the groups that had 4 to 5 M2 plants having a growing faster than those of the esk1 mutant were isolated. These plants, called "beem" for "Biomass Enhancement under Eskimo1 Mutation", were backcrossed with the esk1-S mutant and self-fertilized to observe again the suppression of the dwarf phenotype in M3. Thus 12 lines containing suppressors of the dwarfism of the Atesk1 mutant were isolated. Crosses between the beem suppressors and the observations of the segregations of the phenotypes in F1 and in F2 indicate that the mutations affect different genes except for the beem308A and beem396B which are allelic. The DNA extracted from group of 100 F2 beem plants and the sequencing of the genomes with a depth of 100× was performed for 5 beem (563B, 396B, 241C, 142A, 648B).

The esk1-S mutant is genotyped with the pair of primers ESK1-5 #R2 and ESK1-5 #L1 for the wild allele and the pair of primers LBSalk2 and ESK1-5 #R2 for the mutated allele.

The tps7-1 mutant is derived from the SALK135044 line and is genotyped with the primers LBSalk2 and RP-Salk135044 for the mutant allele and RP-Salk135044 and LP-Salk135044 for the wild type allele.

The tps7-2 mutant is derived from the SALK116341c line and is genotyped with the primers RP-Salk116341 and LBSalk2 for the mutant allele and with the primers RP-Salk116341 and LP-Salk11341 for the wild type allele.

The tps7-3 mutant is the GABI341E02 line. The mutant allele is determined by PCR with the primers Gabi08409 and RP-GK341E02 for the mutated allele and with the primers RP-GK341E02 and LP-GK341E02 for the wild type allele.

The tps7-4 mutant is genotyped by PCR with the primers TS7 #U1 and TPS7 #L1 and the sequencing determines the presence of the SNP (G in A) relative to the reference sequence.

The sequences of the PCR products are obtained by the Sanger method and the sequences are aligned to the reference wild type gene to determine the presence of the SNP.

The sequences of the T-DNA primers are: LBSalk2, Gabi08409, Lb1.3.

TABLE 1

Primers used for the PCR

The kak-7 and kak-8 mutants are those described in the publication Bensussan et al. 2015.

| Primer name | Sequence | Denomination (SEQ ID NO:) |
|---|---|---|
| ESK1-5#R2 | 5' CAATGGACTCAGGCATTATT3' | 31 |
| ESK1-5#L1 | 5' GAGTTTCCTTTCTCCACC3' | 32 |
| LBSalk2 | 5' GCTTTCTTCCCTTCCTTTCTC3' | 33 |
| RP-Salk135044 | 5' CAATACCGTGCATTGTGTCAG3' | 34 |
| LP-Salk135044 | 5' GAGGGTAAAACCTGGCAAAAG3' | 35 |
| RP-Salk116341 | 5' TTCATTGTCAGTGGAAGAGGG3' | 36 |
| LP-Salk11341 | 5' CAGACCAACAAACTCCCAGTC3' | 37 |
| Gabi08409 | 5' ATATTGACCATCATACTCATTGC3' | 38 |
| RP-GK341E02 | 5' GCTGGAGTATTACGGGAGGAC3' | 39 |
| LP-GK341E02 | 5' TTCACTGCCTGACCACCTAAG3' | 40 |
| TS7#U1 | 5' TCAATGGCCGGAAAGGGAAA3' | 41 |
| TPS7#L1 | 5' GGGCTTCATCAAGTTCACGC3' | 42 |
| Lb1.3 | 5' CATCAAACAGGATTTTCGCC 3' | 43 |

2. Bioinformatics Analysis

A bioinformatics analysis was conducted by aligning the sequences ("reads") of the genome of 5 beem mutants (S63B, 396B, 241C, 142A, 648B) to the reference genome using the CLC Genomics Workbench 7.5.2 (Qiagen) software, knowing that the beem mutants were not allelic to each other.

Sequence Alignment

The "trimming" function provided by the CLC Genomics Workbench software was used. A trimming by quality and by sequence length was done initially, with the following parameters:

quality score limit=0.05 (Phred value equivalent to a quality score of 40: the probability of calling a base incorrectly is 1 in 10 000).

trim. of ambiguous nucleotides=0 (no ambiguous nucleotides is allowed).

length trim.=reads with a length of less than 80 bp are eliminated.

The "reads" were mapped to the *Arabidopsis* reference genome (TAIR 10.0) according to the default parameters. However, the fraction length parameters (value of the alignment that must match the reference sequence before being put into the list of mapped variants) and the similarity fraction (minimum percentage of identity between the "read" and the reference sequence) are 0.9 and 0.05 respectively.

The SNP Detection

The "basic detection of variants" function was used with the following parameters: minimum coverage=6; minimum count=2; and minimum allelic frequency=80%. A list of SNP for each beem line was obtained. Then, the list of the possible candidates was selected according to the following parameters (Abe et al., 2012; Hartwig et al. 2012): a) SNP/INDEL (insertion or deletion in a biological sequence) exclusive and unique to the beem241C line, b) the SNP/INDEL must be located in an encoding region to have effects on the amino acid sequences, c) the SNP/INDEL has an allelic frequency between 80-100%.

The Validation of the SNP Candidates 480 plants of the F2 progeny of the backcrossing: beem241Cxesk1-5 as well as 24 plants of the esk1-5 parental line and 10 Col-0 wild type plants were sown in the greenhouse, in order to assess the recessivity of the beem241C mutation for the selected morphological traits. The suppressed plants have an appearance close to that of a wild type plant, whereas the non-suppressed plants have small rosettes, dark green leaves and a smaller plant height than wild type plants.

The DNA of the suppressed "beem" plants was extracted individually. All the plants were genotyped by PCR to verify their homozygosity for the esk1 mutation. Then primers were defined on the candidate genes for which the EMS mutations have an effect on the amino acid sequence (Table 2).

TABLE 2

Primers used. Sequences of the primers for the exclusive and independent candidate genes responsible for the suppression of the dwarf phenotype of the beem241C line.

| Chromosome | Primer | Sequence | Denomination (SEQ ID NO:) |
|---|---|---|---|
| 1 | AT1G02690 F | 5' CAATCTCCTGAAGCTAGCCGT 3' | 44 |
|   | AT1G02690 R | 3' CGAGAGTACGTTCTTCGTGTTC 5' | 45 |
|   | AT1G05470 F | 5' TCCGTGGTAGCAGCAG 3' | 46 |
|   | AT1G05470 R | 3' TAACAATAGAGGCAAAAGCAT 5' | 47 |
|   | AT1G06410 F | 5' GGGCTTCATCAAGTTCACGC 3' | 48 |
|   | AT1G06410 R | 3' TCAATGGCCGGAAAGGGAAA 5' | 49 |
|   | AT1G08620F | 5' TGGTGTCCAGGGTTTAGCTG 3' | 50 |
|   | AT1G08620 R | 3' TGATAGCTAGAAAGAGTCGGAGT 5' | 51 |
|   | AT1G09250 F | 5' AGAGACTTTCCGGCAACCAG 3' | 52 |
|   | AT1G09250 R | 3' GTGATACGGCGGATCGAGTT 5' | 53 |
|   | AT1G09620 F | 5' AGCCGGTGATGTCAAGATCG 3' | 54 |
|   | AT1G09620 R | 3' TCATTCATCTGCTGAGGGCG 5' | 55 |
|   | AT1G12600 F | 5' TCTTCGCCTTTGTTTCCGGT 3' | 56 |
|   | AT1G12600 R | 3' CGTTAATGGCATCTGCGAGG 5' | 57 |
| 4 | AT4G33240 F | 5' CTGGACCTTCCCCTAGACCC 3' | 58 |
|   | AT4G33240 R | 3' CAACTTCGGGCTCAAAGGAC 5' | 59 |
| 5 | AT5G54920 F | 5' CCCATGGACCTTGTGAGCTA 3' | 60 |
|   | AT5G54920 R | 3' GTCCAATGTTGCAGGGGAGA 5' | 61 |
| Esk 1-5 genotyping | | | |
| ESK1-5 | LP | 5' GAGTTTCCTTTCTCCACC 3' | 62 |
|   | LB | 3' CAATGGACTCAGGCATTATT 5' | 63 |
|   | SALK LB line | 3' GCTTTCTTCCCTTCCTTTCTC 5' | 64 |

The amplification products are sequenced by the company Beckman Coulter Genomics (24 "beem" suppressed plants, 7 sister plants with the eskimo-like phenotype and one esk1 plant). The analysis of the wild type or mutant alleles indicates whether or not there is a correlation with the phenotype of the plants observed using the CLC Genomics Workbench 7.5.2 (Qiagen) software.

Results

1. Identification of the beem241C Mutation

Approximately 2000 SNP/INDEL were obtained for each beem line, but only those that were exclusive for the beem241C line and met the established selection criteria (allelic frequency 80%-100%, SNP/INDEL located on exons) were retained. Thus, for the beem241C line, 29 SNP/INDEL were obtained with a coverage of 76% for all the chromosomes. But only nine candidate genes distributed on the chromosomes 1, 4 and 5 are unique and appear with an allelic frequency ranging from 80 to 100%. They are located in the encoding regions of the genes (FIG. 1 and Table 3).

A cluster of mutations on the top of the chromosome 1 is found.

TABLE 3

Candidate genes distributed on the chromosomes 1, 4 and 5 found during the bioinformatics analysis.

| Chr. | Region | Name | Type | Ref. | Mut. | Cover. | Freq. |
|---|---|---|---|---|---|---|---|
| 1 | 584 922 | AT1G02690 IMPA-6 | SNV | G | A | 50 | 94 |
|   | 1 609 843 | AT1G05470 CVP2 | SNV | G | A | 60 | 100 |

TABLE 3-continued

Candidate genes distributed on the chromosomes 1,
4 and 5 found during the bioinformatics analysis.

| Chr. | Region | Name | Type | Ref. | Mut. | Cover. | Freq. |
|---|---|---|---|---|---|---|---|
| | 1 958 038 | AT1G06410 TPS7 | SNV | G | A | 63 | 100 |
| | 2 743 086 | AT1G08620 PKDM7D | SNV | G | A | 51 | 98 |
| | 2 989 893 | AT1G09250 AIF4 | SNV | G | A | 56 | 93 |
| | 3 114 526 | AT1G09620 ATP | SNV | G | A | 53 | 89 |
| | 4 288 712 | AT1G12600 UDP | SNV | A | T | 28 | 89 |
| 4 | 16 036 646-16 036 647 | AT4G33240 FAB1A | D | TA | — | 46 | 80 |
| 5 | 22 302 999-22 303 000 | AT5G54920 * | I | — | T | 25 | 80 |

Chr. Chromosome, Ref. Reference nucleotide, Mut. Mutant nucleotide, Cover. Coverage, Freq. Frequency.
* Unknown Protein, (SNV) Single Nucleotide Variant, (D) Deletion, (I) Insertion, (G) Guanine, (A) Adenine, (T) Thymine.

Most of the mutations on the chromosome 1 show changes from G by A. On the chromosomes 4 and 5 the variants correspond to deletions and insertions rarely found by EMS chemical mutagenesis. CVP2 and TPS7 are the unique variants that have a frequency of 100% with 60 and 63 sequences respectively.

M2 beem241C plants were backcrossed five times with their esk1 parent. The resulting F2 population showed a segregation for the size of the rosette of 138 beem plants: 342 unsuppressed plants (Test of the Positive Chi2 for the expected segregation 1:3-p-value=0.05778) (FIG. 2). This result confirms that the mutation responsible for the suppressed phenotype is recessive. The DNA of the 138 suppressed plants was extracted individually to verify by PCR that all the plants are esk1 homozygous, and then the sequencing of the candidate genes around the detected SNP was performed.

The suppression results in the change of a serine to proline at the codon 814 of the encoding sequence (CDS) of TPS7 potentially leading to the translation of the complete TPS domain (Trehalose Phosphate Synthase) and the modified TPP domain (Trehalose Phosphate Phosphatase) of the protein.

2) Complementation Tests with the T-DNA Insertion Mutants in the TPS7 Gene

The tps7-1, tps7-2, tps7-3 mutants were crossed with the esk1-S mutant to select in F2 the tps7-1esk1-5, tps7-2esk1-5 and tps7-3esk1-5 double mutants using the primers identified in Table 1.

To perform the complementation test, these double mutants were crossed with the beem241C mutant and the surface of the rosettes of the F1 progenies (beem241C tps7 esk1) was measured after 4 weeks of growth. The surface of the rosettes of the F1 progenies (beem241C tp7s esk1) observed is similar to that of beem241C. The results of the complementation tests shown in FIG. 3 therefore indicates that beem241C is tps7.

It is also observed that the tps7esk1-5 double mutants have an intermediate phenotype between that of the wild type plant and that of the esk1-S mutant as observed in the beem241C mutant, the size of the rosettes being larger than that of the esk1-S mutant.

3) Biomass Production

To assess the biomass production, the plants were grown on the Phenoscope phenotyping machine (Tisne et al. 2013), under controlled and reproducible conditions. The dry matter weight of the rosettes aged of 44 days and dehydrated for 48 h was measured.

The results of this measurement are available in Table 4.

It can be seen that the tps7 single mutants show a significantly higher biomass (23 to 32%) than the wild type under irrigated and water deficit conditions.

The tps7 esk1-5 double mutants have a higher biomass than that of the esk11-5 mutant under irrigated conditions.

TABLE 4

Biomass (dry matter) of the *A. thaliana* rosettes aged of 44 days collected on the Phenoscope. The number of individuals measured in each condition for each genotype is indicated in the column N.

| | Biomass (in g) | N | Biomass in % |
|---|---|---|---|
| WT (Col-0) | 0.22 g +/− 0.04 g | 5 | 100% |
| esk1-5 | 0.06 g +/− 0.02 g | 2 | 27% |
| tps7-1 | 0.27 g +/− 0.03 g | 5 | 123% |
| tps7-2 | 0.29 g +/− 0.04 g | 6 | 132% |
| tps7-3 | 0.29 g +/− 0.02 g | 6 | 132% |
| tps7-1 esk1-5 | 0.13 g +/− 0.02 g | 6 | 59% |
| tps7-2 esk1-5 | 0.13 g +/− 0.02 g | 6 | 59% |
| tps7-3 esk1-5 | 0.12 g +/− 0.01 g | 6 | 54.5% |

EXAMPLE 2: HIGHLIGHTING OF THE SELECTIVE EFFECT OF THE TPS7 MUTATION AS A SUPPRESSOR OF DWARFISM IN *Arabidopsis thaliana* AND CHARACTERIZATION OF THE ESK1, TPS7 AND TPS6 TRIPLE MUTANT PLANTS IN *Arabidopsis thaliana*

The obtaining of the tpsesk1 double mutants were performed from lines carrying mutation in each of the class 2 genes (Table 5 and FIG. 5).

TABLE 5

List of the class 2 TPS genes with their identifier (ID), the mutant lines obtained at the Stock Center and the oligonucleotides used to identify the homozygous mutant plants. The T-DNA oligonucleotides are those recommended on the website http://signal.salk.edu/tdnaprimers.2.html

| Gene | ID | Mutant lines | oligo LP | Oligo RP |
|---|---|---|---|---|
| TPS5 | AT4G17770 | SALK_144791 | SALK_144791#LP TGATCGTTCTTTATGGCAA GC (SEQ ID NO: 70) | SALK_144791#RP GCATTTGCTTCTCTGCTTC TG (SEQ ID NO: 71) |
| TPS6 | AT1G68020 | SAIL_1227_H10 | SAIL1227_H10#LP TGTCACCAAACAACACTC AGC (SEQ ID NO: 72) | SAIL1227_H10#RP TACGAGCTCAGAGAAGGG TTG (SEQ ID NO: 73) |
| TPS8 | AT1G70290 | GK-715G07 | GK715G07#LP TTCGTGATAGCCACTACC GTC (SEQ ID NO: 74) | GK715G07#RP ACAGAGTGGAGGTCAATG GTG (SEQ ID NO: 75) |
| TPS9 | AT1G23870 | SALK_063704 | SALK063704#LP CACACATTTGATTATGCA CGC (SEQ ID NO: 76) | SALK063704#RP GAGACTCCCATCCTCTTCC AC (SEQ ID NO: 77) |
| TPS10 | AT1G60140 | SALK_110873 | SALK110873#LP TTGCTCTCTTGCTCGATCT TC (SEQ ID NO: 78) | SALK110873#RP TGTCATGCTGCTGTAGAA TGC (SEQ ID NO: 79) |
| TPS11 | AT2G18700 | GK-592G12 | GK592G12#LP GACGTGTGCCACAAATTA TCC (SEQ ID NO: 80) | GK592G12#RP GTCGTGTACGCTCTCCAAT TC (SEQ ID NO: 81) |

After selecting the homozygous tps mutant plants, they were crossed with the esk1 mutant. The F1 plants were then sown to search for the double mutants. Thus the double mutants: tps5esk1, tps6esk1, tps8esk1, tps9esk1, tps10esk1 Tps11esk1 were selected in F2. Only the tps7esk1 mutant shows rosettes with larger size than those of the esk1 mutant as well as those of the other mutants (FIG. 6A).

Upon the selection of the single tps6 mutants (one of the close homologs of the TPS7 gene and of TPS5 (FIG. 6B) show a rosette size similar to that of the tps7 mutant. The selection of the tps6tps7 double mutant was therefore undertaken and a slightly larger surface of the rosettes was noted.

The expression profiles of the TPS genes of class 2 according to Ramon et al, 2009 and the very high homology between the protein sequences of the TPS5. TPS6 and TPS7 genes represented on the phylogenetic tree (FIG. 5), led to search for the tps6tps7esk1 triple mutants (FIGS. 6C and 6D). While the tps6esk1 double mutant does not suppress the dwarfism of the rosettes, it is suppressed with the triple combination and the surface of the rosettes even appears to be increased with a greater number of secondary inflorescences. This result suggests that there is an interaction between the TPS6 and TPS7 proteins that is capable in the context of the esk1 mutation of suppressing the "stress" effects that block the growth of the plants.

EXAMPLE 3: DETERMINATION IN THE CORN OF THE ORTHOLOG OF THE ATESK1 GENE

Materials and Methods

The research in the corn for the orthologs to the AtESK1 gene (ID of the AT3G55990 gene) was performed on the Plaza v.4 platform (Van Bel et al., 2017).

The CrispR cas9 targeting is done with the A oligo which targets Zm00001d022582 and is located at the end of the first of the exons. The B oligo mainly targets Zm00001d028751 (23/23) but also Zm00001d022582 (17/23; 3' end conserved). It is located in the exon1 of a total of 3 exons and is located upstream of the conserved region.

Oligo A = ESK3-CR85 in Zm00001d022582:
ACAGGTCGCACCCGGCAACCTGG

Oligo B = ESK6-CR24 in Zm00001d028751:
GCAGACGTGCGACCTGTACCGGG

Below are shown the primers used to target the Zm00001d028751(ESK3) and Zm00001d028751(ESK6) genes as well as the primers used for the PCR and the sequencing (Table 6).

TABLE 6

| | Primers used for crispR Cas 9 targeting | | Primers used for PCR amplification and sequencing | |
|---|---|---|---|---|
| ESK3-CR85-F | 5'-GCACAGGTCGCACCCGGCAACC 3' | ESK3#3F | 5'-CCTCCAGCTCAGCAACAACA-3' |
| ESK3-CR85-R | 5'-AACGGTTGCCGGGTGCGACCTG-3' | ESK3#3R | 5'-GTGGAGTAGTTGCTAGCGCA-3' |
| ESK6-CR24-F | 5'-TTGCAGACGTGCGACCTGTACC-3' | ESK6#2F | 5'-GTGACGCTCCCGACGGTGA-3' |
| ESK6-CR24-R | 5'-AACGGTACAGGTCGCACGTCTG-3' | ESK6#4R2 | 5'-GAAGGACGACCCCTGCTTCC-3' |

Obtaining and Selecting Mutants

The immature corn embryos of the A188 line were transformed via *Agrobacterium tumefaciens* by the L1657-ESK plasmid carrying between the left and right boundaries of the T-DNA, the CAS9 gene under the control of the Ubiquitin promoter, the oligos A and B and the BAR gene. The transformants obtained after the regeneration of the callus were grown and crossed with the A188 line used as maternal or paternal parent.

In the greenhouse (16 days photoperiod), 12 F1 plants of each crossing were grown. The presence or the absence of the BAR and CAS9 genes is determined by the presence or the absence of products of the PCR performed on the DNA of the F1 plants using the primers of the Table 6 above. The presence of heterozygous mutations in the target genes is verified by the sequencing of the PCR products and by using the software (Dehairs, J. et al. CRISP-ID: décodage des indels médiés par CRISPR par Sanger sequençage Sci. Rep. 6, 28973; doi: 10.1038/srep28973 (2016)). Negative plants for the BAR and CAS9 PCR products but heterozygous for the genes of interest were backcrossed onto A188 and self-fertilized plants. The F2 plants are then grown in the greenhouse, from which the homozygous mutant plants and the anizygous sister plants are selected by PCR and by Sanger PCR sequencing and again self-fertilized to produce a sufficient number of grains allowing the following analyses.

The F3 mutant plants (n=12) of each genotype and the wild type plants are grown in the greenhouse until the silage stage. The morphological characteristics such as the plant size, the length and the width of the 8th leaf are measured at the flowering and during the development of the plants. The number of ligulated leaves is reported over time.

At the silage stage, the whole plants with ear are cut, then batches of plants of the same genotype are coarsely crushed, bagged and weighed before being dehydrated by a passage for 96 hours in an oven at 50° C. The dry matter content is calculated by the difference in mass before and after the drying. The samples are then finely crushed with a hammer mill (1 mm grid) to a homogeneous powder.

Three batches of 3 plants of the same genotype constitute 3 biological replicates and a minimum of 2 technical replicates per analysis are performed.

Biochemical Analysis

Biochemical analyses are carried out on the powders after validation and calibration of the weightings. Prior to the extraction of the cell wall residues (CWR) by water/ethanol passages (Soxhlet), an amylase treatment is carried out on the dry matter powders. 2 g of dry matter is taken up in 20 ml of distilled water to which 400 µl of the amylase solution (HTL Ankom) is added. The tubes are incubated at 100° C. for 15 min with an agitation in the middle of the incubation. The tubes are then immersed in the ice to cool them down. A 15 min centrifugation at 18G is carried out, the supernatants are eliminated by aspiration and the pellets are rinsed twice with distilled water (20 ml) and centrifuged. The pellets are then frozen at −80° C. and lyophilized for 30 hours. The ponderal loss is estimated by weighing with 2 technical replicates per sample. The value is validated if less than 5% error between the repetitions and the values of the standards (Ronaldinio Z18DIgPE106 are consistent) (FIG. 9).

The digestibility of the In vitro dry matter (IVDMD) and the digestibility of the cell wall residues (IVCWRD) were estimated according to a modified protocol derived from Aufrère and Michalet-Doreau (1983). 30 mg of dry matter is pre-treated in an acid solution (0.1N HCl) at 40° C. for 24 h, and then a 2 M NaOH solution is added to terminate the reaction. The sample is then incubated in a cellulase solution (Cellulase Onozuka R10 8 mg·ml-1, 0.1M NaAc pH 4.95, 0.4% Na2CO3) at 50° C. for 72 h. After centrifugation, the pellet is washed with water and frozen before the lyophilization. The weight loss is expressed as a percentage of the initial weight (30 mg). The lignin content in the cell wall (KL.CWR) is estimated by the Kason method according to Dence (1992) (2 technical repetitions per sample, a third is performed if the results give more than 5% error).

The determination of the acetylation of the Xylan is carried out on a few micrograms of digested dry matter in a solution of endo-1,4-β-Xylanase (E-XYRU6, Megazyme) in 50 mM sodium acetate buffer previously desalted. The samples are then analysed and identified by MALDI-TOF mass spectrometry.

The preparation of the histological sections and the statistical analyses were performed according to the protocols described in the publication (Legland et al., 2017).

Statistical Treatments

The statistical analyses of the data are performed in Excel or with the RStudio software.

Results

By bioinformatics analysis using the PLAZA v.4 software, two candidate genes Zm00001d028751 and Zm00001d022582 were selected as the best candidates ortholog to the AtESK1 (AT1G55990) gene in *Arabidopsis*. It appeared interesting to perform directly the double genetic targeting by the CrispR cas9 strategy to quickly validate if these candidates were the right ones, given the very high homology with the other orthologous genes belonging to the family of the TBL29.

FIG. 7 shows the A oligo which targets the Zm00001d022582 (ESK3) gene and is located at the end of the first exon, and the B oligo which mainly targets Zm00001d028751 (ESK6) (23/23) but also Zm00001d022582 (17/23; 3' end conserved). It is located in the exon1 on a total of 3 exons.

The corn transformants obtained by T-DNA transformation were analysed by sequencing and thus several allelic mutants were obtained (Table 7). By backcrossing with the wild type line, it was possible to select esk3 and esk6 allelic single mutants as well as esk3esk6 allelic double mutants in the segregating progeny.

TABLE 7

Description of the mutations obtained in each studied gene

| Transformant name | Gene targeting | Mutant name | Mutation type | Sequences |
|---|---|---|---|---|
| — | Zm00001d022582 | — | no | CCCCAGGTTGCCGGGTGCGACC |
| W451-1 | Zm00001d022582 | esk3.1 | 5 bp deletion (CCGGG) | CCCCAGGTTGTGCCACC |
| W451-2 | Zm00001d022582 | esk3.2 | 1 bp ins: A | CCCCAGGTATGCCGGGTGCGACC |

TABLE 7-continued

Description of the mutations obtained in each studied gene

| Transformant name | Gene targeting | Mutant name | Mutation type | Sequences |
|---|---|---|---|---|
| — | Zm00001d028751 | — | no | CCGCAGACGTGCGACCTGTACC |
| W451-1 | Zm00001d028751 | esk6.1 | 1 bp ins: A | CCGCACACGTGCGACCTGTAACC |
| W450-2 et W451-2 | Zm00001d028751 | esk6.2 | 1 bp ins: T | CCGCAGACGTGCGACCTGTTACC |
| W451-1 | Zm00001d028751 | esk6.3 | 2 bp ins: GT | CCGCAGACGTGCGACCTACC |
| w450-1 | Zm00001d028751 | esk6.4 | 6 bp del | CCGCAGACGTGCGACCTGT |

The morphological and biochemical characterizations focused on two of the 4 allelic mutants of the Zm00001d028751 gene. These are the esk6.1 mutant whose the mutation creates a STOP codon resulting in a truncated protein of 192 amino acids out of the total 555, and the esk6.2 mutant whose the mutation leads to a change in the reading phase from the amino acid 192 to the 308*, thus leading to a truncated protein of 247 amino acids.

For the Zm00001d022582 gene, only two allelic mutants were obtained, these are the esk3.1 and esk3.2 mutants, whose the mutations create a change in reading phase from the amino acid 158 and to truncated proteins of size 223 and 225 amino acids respectively out of the predicted 529 amino acids. The esk3.1esk6.1 and esk3.2esk6.2 double mutants were also studied in this study.

The culture of all the mutant and wild type plants allowed to show that the plants carrying the esk6 mutation were 27% smaller in size compared to that of the wild type plants (FIGS. 8A and 8C). The length and the width of the longest leaf are also impacted with a decrease in the surface area of 20 and 27% respectively (FIG. 8D). A growth delay of about 3 weeks is also observed in all the plants carrying the esk6 mutation (FIG. 8B). In contrast, the plants carrying the esk3 mutation are not different from the wild type plants (FIGS. 8A and 8C). The esk3esk6 double mutants are also dwarfed, indicating a high penetrance of the mutation (FIGS. 8A and 8C). Like the esk6 single mutants, the borders and the tips of the leaves of the esk3esk6 double mutants turn yellow or dry out from the 4$^{th}$ leaf onwards.

At the silage stage, determined after observation of the maturation of the grains located in the middle of the ear (pasty, vitreous, milky stage), the batches of plants of the same genotype (3 batches) were harvested and the dry matter percentages indicate that the plants were collected at the same stage of maturity with values that vary between 30 and 37% depending on the batches (Table 8).

TABLE 8

Percentage of dry matter of the whole plants harvested at the silage stage.

| Genotype | Nb of plants | Nb of batches | % Dry matter | Standard deviation |
|---|---|---|---|---|
| esk3.1 | 9 | 3 | 29.48 | 0.77061 |
| esk3.2 | 10 | 4 | 31.12 | 1.02156 |
| esk6.1 | 8 | 3 | 34.80 | 3.70416 |
| esk6.2 | 9 | 3 | 32.26 | 1.93718 |
| esk3.1esk6.1 | 9 | 3 | 36.99 | 3.35735 |
| esk3.2esk6.2 | 4 | 2 | 30.89 | 1.07737 |
| WT | 8 | 3 | 31.97 | 0.18798 |

The analysis of the oligoxylans shows that only the esk61 and esk6.2 allelic mutants have a decrease in Xyl6 Ac2, Xyl6 Ac3, Xyl6 Ac4 and a very significant increase in Xyl4(Glc4Me)Ac (FIG. 10). In contrast, the esk3 allelic single mutants and the esk3esk6 double mutants have oligoxylans little different from those of the wild type plants.

From these results, it can be concluded that the Zm00001d028751 (ESK6) gene is the ortholog of the At1G55990 gene and has a Xylan O-Acetyl transferase function.

The dwarfism observed in all the plants carrying the esk6 mutation, single or double mutant, shows the penetrance of the mutation. According to these results, the Zm00001d022582 (ESK3) gene has no function involved in the acetylation of the xylans.

Improvement of the Biomass Digestibility by the Esk6 Mutation.

All the plants carrying the esk6 mutation (single and double mutants) have a better digestibility of the dry matter (INDMD) of 2 to 4% depending on the genotypes compared to the wild type plants. The plants carrying the esk3 single mutation are poorly digestible compared to the wild type plants (from −2 to −4%) and strongly less digestible compared to the esk6 mutants and the esk3esk6 double mutants (from −5 to −8%) (FIG. 11A).

The analysis of the results of the digestibility of the parietal residue (INCWRD) also show the same results with clearly an improvement in the digestibility of the biomass in the plants carrying the esk6 mutation as indicated by the Tukey statistical test in FIG. 11A. This digestibility is improved by 3 to 4 points depending on the genotypes.

The Content, the Composition and the Structure of the Lignin are Unchanged in the Mutants.

To determine whether the improvement of the digestibility of the biomass of the mutants is related to a lower lignin content, the lignin was quantified by the Klason method on the parietal residues. The contents vary extremely little from 13.8 to 14.9% (FIG. 11B). The distribution of the genotypes according to the IVCWRD and the Klason lignin content shows two distinct groups of plants. The first group consists of all the mutants carrying the esk6 mutants (single and double mutants) and the second the esk3 single mutants and the wild type plants (FIG. 11C). This result indicates that at equivalent lignin content, the esk6 and esk3esk6 mutant plants are much more digestible.

To find out whether this digestibility is related to a change in the composition and the structure of the lignins, a thioacidolysis was performed on the esk6 single mutants and the esk3esk6 double mutants.

The results (not presented here) indicate that there is no change in the composition and the structure of the lignins of the mutants compared to the wild type control.

The Esk6 Mutation Acts on the Size of the Internodes and the Production of a Less Lignified Medullary Parenchyma.

FIG. 12A shows sections of corn stem internodes after staining with Fasga. It can be observed that the plants carrying the esk6 mutation have reduced internode surfaces compared to those of the wild type and esk3 mutant plants. Moreover, a more pronounced blue coloration of the marrow in the esk6 and esk3esk6 mutants indicates that the cells of the medullary parenchyma are less lignified than those of the wild type and esk3 mutant plants, which have a pink parenchyma and are therefore more lignified. The blue staining of the perivascular cells of the esk6 mutant (FIG. 12B) indicates that they are poorly lignified and they appear to be larger in size compared to those of the wild type. These observations are confirmed by the statistical treatment of the internode sections (n=57) (FIG. 13). It shows that the esk6 and esk3esk6 mutants have a significant reduction in the surface of the internodes. Also, the latter have significantly less lignified tissue and a higher proportion of non-lignified tissue. However, the statistical analysis did not reveal any significant difference concerning the thickness of the bark and the surface of the vascular vessels.

Given the biochemical results on the lignin contents, this suggests a different spatial distribution of the lignins within the tissues.

Conclusion

The Zm00001d028751 gene is the ortholog of the AT1G55990 gene in arabidopsis. It leads to the same developmental defect, i.e. the dwarfism of the plants, and is accompanied with a better digestibility of the biomass resulting from a decrease in the acetylation of the xylans. The vascular vessels of the mutant are not collapsed as in the arabidopsis Ateskl mutant. Furthermore, the observations of several hundred histological sections of corn internodes derived from plants grown under water stress conditions never allowed the collapse of the xylem vessels to be observed, but the same pattern of distribution of the tissues observed in the esk6 mutant.

EXAMPLE 4: CHARACTERIZATION OF THE ESK1 AND TPS7 DOUBLE MUTANT PLANTS IN THE CORN

1. Research of the in Silico Orthologs in the Corn from the *Arabidopsis thaliana* Plants On the website
https://bioinformatics.psb.ugent.be/plaza/versions/plaza_v4_monocots/,
- in the research engine, entering the name of the ESK1 gene in *Arabidopsis thaliana*, namely AT3G55990,
- in the "Toolbox, explore" section, selecting the "the orthologs using the Integrative Orthology Viewer" tab,
- selecting for the "*Zea Mays*" species the ortholog corresponding to the "Best-Hits-and-Inparalogs(BHI)family", in this case Zm00001d028751,
- in the "Toolbox, view" section, selecting the "sequences" tab.

The nucleotide and protein sequences of Zm00001d028751 are then accessible.

For the TPS7 gene, the operation is repeated with the name of the TPS7 gene in *Arabidopsis thaliana*, i.e. AT1G06410, and the ortholog in the corn is found, under the reference Zm00001d043469.

1.1. Verifying the Presence of the Conserved Patterns in the Corn Orthologs

A protein alignment between the *Arabidopsis thaliana* sequence and that of the *Zea Mays* is performed using the website https://www.ebi.ac.uk/Tools/psa/emboss_needle/.

The presence of the GDSL pattern, present in the acyl-esterase domain of the ESK1 protein is confirmed directly from this sequence alignment.

The presence of a transmembrane domain is identified via the TMHMM bioinformatics tool, accessible from the website http://www.cbs.dtu.dk/services/TMHMM/

1.2. Obtaining the Corn Mutants

There are 2 orthologous genes for the ESK1 gene (AT3G55990) in the corn: Zm00001d022582 and Zm00001 d028751.

Genetic transformations of A188 immature corn embryos are performed with the L1657-ESK plasmid (FIG. 4) carrying between the borders of the T-DNA the gene encoding the CAS9 protein under the control of the Ubiquitin promoter as well as the target sequences of the genes of interest. For the Zm00001d022582 and Zm00001d028751 genes, the target sequences are CAGGTCGCACCCGGCAACC and CAGACGTGCGACCTGTACC, respectively.

There are 3 orthologous genes for the TPS7 gene (AT1G06410) in the corn: ZM03G31920 (ZmTprs7), ZM03G31900 (ZmTprsS6) and ZM08G34940 (ZmTPrs15) in the corn. For the ZM03G31900 gene, there are mutator transposon insertions such as mu1069747 in UFMu-08325 and mu1077018 in UFMu-08873 and for the ZM08G34940 gene, there is only one insertion of a transposable element in the exonic part: this is mu1057945 in the UFMu-07357 line. For the ZM03G31920 gene, which is the closest ortholog of AtTPS7, there is no transposable element in the gene. A CRISPR/Cas9 mutagenesis strategy is then required.

2. Materials and Methods

The esk1 tps7 double mutants as well as the single mutants and the wild type are grown in a greenhouse or dedicated platform. All informative morphometric and phenological characteristics such as the date of appearance of the third ligulated leaf, date of flowering, plant height, width and length of the longest leaf are measured.

The plants are collected at the silage stage and at the mature grain stage. The water content of the stems and the leaves is evaluated by weighing them before and after drying in an oven at 50° C. for 4 days. The dry biomass is crushed to a fine powder with an IKA M20 knife mill.

The biomass of the different lines is characterized as follows:

1/The digestibility by enzymatic hydrolysis (Virlouvet et al., in preparation).

3 technical replicates per sample are performed.

30 mg of dry matter is incubated 24 h at 40° C. in the presence of HCL0,1N and then 90 µl of 2M soda is added. After vortexing the mixture, 2 ml of cellulolysis solution (NaAc 0.1M pH 4.95, 0.4% Sodium azide, Cellulase ONOZUKA R10 8 mg·ml-1) is added. The whole is placed under agitation at 50° C. for 72 hours. The tubes are centrifuged for 15 min at 4000 RPM 8° C., the supernatants are eliminated and 4 ml of water is added to wash the pellets. After vortexing the pellets, a new centrifugation is performed for 10 minutes. A new rinse with water and centrifugation are performed and the supernatant is then eliminated. The pellets are frozen at −80° C. before lyophilization for at least 48 hours. The dry pellets are then weighed. The ponderal loss is calculated as a percentage.

2/The acetate level according to the recommendations of the kit of K-Acetic acid of Megazyme from 25 mg of parietal residues obtained by the Soxhlet method.

3/ The sugar content of 10 mg of non-cellulosic parietal residues obtained after a treatment with 2.5M Trifluoroacetic acid (TFA). The analysis is carried out by HPLC compared to the reference sugars (D(+)-Fucose, D(+)-Arabinose, D(+)-Glucose, D(+)-Galactose, D(+)-Mannose, D(+)-D(+)-Xylose, L-Rhamnose, D(−)-Fructose.

The dosing of the trehalose-6-phosphate and the trehalose is carried out by chemical analysis.

4/ Cytological observations of the xylem vessels (internodes under the ear) and the roots are performed under light microscopy.

The lignin levels by the Klason lignin method from 150 mg of parietal residues according to the protocol described by Méchin et al., 2014.

At silage stage, the acquisition of Fourier transform infrared spectra (FTIR) obtained from xylem tissues on internode sections under the ear of 50 µm allows the highlighting of the acetylation of the xylans (Lefebre et al., 2011).

Fasga histological staining of the internodes under ear allow to visualize the lignified and non-lignified tissues, the shape of the vessels as well as their density (Legland et al., 2017).

EXAMPLE 5: CHARACTERIZATION OF THE ESK1, TPS7 AND KAK TRIPLE MUTANT PLANTS IN THE CORN

1. Research of the in Silico Orthologs in the Corn from the *Arabidopsis thaliana* Plants The research for the ortholog of the KAK gene in the corn is performed as described in Example 2 with the name of the KAK gene in *Arabidopsis thaliana*, namely AT4G38600 and the ortholog in the corn is found under the reference Zm00001d004139.

There are 2 genes ortholog for the KAK gene (AT4G38600) in the corn: Zm00001d004139 (ZmKak1) and Zm00001d014920 (ZmKak2).

Homozygous plants for mutation in the ZmKak2 gene were obtained by insertion of a mutator transposon: mu1057066 in the UFMu-07383 line. Concerning the ZmKak1 gene, a CRISPR/Cas9 mutagenesis strategy is more suitable.

2. Materials and Methods

The esk1 tps7 double mutants are crossed with the esk1 kak double mutants. The progeny of the F1 plants (homozygous esk, heterozygous tps7, heterozygous kak) are grown to produce a F2 progeny by self-fertilization. Among the F2 plants, 1/16th of the plants are esk tps7 kak triple mutants. The selection of the plants is done by PCR genotyping with the primers used to select the single mutants.

The same studies as described in Example 2 are conducted.

BIBLIOGRAPHY

Abe et al., Nature Biotechnology, 2012, 30, pages 174-178;
Anantharaman et al., Biology Direct, 2010, 5:1, pages 1-8;
Bhatia et al., Plant Biotechnol Journal, 2017, 15:1071-1092;
Bensussan et al., Plant Physiology, 2015, DOI: 10.1104/pp. 15.00122;
Char et al., Plant Biotechnol J, 2017, 15, 257-268;
Colbert et al., Plant Physiology, 2001, 126, pages 480-484;
El Refy et al., Mol Gen Genomics, 2003, 270, pages 403-414;
Feng et al., Cell Res, 2013, 23, pages 1229-1232;
Gille et al., Plant Science, 2012, 3, pages 1-7;
Hartwig et al., Plant Physiology, 2012, pages 591-600;
Henikoff et. al., Annual Review of Plant Biology, 2003, 54, pages 15.1-15.27;
Kalluri et al., Plant Biotechnol Journal, 2014, 12(9), pages 1207-1216;
Lefebvre et al., PLoS ONE, 2011, 6:2, pages 1-13;
Legland et al., Plant Methods, 2017, 13:84;
Lunn et al., Plant Journal, 2014, 79, 544-567;
McCallum et al., Plant Physiology, 2000, 123:2, pages 439-442;
McCarty et al., Plant Transposable Elements, 2013, 157-166;
Méchin et al., J. Agric. Food Chem. 2014, 62: 5102-5107;
Mi et al., Nucleic Acids Research, 2017, 45, pages D183-D189;
Mottiar et al., Curr Opin Biotechnol, 2016, 37:190-200;
O'Hara et al., Molecular Plant, 2013, 6, pages 261-274;
Paul et al., Plant Physiology, 2018, 177, pages 12-23;
Ramon et al., Plant, Cell and environment, 2009, 32 pages 1015-1032;
Shan et al., Nat. Biotechnol, 2013, 31, pages 686-688;
Sharma et al., Frontiers in plant science, 2016, 6, pages 1-15;
Sims et al., Bioresour Technol, 2010, 101, 1570-1580;
Svitashev et al., Plant. Physiol., 2015, 169, 931-945;
Taheri et al., Mol Breeding., 2017, 169, 931-945;
Till et al., Genome research, 2003, 13, DOI: 10.1007/s11032-017-0643-7;
Tisne et al., Plant Journal, 2013, 74, pages 534-544;
Van Bel et al. (2017) PLAZA 4.0: an integrative resource for functional, evolutionary and comparative plant genomics Nucleic Acids Res;
Vandesteene et al., Plant Physiology, 2012, 160, 884-896;
Virlouet L et al. Front Plant Sci. 2019; 10: 488. doi: 10.3389/fpls.2019.00488
Xin et al., PNAS, 1998, 95, pages 7799-7804;
Yang et al., Plant Biotechnology journal, 2012, pages 1-11;
Yuan et al., 2013, Plant & Cell Physiology, pages 1-14.

The invention claimed is:

1. A plant obtained by a mutagenesis method comprising decreasing the expression and/or the activity
of the protein designated ESK1 and
of the protein designated TPS7,
in said plant, as compared to a non-mutagenized parent plant, and the decrease in the expression and/or the activity of the ESK1 and TPS7 proteins is achieved by introducing at least one mutation in each of the genes encoding the ESK1 and TPS7 proteins in said plant, and such that:
the non-mutagenized ESK1 protein has at least 50% identity with the sequence SEQ ID NO: 1 and comprising the acyl esterase and transmembrane domains, and
the non-mutagenized TPS7 protein has at least 60% identity with the sequence SEQ ID NO: 2 and comprising the TPS and TPP domains.

2. The plant according to claim 1, wherein the decrease in the expression and/or the activity of the KAK protein, as compared to a non-mutagenized parent plant, is achieved by introducing at least one mutation in the gene encoding the KAK protein, and such that the non-mutagenized KAK protein has at least 60% identity with the sequence SEQ ID NO: 3 and comprising the armadillo replicates and a HECT domain.

3. The plant according to claim 1, wherein the decrease in the expression and/or the activity of the TPS6 protein, as compared to a non-mutagenized parent plant, is achieved by introducing at least one mutation in the gene encoding the TPS6 protein, and such that the non-mutagenized TPS6 protein has at least 60% identity with the sequence SEQ ID NO: 6S and comprises the TPS and TPP domains.

4. A method for preparing a plant according to claim 1 with improved digestibility comprising the steps of mutagenesis of the genes encoding the proteins designated ESK1 and TPS7.

5. The method according to claim 4, comprising an additional step of mutagenesis of the gene encoding the protein designated KAK.

6. The method according to claim 4, comprising an additional step of mutagenesis of the gene encoding the protein designated TPS6.

7. A method for increasing the growth of a plant carrying the esk1 mutation, comprising a step of genetically modifying said plant to decrease the expression and/or the activity of the protein designated TPS7.

8. The method for increasing the growth of a plant carrying the esk1 mutation according to claim 7, comprising an additional step of genetically modifying said plant to decrease the expression and/or the activity of the protein designated KAK.

9. The method for increasing the growth of a plant carrying the esk1 mutation according to claim 7, comprising an additional step of genetically modifying said plant to decrease the expression and/or the activity of the protein designated TPS6.

* * * * *

SEQUENCE LISTING

```
<160> NUMBER OF SEQ ID NOS: 81

<210> SEQ ID NO 1
<211> LENGTH: 487
<212> TYPE: PRT
<213> ORGANISM: Arabidopsis thaliana

<400> SEQUENCE: 1

Met Gln Pro Trp Arg Arg Lys Phe Pro Leu Phe Glu Thr Gly Val Thr
1               5                   10                  15
```

-continued

```
Met Lys Gln Arg Lys Asn Ser Asn Leu Ser Ile Phe Val Val Phe
             20                  25                  30
Ser Val Phe Leu Phe Gly Ile Phe Met Tyr Asn Glu Asp Val Lys Ser
             35                  40                  45
Ile Ala Glu Phe Pro Phe Ser Thr Ser Lys Pro His Asp Val His Asp
50                   55                  60
Glu Ala Thr Pro Ile Thr Glu Ile Thr Thr Leu Pro Val Gln Glu Ser
65                   70                  75                  80
Ile Lys Asn Ser Asp Pro Ile Gln Glu Ser Ile Lys Asn Ala Asp Ser
             85                  90                  95
Val Gln Asp Ser Val Lys Asp Val Ala Glu Pro Val Gln Glu Glu Val
             100                 105                 110
Ser Lys Thr Glu Glu Val Lys Lys Ile Glu Leu Phe Ala Ala Thr Glu
             115                 120                 125
Asp Glu Glu Asp Val Glu Leu Pro Pro Glu Glu Cys Asp Leu Phe Thr
             130                 135                 140
Gly Glu Trp Val Phe Asp Asn Glu Thr His Pro Leu Tyr Lys Glu Asp
145                  150                 155                 160
Gln Cys Glu Phe Leu Thr Ala Gln Val Thr Cys Met Arg Asn Gly Arg
                 165                 170                 175
Arg Asp Ser Leu Tyr Gln Asn Trp Arg Trp Gln Pro Arg Asp Cys Ser
             180                 185                 190
Leu Pro Lys Phe Lys Ala Lys Leu Leu Glu Lys Leu Arg Asn Lys
             195                 200                 205
Arg Met Met Phe Val Gly Asp Ser Leu Asn Arg Asn Gln Trp Glu Ser
210                  215                 220
Met Val Cys Leu Val Gln Ser Val Pro Pro Gly Arg Lys Ser Leu
225                  230                 235                 240
Asn Lys Thr Gly Ser Leu Ser Val Phe Arg Val Glu Asp Tyr Asn Ala
                 245                 250                 255
Thr Val Glu Phe Tyr Trp Ala Pro Phe Leu Val Glu Ser Asn Ser Asp
                 260                 265                 270
Asp Pro Asn Met His Ser Ile Leu Asn Arg Ile Ile Met Pro Glu Ser
             275                 280                 285
Ile Glu Lys His Gly Val Asn Trp Lys Gly Val Asp Phe Leu Val Phe
             290                 295                 300
Asn Thr Tyr Ile Trp Trp Met Asn Thr Phe Ala Met Lys Val Leu Arg
305                  310                 315                 320
Gly Ser Phe Asp Lys Gly Asp Thr Glu Tyr Glu Glu Ile Glu Arg Pro
                 325                 330                 335
Val Ala Tyr Arg Arg Val Met Arg Thr Trp Gly Asp Trp Val Glu Arg
                 340                 345                 350
Asn Ile Asp Pro Leu Arg Thr Thr Val Phe Phe Ala Ser Met Ser Pro
             355                 360                 365
Leu His Ile Lys Ser Leu Asp Trp Glu Asn Pro Asp Gly Ile Lys Cys
             370                 375                 380
Ala Leu Glu Thr Thr Pro Ile Leu Asn Met Ser Met Pro Phe Ser Val
385                  390                 395                 400
Gly Thr Asp Tyr Arg Leu Phe Ser Val Ala Glu Asn Val Thr His Ser
                 405                 410                 415
Leu Asn Val Pro Val Tyr Phe Leu Asn Ile Thr Lys Leu Ser Glu Tyr
             420                 425                 430
Arg Lys Asp Ala His Thr Ser Val His Thr Ile Arg Gln Gly Lys Met
```

```
                    435                 440                 445
Leu Thr Pro Glu Gln Gln Ala Asp Pro Asn Thr Tyr Ala Asp Cys Ile
    450                 455                 460

His Trp Cys Leu Pro Gly Leu Pro Asp Thr Trp Asn Glu Phe Leu Tyr
465                 470                 475                 480

Thr Arg Ile Ile Ser Arg Ser
                485

<210> SEQ ID NO 2
<211> LENGTH: 851
<212> TYPE: PRT
<213> ORGANISM: Arabidopsis thaliana

<400> SEQUENCE: 2

Met Ile Ser Arg Ser Tyr Thr Asn Leu Leu Asp Leu Ala Ser Gly Asn
1               5                   10                  15

Phe Pro Val Met Gly Arg Glu Arg Arg Leu Pro Arg Val Met Thr
                20                  25                  30

Val Pro Gly Asn Val Ser Glu Phe Asp Glu Asp Gln Ala Tyr Ser Val
            35                  40                  45

Ser Ser Asp Asn Pro Ser Val Ser Ser Asp Arg Met Ile Ile Val
    50                  55                  60

Ala Asn Arg Leu Pro Leu Lys Ala Glu Lys Arg Asn Gly Ser Trp Ser
65                  70                  75                  80

Phe Ser Trp Asp Gln Asp Ser Leu Tyr Leu Gln Leu Lys Asp Gly Leu
                85                  90                  95

Pro Glu Asp Met Glu Ile Leu Tyr Val Gly Ser Leu Ser Val Asp Val
                100                 105                 110

Asp Ser Asn Glu Gln Asp Val Ala Gln Ile Leu Leu Asp Lys Phe
        115                 120                 125

Lys Cys Val Pro Thr Phe Phe Pro Asp Leu Gln Ser Lys Phe Tyr
    130                 135                 140

Asp Gly Phe Cys Lys Arg Gln Ile Trp Pro Leu Phe His Tyr Met Leu
145                 150                 155                 160

Pro Phe Ser Ala Asp His Gly Gly Arg Phe Asp Arg Ser Leu Trp Glu
                165                 170                 175

Ala Tyr Val Ala Thr Asn Lys Leu Phe Phe Gln Lys Val Ile Glu Val
                180                 185                 190

Ile Asn Pro Asp Asp Asp Phe Val Trp Ile His Asp Tyr His Leu Met
            195                 200                 205

Val Leu Pro Thr Phe Leu Arg Arg Arg Phe Asn Arg Ile Arg Met Gly
    210                 215                 220

Phe Phe Leu His Ser Pro Phe Pro Ser Ser Glu Ile Tyr Arg Ser Leu
225                 230                 235                 240

Pro Val Arg Glu Glu Ile Leu Lys Ala Leu Leu Asn Ser Asp Leu Ile
                245                 250                 255

Gly Phe His Thr Phe Asp Tyr Ala Arg His Phe Leu Thr Cys Cys Ser
                260                 265                 270

Arg Met Leu Gly Leu Glu Tyr Gln Ser Lys Arg Gly Tyr Ile Gly Leu
        275                 280                 285

Glu Tyr Tyr Gly Arg Thr Val Gly Ile Lys Ile Met Pro Val Gly Ile
    290                 295                 300

Asn Met Gly Arg Ile Gln Ser Val Met Arg Tyr Ser Glu Glu Glu Gly
305                 310                 315                 320
```

```
Lys Val Met Glu Leu Arg Asn Arg Phe Glu Gly Lys Thr Val Leu Leu
                325                 330                 335

Gly Ile Asp Asp Met Asp Ile Phe Lys Gly Ile Asn Leu Lys Leu Leu
                340                 345                 350

Ala Met Glu Gln Met Leu Arg Gln His Pro Asn Trp Arg Gly Arg Ala
                355                 360                 365

Val Leu Val Gln Ile Val Asn Pro Ala Arg Gly Lys Gly Ile Asp Val
                370                 375                 380

Glu Glu Ile Arg Gly Glu Ile Glu Glu Ser Cys Arg Arg Ile Asn Gly
385                 390                 395                 400

Glu Phe Gly Lys Pro Gly Tyr Gln Pro Ile Ile Tyr Ile Asp Thr Pro
                405                 410                 415

Val Ser Ile Asn Glu Ile Asn Ala Tyr Tyr His Ile Ala Glu Cys Val
                420                 425                 430

Val Val Thr Ala Val Arg Asp Gly Met Asn Leu Thr Pro Tyr Glu Tyr
                435                 440                 445

Ile Val Cys Arg Gln Gly Leu Leu Gly Ser Glu Ser Asp Phe Ser Gly
                450                 455                 460

Pro Lys Lys Ser Met Leu Val Ala Ser Glu Phe Ile Gly Cys Ser Pro
465                 470                 475                 480

Ser Leu Ser Gly Ala Ile Arg Val Asn Pro Trp Asn Val Glu Ala Thr
                485                 490                 495

Gly Glu Ala Leu Asn Glu Ala Leu Ser Met Ser Asp Ala Glu Lys Gln
                500                 505                 510

Leu Arg His Glu Lys His Phe Arg Tyr Val Ser Thr His Asp Val Ala
                515                 520                 525

Tyr Trp Ser Arg Ser Phe Leu Gln Asp Leu Glu Arg Ile Cys Val Asp
                530                 535                 540

His Phe Lys Lys Arg Cys Trp Gly Met Gly Ile Ser Phe Gly Phe Arg
545                 550                 555                 560

Val Val Ala Leu Asp Pro Asn Phe Arg Lys Leu Ser Ile Pro Cys Ile
                565                 570                 575

Val Ser Asp Tyr Lys Arg Ala Lys Ser Arg Ala Ile Leu Leu Asp Tyr
                580                 585                 590

Asp Gly Thr Leu Met Pro Gln Asn Ser Ile Asn Lys Ala Pro Ser Gln
                595                 600                 605

Glu Val Leu Asn Phe Leu Asp Ala Leu Cys Glu Asp Lys Lys Asn Ser
                610                 615                 620

Ile Phe Ile Val Ser Gly Arg Gly Arg Glu Ser Leu Ser Lys Trp Phe
625                 630                 635                 640

Thr Pro Cys Lys Lys Ile Gly Ile Ala Ala Glu His Gly Tyr Phe Leu
                645                 650                 655

Lys Trp Ser Gly Ser Glu Glu Trp Glu Thr Cys Gly Gln Ser Ser Asp
                660                 665                 670

Phe Gly Trp Met Gln Ile Val Glu Pro Val Met Lys Gln Tyr Thr Glu
                675                 680                 685

Ser Thr Asp Gly Ser Ser Ile Glu Ile Lys Glu Ser Ala Leu Val Trp
                690                 695                 700

Gln Tyr Arg Asp Ala Asp Pro Gly Phe Gly Ser Leu Gln Ala Lys Glu
705                 710                 715                 720

Met Leu Glu His Leu Glu Ser Val Leu Ala Asn Glu Pro Val Ala Val
                725                 730                 735

Lys Ser Gly His Tyr Ile Val Glu Val Lys Pro Gln Gly Val Ser Lys
```

```
                740                 745                 750
Gly Ser Val Ser Glu Lys Ile Phe Ser Ser Met Ala Gly Lys Gly Lys
            755                 760                 765

Pro Val Asp Phe Val Leu Cys Ile Gly Asp Asp Arg Ser Asp Glu Asp
770                 775                 780

Met Phe Glu Ala Ile Gly Asn Ala Met Ser Lys Arg Leu Leu Cys Asp
785                 790                 795                 800

Asn Ala Leu Val Phe Ala Cys Thr Val Gly Gln Lys Pro Ser Lys Ala
                805                 810                 815

Lys Tyr Tyr Leu Asp Asp Thr Thr Glu Val Thr Cys Met Leu Glu Ser
                820                 825                 830

Leu Ala Glu Ala Ser Glu Ala Ser Asn Phe Ser Met Arg Glu Leu Asp
            835                 840                 845

Glu Ala Leu
    850

<210> SEQ ID NO 3
<211> LENGTH: 1888
<212> TYPE: PRT
<213> ORGANISM: Arabidopsis thaliana

<400> SEQUENCE: 3

Met Glu Thr Arg Ser Arg Lys Arg Ala Glu Ala Thr Ser Ala Ala Pro
1               5                   10                  15

Ser Ser Ser Ser Ser Ser Pro Pro Pro Pro Ser Ala Ser Gly Pro
            20                  25                  30

Thr Thr Arg Ser Lys Arg Ala Arg Leu Ser Ser Ser Ser Ser Ser
            35                  40                  45

Leu Ala Pro Thr Pro Pro Ser Ser Ser Thr Thr Thr Arg Ser Arg Ser
50                  55                  60

Ser Arg Ser Ala Ala Ala Ala Pro Met Asp Thr Ser Thr Asp Ser
65                  70                  75                  80

Ser Gly Phe Arg Arg Gly Gly Arg Gly Asn Arg Gly Asn Asn Asn Asp
                85                  90                  95

Asn Ser Asp Lys Gly Lys Glu Lys Glu His Asp Val Arg Ile Arg Glu
                100                 105                 110

Arg Glu Arg Glu Arg Asp Arg Ala Arg Glu Gln Leu Asn Met Asp Ala
            115                 120                 125

Ala Ala Ala Ala Ala Arg Ser Ala Asp Glu Asp Asp Asn Asp Ser
        130                 135                 140

Glu Asp Gly Asn Gly Gly Phe Met His Pro Asn Met Ser Ser Ala Ser
145                 150                 155                 160

Ser Ala Leu Gln Gly Leu Leu Arg Lys Leu Gly Ala Gly Leu Asp Asp
                165                 170                 175

Leu Leu Pro Ser Ser Gly Ile Gly Ser Ala Ser Ser Ser His Leu Asn
                180                 185                 190

Gly Arg Met Lys Lys Ile Leu Ser Gly Leu Arg Ala Glu Gly Glu Glu
            195                 200                 205

Gly Lys Gln Val Glu Ala Leu Thr Gln Leu Cys Glu Met Leu Ser Ile
    210                 215                 220

Gly Thr Glu Asp Ser Leu Ser Thr Phe Ser Val Asp Ser Phe Val Pro
225                 230                 235                 240

Val Leu Val Gly Leu Leu Asn His Glu Ser Asn Pro Asp Ile Met Leu
                245                 250                 255
```

```
Leu Ala Ala Arg Ala Leu Thr His Leu Cys Asp Val Leu Pro Ser Ser
            260                 265                 270

Cys Ala Ala Val Val His Tyr Gly Ala Val Ser Cys Leu Val Ala Arg
        275                 280                 285

Leu Leu Thr Ile Glu Tyr Met Asp Leu Ala Glu Gln Ser Leu Gln Ala
    290                 295                 300

Leu Lys Lys Ile Ser Gln Glu His Pro Thr Ala Cys Leu Arg Ala Gly
305                 310                 315                 320

Ala Leu Met Ala Val Leu Ser Tyr Leu Asp Phe Phe Ser Thr Gly Val
                325                 330                 335

Gln Arg Val Ala Leu Ser Thr Ala Ala Asn Met Cys Lys Lys Leu Pro
            340                 345                 350

Ser Asp Ala Ser Asp Tyr Val Met Glu Ala Val Pro Leu Leu Thr Asn
        355                 360                 365

Leu Leu Gln Tyr His Asp Ser Lys Val Leu Glu Tyr Ala Ser Ile Cys
    370                 375                 380

Leu Thr Arg Ile Ala Glu Ala Phe Ala Pro Tyr Pro Glu Lys Leu Asp
385                 390                 395                 400

Glu Leu Cys Asn His Gly Leu Val Thr Gln Ala Ala Ser Leu Ile Ser
                405                 410                 415

Thr Ser Asn Ser Gly Gly Gln Ala Ser Leu Ser Val Ser Thr Tyr
            420                 425                 430

Thr Gly Leu Ile Arg Leu Leu Ser Thr Cys Ala Ser Gly Ser Pro Leu
        435                 440                 445

Gly Phe Arg Thr Leu Leu Leu Gly Ile Ser Ser Ile Leu Lys Asp
    450                 455                 460

Ile Leu Leu Gly Ser Gly Val Ser Ala Asn Ala Ser Val Ser Pro Ala
465                 470                 475                 480

Leu Ser Arg Pro Ala Asp Gln Ile Tyr Glu Ile Val Asn Leu Ala Asn
                485                 490                 495

Glu Leu Leu Pro Pro Leu Pro Glu Gly Val Ile Ser Leu Pro Thr Ser
            500                 505                 510

Thr Asn Ala Leu Val Lys Gly Ser Cys Gln Lys Lys Ser Ser Pro Ser
        515                 520                 525

Thr Ser Gly Lys Gln Glu Asp Ile Leu Lys Ile Ser Pro Arg Glu Lys
    530                 535                 540

Leu Leu Gly Asp Gln Pro Glu Leu Leu Gln Gln Phe Gly Leu Asp Leu
545                 550                 555                 560

Leu Pro Val Leu Val Gln Ile Tyr Gly Ser Ser Val Asn Gly Thr Ile
                565                 570                 575

Arg His Lys Cys Leu Ser Val Ile Gly Lys Leu Met Tyr Phe Ser Ser
            580                 585                 590

Ser Glu Met Ile Gln Ser Leu Ile Gly Asp Thr Asn Ile Ser Ser Phe
        595                 600                 605

Leu Ala Gly Val Leu Ala Trp Lys Asp Pro Gln Val Leu Val Pro Ala
    610                 615                 620

Leu Gln Val Ala Glu Ile Leu Met Glu Lys Leu Pro Glu Thr Phe Ser
625                 630                 635                 640

Lys Val Phe Val Arg Glu Gly Val Val His Ala Val Asp Gln Leu Val
                645                 650                 655

Leu Val Gly Lys Pro Ser His Ala Ser Pro Thr Asp Lys Asp Asn Asp
            660                 665                 670

Cys Val Pro Gly Ser Ala Arg Ser Arg Arg Tyr Arg Arg Ser Ser
```

-continued

```
                675                 680                 685
Asn Ala Asn Ser Asp Gly Asn Gln Ser Glu Pro Lys Asn Pro Ala
    690                 695                 700

Ser Leu Thr Ile Gly Ala Asn His Asn Ser Leu Asp Thr Pro Thr Ala
705                 710                 715                 720

Ser Phe Met Leu Arg Glu Thr Val Ser Ser Cys Ala Lys Ala Phe Lys
                725                 730                 735

Asp Lys Tyr Phe Pro Ser Asp Gly Gly Asp Val Asp Val Gly Val Thr
            740                 745                 750

Asp Asp Leu Leu His Leu Lys Asn Leu Cys Thr Lys Leu Thr Ala Gly
                755                 760                 765

Ile Asp Asp His Lys Val Lys Gly Lys Gly Lys Ser Lys Ala Ser Gly
770                 775                 780

Pro Phe Leu Gly Asp Phe Ser Ala Ser Lys Glu Tyr Leu Ile Gly
785                 790                 795                 800

Val Ile Ser Glu Ile Leu Gly Glu Ile Ser Lys Gly Asp Gly Val Ser
                805                 810                 815

Thr Phe Glu Phe Ile Gly Ser Gly Val Val Ala Ala Leu Leu Asn Tyr
            820                 825                 830

Phe Ser Cys Gly Tyr Phe Ser Lys Glu Lys Ile Ser Glu Leu Asn Leu
            835                 840                 845

Pro Lys Leu Arg Gln Glu Gly Leu Arg Arg Phe Lys Ala Phe Leu Glu
850                 855                 860

Val Ala Leu Pro Phe Asp Gly Asn Glu Gly Lys Val Pro Pro Met Thr
865                 870                 875                 880

Val Leu Ile Gln Lys Leu Gln Asn Ala Leu Ser Ser Leu Glu Arg Phe
                885                 890                 895

Pro Val Val Leu Ser His Pro Arg Ser Leu Ser Ser Ala Arg
                900                 905                 910

Leu Ser Ser Gly Leu Ser Ala Leu Ala His Pro Leu Lys Leu Arg Leu
            915                 920                 925

Cys Arg Ala Ser Gly Glu Lys Thr Leu Arg Asp Tyr Ser Ser Asn Ile
930                 935                 940

Val Leu Ile Asp Pro Leu Ala Ser Leu Ala Ala Val Glu Glu Phe Leu
945                 950                 955                 960

Trp Pro Arg Val Gln Arg Ser Glu Ser Ala Leu Lys Pro Ala Pro
                965                 970                 975

Ile Gly Asn Thr Glu Pro Gly Thr Leu Pro Ser Gly Ala Gly Val Ser
            980                 985                 990

Ser Pro Ser Ser Ser Thr Pro Ala Ser Thr Thr Arg Arg His Ser Ser
        995                 1000                1005

Arg Ser Arg Ser Ala Ile Asn Ile Gly Asp Thr Ser Lys Lys Asp
    1010                1015                1020

Pro Val His Glu Lys Gly Thr Ser Ser Ser Lys Gly Lys Gly Lys
    1025                1030                1035

Gly Val Met Lys Pro Ala Gln Ala Asp Lys Gly Pro Gln Thr Arg
    1040                1045                1050

Ser Asn Ala Gln Lys Arg Ala Val Leu Asp Lys Asp Thr Gln Met
    1055                1060                1065

Lys Pro Ala Ser Gly Asp Ser Ser Ser Glu Asp Glu Glu Leu Glu
    1070                1075                1080

Ile Ser Pro Val Asp Ile Asp Asp Ala Leu Val Ile Glu Glu Asp
    1085                1090                1095
```

```
Asp Ile Ser Asp Asp Glu Asp Asp Asn Glu Asp Val Leu Asp
    1100            1105            1110

Asp Ser Leu Pro Met Cys Thr Pro Asp Lys Val His Asp Val Lys
    1115            1120            1125

Leu Ala Asp Ser Val Asp Asp Gly Leu Ala Thr Ser Gly Arg
    1130            1135            1140

Gln Met Asn Pro Ala Ser Gly Gly Thr Ser Gly Ala Ala Ala Ala
    1145            1150            1155

Arg Ala Ser Asp Ser Ile Asp Thr Gly Ile Gly Asn Ser Tyr Gly
    1160            1165            1170

Ser Arg Gly Ala Leu Ser Phe Ala Ala Ala Met Ala Gly Leu
    1175            1180            1185

Gly Ala Ala Ser Gly Arg Gly Ile Arg Gly Ser Arg Asp Leu His
    1190            1195            1200

Gly Arg Thr Leu Asn Arg Ser Ser Asp Glu Pro Ser Lys Leu Ile
    1205            1210            1215

Phe Thr Ala Ala Gly Lys Gln Leu Ser Arg His Leu Thr Ile Tyr
    1220            1225            1230

Gln Ala Val Gln Arg Gln Leu Met Leu Asp Glu Asp Asp Asp Asp
    1235            1240            1245

Arg Phe Gly Gly Ser Asp Leu Val Ser Ser Asp Gly Ser Arg Phe
    1250            1255            1260

Asn Asp Ile Tyr Thr Ile Met Tyr Gln Arg Pro Asp Ser Gln Val
    1265            1270            1275

Asn Arg Leu Ser Val Gly Gly Ala Ser Ser Thr Thr Pro Ser Lys
    1280            1285            1290

Ser Thr Lys Ser Ala Thr Thr Asn Ser Ser Val Glu Ser Gln Ser
    1295            1300            1305

His Arg Ala Ser Leu Leu Asp Ser Ile Leu Gln Gly Glu Leu Pro
    1310            1315            1320

Cys Asp Leu Glu Lys Ser Asn Ser Thr Tyr Asn Val Leu Ala Leu
    1325            1330            1335

Leu Arg Val Leu Glu Gly Leu Asn Gln Leu Cys Pro Arg Leu Arg
    1340            1345            1350

Ala Gln Thr Leu Ser Asp Arg Phe Ala Glu Gly Lys Ile Thr Ser
    1355            1360            1365

Leu Asp Asp Leu Ser Thr Thr Ala Ala Lys Val Pro Leu Asp Glu
    1370            1375            1380

Phe Val Asn Ser Lys Leu Thr Pro Lys Leu Ala Arg Gln Ile Gln
    1385            1390            1395

Asp Ala Leu Ala Leu Cys Ser Gly Ser Leu Pro Ser Trp Cys Tyr
    1400            1405            1410

Gln Leu Thr Arg Ala Cys Pro Phe Leu Phe Pro Phe Gln Thr Arg
    1415            1420            1425

Arg Gln Tyr Phe Tyr Ser Thr Ala Phe Gly Leu Ser Arg Ala Leu
    1430            1435            1440

Asn Arg Leu Gln Gln Gln Gln Gly Ala Asp Gly Ser Gly Ser Thr
    1445            1450            1455

Asn Glu Arg Glu Met Arg Ile Gly Arg Leu Gln Arg Gln Lys Val
    1460            1465            1470

Arg Val Ser Arg Asn Arg Ile Leu Asp Ser Ala Ala Lys Val Met
    1475            1480            1485
```

```
Glu Met Tyr Ser Ser Gln Lys Ala Val Leu Glu Val Glu Tyr Phe
    1490                1495                1500
Gly Glu Val Gly Thr Gly Leu Gly Pro Thr Leu Glu Phe Tyr Thr
    1505                1510                1515
Leu Leu Ser His Asp Leu Gln Lys Ala Ser Leu Gly Met Trp Arg
    1520                1525                1530
Ser Ser Ser Gly Asp Lys Val Ser Met Gln Ile Gly Arg Asp Glu
    1535                1540                1545
Ile Glu Asp Gly Lys Pro Ser Ala Ala Asn Arg Asp Ile Val Leu
    1550                1555                1560
Ala Pro Leu Gly Leu Phe Pro Arg Pro Trp Pro Ser Thr Ala Asp
    1565                1570                1575
Ile Ser Glu Gly Gly Gln Phe His Lys Val Ile Glu Tyr Phe Arg
    1580                1585                1590
Leu Leu Gly Arg Val Met Ala Lys Ala Leu Gln Asp Gly Arg Leu
    1595                1600                1605
Leu Asp Val Pro Leu Ser Thr Ala Phe Tyr Lys Leu Ile Leu Gly
    1610                1615                1620
Gln Glu Leu Asp Leu His Asp Ile Val Leu Phe Asp Ala Glu Leu
    1625                1630                1635
Gly Lys Thr Leu Gln Glu Leu Arg Val Val Ala Arg Lys His
    1640                1645                1650
Tyr Leu Glu Gly Val Gly Gly Asp Asn Ser Ser Thr Ile Ser Asp
    1655                1660                1665
Leu Cys Leu Arg Gly Cys Arg Ile Glu Asp Leu Ser Leu Glu Phe
    1670                1675                1680
Thr Leu Pro Gly Tyr Pro Glu Tyr Ile Leu Arg Ser Gly Asp Glu
    1685                1690                1695
Ile Val Asp Ile Thr Asn Leu Glu Glu Tyr Ile Ser Leu Val Val
    1700                1705                1710
Asp Ala Thr Val Lys Arg Gly Val Thr Arg Gln Ile Glu Ala Phe
    1715                1720                1725
Arg Ser Gly Phe Asn Gln Val Phe Asp Ile Thr Ser Leu Gln Ile
    1730                1735                1740
Phe Thr Pro Ser Glu Leu Asp Tyr Leu Leu Cys Gly Arg Arg Glu
    1745                1750                1755
Leu Trp Glu Val Glu Thr Leu Ala Glu His Ile Lys Phe Asp His
    1760                1765                1770
Gly Tyr Asn Ala Lys Ser Pro Ala Ile Ile Asn Leu Leu Glu Ile
    1775                1780                1785
Met Gly Glu Leu Thr Ala Asp Gln Gln Arg Ala Phe Cys Gln Phe
    1790                1795                1800
Val Thr Gly Ala Pro Arg Leu Pro Pro Gly Gly Leu Ala Val Leu
    1805                1810                1815
Asn Pro Lys Leu Thr Ile Val Arg Lys His Ser Ser Thr Ser Ser
    1820                1825                1830
Ala Ala Ala Asn Gly Ala Gly Ala Ser Glu Thr Ala Asp Asp Asp
    1835                1840                1845
Leu Pro Ser Val Met Thr Cys Ala Asn Tyr Leu Lys Leu Pro Pro
    1850                1855                1860
Tyr Ser Thr Lys Glu Ile Met Tyr Lys Lys Leu Leu Tyr Ala Ile
    1865                1870                1875
Asn Glu Gly Gln Gly Ser Phe Asp Leu Ser
```

```
              1880              1885
```

<210> SEQ ID NO 4
<211> LENGTH: 4
<212> TYPE: PRT
<213> ORGANISM: Arabidopsis thaliana

<400> SEQUENCE: 4

Gly Asp Ser Leu
1

<210> SEQ ID NO 5
<211> LENGTH: 4
<212> TYPE: PRT
<213> ORGANISM: Arabidopsis thaliana

<400> SEQUENCE: 5

Asp Cys Ile His
1

<210> SEQ ID NO 6
<211> LENGTH: 14
<212> TYPE: PRT
<213> ORGANISM: Arabidopsis thaliana

<400> SEQUENCE: 6

Met Phe Val Gly Asp Ser Leu Asn Arg Asn Gln Trp Glu Ser
1               5                   10

<210> SEQ ID NO 7
<211> LENGTH: 10
<212> TYPE: PRT
<213> ORGANISM: Arabidopsis thaliana

<400> SEQUENCE: 7

Ala Asp Cys Ile His Trp Cys Leu Pro Gly
1               5                   10

<210> SEQ ID NO 8
<211> LENGTH: 555
<212> TYPE: PRT
<213> ORGANISM: Zea mays

<400> SEQUENCE: 8

Met Gln Gln Arg Arg Lys Ser Val Phe Ala Ser Ala Pro Phe Ala Met
1               5                   10                  15

Lys Gln Ala Ala Leu Gly Ala Gly Val Ala Ala Arg Lys Asn Gly Ala
            20                  25                  30

Pro Leu Ser Leu Ala Ala Val Val Phe Ala Leu Phe Val Phe Ala Thr
        35                  40                  45

Phe Leu Tyr Asn Glu Asp Ile Lys Ser Ile Thr Asp Phe Gln Phe Ser
    50                  55                  60

Ser Gly Ala Ile Arg Ala Lys Ser Pro Asp Leu His Leu Leu Gln Glu
65                  70                  75                  80

Ala Glu Ala Ala Ala His Ala Ala Val Asn Thr Leu Ala Lys Arg Gly
                85                  90                  95

Glu Glu Val Ile Val Arg Val Leu Glu Val Ala Pro Pro Val Val
            100                 105                 110

Asn Thr Ser Ser Val Leu Ala Ala Ala Lys Ala Ser Ala Lys Ala
            115                 120                 125

Asn Ala Val Asp Val Gly Gln Glu Lys Glu Arg Asp Val Thr Leu Pro

```
              130                 135                 140
Thr Val Thr Gly Gly Arg Gly Gly Ala Asp Glu Ala Gln Arg Ala
145                 150                 155                 160

Asp Glu Glu Val Ala Glu Lys Ala Ala Ser Ala Lys Ala Ala Ala
                    165                 170                 175

Thr Ala Ala Leu Arg Gly Val Val Ser Val Pro Gln Thr Cys Asp Leu
                180                 185                 190

Tyr Arg Gly Ser Trp Val Tyr Asp Glu Val Ser Ala Pro Val Tyr Lys
            195                 200                 205

Glu Gly Glu Cys Glu Phe Leu Thr Glu Gln Val Thr Cys Met Arg Asn
        210                 215                 220

Gly Arg Arg Asp Asp Ser Tyr Gln Lys Trp Arg Trp Gln Pro Ala Gly
225                 230                 235                 240

Cys Asp Leu Pro Arg Phe Asp Ala Arg Leu Leu Leu Glu Arg Leu Arg
                245                 250                 255

Asn Lys Arg Leu Met Phe Val Gly Asp Ser Leu Asn Arg Asn Gln Trp
                260                 265                 270

Glu Ser Met Val Cys Leu Val Gln Ser Val Ile Pro Asp Arg Gly Gln
        275                 280                 285

Lys Thr Leu Thr Lys Phe Val Asn Gly Gly Ser Ser Asn Val Phe Tyr
290                 295                 300

Ala His Glu Tyr Asn Ala Thr Val Glu Phe Tyr Trp Ala Pro Phe Leu
305                 310                 315                 320

Val Glu Ser Asn Ser Asp Asn Pro Lys Val His Ser Val Pro Asp Arg
                325                 330                 335

Val Ile Gln Trp His Ala Ile Ala Lys His Ala Arg Asn Trp Ile Gly
                340                 345                 350

Val Asp Tyr Leu Val Phe Asn Thr Tyr Ile Trp Trp Leu Asn Thr Leu
            355                 360                 365

Asp Ile Lys Val Leu Lys Gln Gly Ser Ser Phe Asp Asp Gln Gly Ser
        370                 375                 380

Thr Glu Tyr Val Glu Val Asp Arg Pro Val Ala Tyr Lys Glu Val Leu
385                 390                 395                 400

Thr Thr Trp Ala Lys Trp Val Asp Arg Asn Ile Asp Pro Asn Arg Thr
                405                 410                 415

Thr Val Phe Phe Met Gly Met Ser Pro Asn His Ile Thr Pro Glu Ala
                420                 425                 430

Trp Gly Asn Lys Gly Gly Ile Lys Cys Ala Met Glu Thr Leu Pro Ile
            435                 440                 445

Ala Ser Asn Arg Ser Ala Ala Leu Asp Val Gly Thr Asp Trp Arg Leu
450                 455                 460

Tyr Ala Gly Ala Arg Glu Val Leu Pro Thr Leu Arg Arg Val Pro Val
465                 470                 475                 480

His Phe Val Asp Ile Thr Ala Leu Ser Glu Leu Arg Lys Asp Ala His
                485                 490                 495

Thr Ser Val His Thr Leu Arg Gln Gly Lys Leu Leu Thr Pro Glu Gln
                500                 505                 510

Gln Ala Asp Pro Lys Thr Tyr Ala Asp Cys Ile His Trp Cys Leu Pro
            515                 520                 525

Gly Leu Pro Asp Thr Trp Asn Gln Phe Leu Tyr Ala Arg Ile Ala Ser
530                 535                 540

Ser Pro Trp Pro Asn Asp Ala Gln Ala Gln Gln
545                 550                 555
```

<210> SEQ ID NO 9
<211> LENGTH: 558
<212> TYPE: PRT
<213> ORGANISM: Oryza sativa

<400> SEQUENCE: 9

```
Met Gln Gln Arg Arg Lys Ser Val Phe Ala Ser Ala Pro Phe Ala Met
1               5                   10                  15

Lys Gln Ala Ala Leu Gly Ala Gly Val Ala Ala Arg Arg Asn Gly Ala
            20                  25                  30

Pro Leu Ser Leu Ala Ala Val Val Phe Ala Leu Phe Val Phe Ala Thr
        35                  40                  45

Phe Leu Tyr Asn Glu Asp Ile Lys Ser Ile Ala Asp Phe Pro Phe Gly
    50                  55                  60

Ala Gly Ala Leu Arg Ala Lys Ser Pro Asp Leu His Val Leu Gln Glu
65                  70                  75                  80

Thr Val Gly Ala Ala His Leu Ala Ala Gly Ser Ile Ala Lys Arg Gly
                85                  90                  95

Glu Glu Val Ile Val Arg Val Leu Asp Ala Pro Ala Ser Thr Ala Met
            100                 105                 110

Ala Ala Ala Ala Gly Ser Ser Ser Asn Asn Ser Thr Ile Glu Val Ala
        115                 120                 125

Lys Ala Asn Ala Asn Ala Asn Ala Asn Ala Asp Ala Gly Val Lys
    130                 135                 140

Val Asp Glu Gly Gln Glu Arg Glu Arg Asp Val Thr Leu Pro Ser Val
145                 150                 155                 160

Lys Glu Gly Gly Ala Asp Glu Ala Arg Arg Glu Asp Glu Ala
                165                 170                 175

Ala Glu Lys Glu Ser Ser Ala Lys Ala Ala Ala Thr Ala Ala Leu
            180                 185                 190

Arg Thr Val Val Ser Val Pro Asp Thr Cys Asp Leu Tyr Arg Gly Asn
                195                 200                 205

Trp Val Tyr Asp Glu Val Asn Ala Pro Val Tyr Lys Glu Ser Gln Cys
    210                 215                 220

Glu Phe Leu Thr Glu Gln Val Thr Cys Met Arg Asn Gly Arg Arg Asp
225                 230                 235                 240

Asp Ser Tyr Gln Lys Trp Arg Trp Gln Pro Thr Asp Cys Asp Leu Pro
                245                 250                 255

Arg Phe Asp Ala Arg Leu Leu Leu Glu Arg Leu Arg Asn Lys Arg Leu
            260                 265                 270

Met Phe Val Gly Asp Ser Leu Asn Arg Asn Gln Trp Glu Ser Met Val
        275                 280                 285

Cys Leu Val Gln Ser Val Ile Pro Lys Gly Lys Lys Thr Leu Thr Lys
    290                 295                 300

Phe Val Asn Gly Gly Asn Ser Asn Ile Phe Tyr Ala His Glu Tyr Asn
305                 310                 315                 320

Ala Thr Val Glu Phe Tyr Trp Ala Pro Phe Leu Val Glu Ser Asn Ser
                325                 330                 335

Asp Asn Pro Gln Val His Ser Val Pro Asp Arg Val Ile Gln Trp His
            340                 345                 350

Ser Ile Ala Lys His Ala His Asn Trp Leu Gly Val Asp Tyr Leu Ile
        355                 360                 365

Phe Asn Thr Tyr Ile Trp Trp Leu Asn Thr Leu Asp Met Lys Val Leu
```

```
                370             375             380
Lys Gly Ser Phe Asp Gln Gly Ala Thr Glu Tyr Val Glu Val Asp Arg
385                 390                 395                 400

Pro Val Ala Tyr Lys Glu Val Leu Lys Thr Trp Ala Lys Trp Val Asp
                405                 410                 415

Arg Asn Ile Asp Pro Asn Arg Thr Thr Val Phe Phe Met Ser Met Ser
            420                 425                 430

Pro Asn His Ile Thr Pro Glu Ala Trp Gly Asn Tyr Gly Gly Ile Lys
        435                 440                 445

Cys Ala Met Glu Thr Leu Pro Ile Thr Asn Arg Thr Thr Ser Leu Asp
    450                 455                 460

Val Gly Thr Asp Trp Arg Leu Tyr Ala Gly Ala Gln Glu Val Leu Gln
465                 470                 475                 480

Thr Phe Arg Arg Val Pro Val His Leu Val Asp Ile Thr Ala Leu Ser
                485                 490                 495

Glu Leu Arg Lys Asp Ala His Thr Ser Val His Thr Leu Arg Gln Gly
            500                 505                 510

Lys Leu Leu Thr Pro Glu Gln Gln Ser Asp Pro Lys Thr Tyr Ala Asp
        515                 520                 525

Cys Ile His Trp Cys Leu Pro Gly Leu Pro Asp Thr Trp Asn Gln Phe
    530                 535                 540

Leu Tyr Ala Arg Ile Ala Ser Ala Pro Trp Ser Ser Asp Gln
545                 550                 555

<210> SEQ ID NO 10
<211> LENGTH: 475
<212> TYPE: PRT
<213> ORGANISM: Populus trichocarpa

<400> SEQUENCE: 10

Pro Ser Arg Arg Lys Ser Pro Leu Leu Ser Ser Val Thr Val Thr Met
1               5                   10                  15

Lys His Arg Lys Asn Ser Asn Leu Ser Val Phe Val Val Phe Ser
                20                  25                  30

Val Phe Leu Phe Gly Val Phe Met Tyr Asn Glu Asp Val Lys Ser Ile
                35                  40                  45

Ala Glu Phe Pro Phe Ser Trp Pro Lys Ser Gln Glu Glu Pro Ser Lys
    50                  55                  60

Gly Val Thr Pro Val Gln Glu Thr Leu Glu Lys Asp Gln Glu Leu Pro
65                  70                  75                  80

Ala Ser Val Gly Ser Arg Thr Ser Leu Glu Glu Pro Gln Val Asp Gln
                85                  90                  95

Gly Pro Ala Glu Asn Glu Ser Lys Glu Asp Glu Lys Ile Glu Phe
                100                 105                 110

Pro Val Ile Glu Glu Asp Asp Glu Val Glu Leu Pro Pro Glu Glu
                115                 120                 125

Cys Asp Leu Phe Thr Gly Gln Trp Val Phe Asp Asn Glu Thr Arg Pro
    130                 135                 140

Leu Tyr Lys Glu Asp Glu Cys Glu Phe Leu Thr Ala Gln Val Thr Cys
145                 150                 155                 160

Met Arg Asn Gly Arg Lys Asp Ser Leu Tyr Gln Asn Trp Lys Trp Gln
                165                 170                 175

Pro Arg Asp Cys Ser Leu Pro Lys Phe Lys Pro Arg Leu Leu Leu Asn
                180                 185                 190
```

```
Lys Leu Arg Asn Lys Arg Leu Met Phe Val Gly Asp Ser Leu Asn Arg
            195                 200                 205

Asn Gln Trp Glu Ser Met Val Cys Phe Val Gln Ser Leu Ile Pro Pro
210                 215                 220

Gly Arg Lys Ser Leu Asn Lys Thr Gly Ser Leu Ala Val Phe Arg Ile
225                 230                 235                 240

Glu Asp Tyr Asn Ala Thr Val Glu Phe Tyr Ala Pro Phe Leu Val
            245                 250                 255

Glu Ser Asn Ser Asp Asp Pro Asn Met His Ser Ile Leu Asn Arg Ile
            260                 265                 270

Ile Met Pro Glu Ser Ile Asp Lys His Gly Val Asn Trp Lys Asn Val
            275                 280                 285

Asp Tyr Leu Val Phe Asn Thr Tyr Ile Trp Trp Met Asn Thr Phe Lys
            290                 295                 300

Met Lys Val Leu Arg Gly Ser Phe Asp Glu Gly Ser Thr Glu Tyr Asp
305                 310                 315                 320

Glu Ile Glu Arg Pro Val Ala Tyr Arg Arg Val Leu Thr Thr Trp Ser
            325                 330                 335

Lys Trp Val Glu Lys Asn Val Asp Thr Asn Arg Thr Thr Val Phe Phe
            340                 345                 350

Ser Ser Met Ser Pro Leu His Ile Lys Ser Leu Asp Trp Glu Asn Pro
            355                 360                 365

Asp Gly Ile Lys Cys Ala Lys Glu Thr Ala Pro Ile Leu Asp Val Ser
            370                 375                 380

Met Lys Phe Asn Leu Gly Thr Asp Arg Arg Leu Phe Ala Val Ala Ala
385                 390                 395                 400

Asn Ile Thr Gly Ser Met Lys Val Pro Val His Phe Ile Asn Ile Thr
            405                 410                 415

Lys Leu Ser Glu Tyr Arg Lys Asp Ala His Thr Ser Val Tyr Thr Ile
            420                 425                 430

Arg Gln Gly Lys Met Leu Thr Pro Glu Gln Gln Ala Asp Pro Ala Thr
            435                 440                 445

Tyr Ala Asp Cys Ile His Trp Cys Leu Pro Gly Leu Pro Asp Thr Trp
450                 455                 460

Asn Glu Phe Leu Tyr Thr Arg Ile Ile Ser Arg
465                 470                 475

<210> SEQ ID NO 11
<211> LENGTH: 564
<212> TYPE: PRT
<213> ORGANISM: Sorghum bicolor

<400> SEQUENCE: 11

Met Gln Gln Arg Arg Lys Ser Val Phe Ala Ser Ala Pro Phe Ala Met
1               5                   10                  15

Lys Gln Ala Ala Leu Gly Ala Gly Val Ala Ala Arg Lys Asn Gly Ala
            20                  25                  30

Pro Leu Ser Leu Ala Ala Val Val Phe Ala Leu Phe Val Phe Ala Thr
        35                  40                  45

Phe Leu Tyr Asn Glu Asp Ile Lys Ser Ile Thr Asp Phe Gln Phe Ser
    50                  55                  60

Ser Gly Ala Ile Arg Ala Lys Ser Pro Asp Leu His Leu Leu Gln Glu
65                  70                  75                  80

Ala Gln Ala Ala Ala His Ala Val Asn Thr Leu Ala Lys Arg Gly
                85                  90                  95
```

-continued

```
Glu Glu Val Ile Val Arg Val Leu Glu Ala Pro Val Ser Gln Ser Gln
                100                 105                 110

Ala Ala Pro Val Asn Thr Thr Thr Ser Val Val Val Lys Ala Ala
            115                 120                 125

Ala Ala Ala Ala Ala Ala Ala Ala Ala Ala Lys Ala Asn Ala Lys Ala
130                 135                 140

Asn Ala Val Val Asp Val Gly Gln Glu Lys Glu Arg Asp Val Thr Leu
145                 150                 155                 160

Pro Thr Val Thr Gly Gly Gly Ala Asp Glu Ala Arg Arg Ala
            165                 170                 175

Asp Glu Val Ala Glu Lys Ala Ser Ala Lys Ala Ala Ala
            180                 185                 190

Thr Ala Ala Leu Arg Thr Val Val Ser Val Pro Glu Thr Cys Asp Leu
            195                 200                 205

Tyr Arg Gly Ser Trp Val Tyr Asp Glu Val Asn Ala Pro Val Tyr Lys
            210                 215                 220

Glu Gly Glu Cys Glu Phe Leu Thr Glu Gln Val Thr Cys Met Arg Asn
225                 230                 235                 240

Gly Arg Arg Asp Asp Ser Tyr Gln Lys Trp Arg Trp Gln Pro Ala Asp
            245                 250                 255

Cys Asp Leu Pro Arg Phe Asp Ala Arg Leu Leu Glu Arg Leu Arg
            260                 265                 270

Asn Lys Arg Leu Met Phe Val Gly Asp Ser Leu Asn Arg Asn Gln Trp
            275                 280                 285

Glu Ser Met Val Cys Leu Val Gln Ser Val Ile Pro Lys Gly Lys Lys
            290                 295                 300

Thr Leu Thr Lys Phe Val Asn Gly Gly Ser Ser Asn Val Phe Tyr Ala
305                 310                 315                 320

His Glu Tyr Asn Ala Thr Val Glu Phe Tyr Trp Ala Pro Phe Leu Val
                325                 330                 335

Glu Ser Asn Ser Asp Asn Pro Lys Val His Ser Val Pro Asp Arg Val
            340                 345                 350

Ile Gln Trp His Ala Ile Ala Lys His Ala Arg Asn Trp Val Gly Val
            355                 360                 365

Asp Tyr Leu Val Phe Asn Thr Tyr Ile Trp Trp Leu Asn Thr Leu Asp
370                 375                 380

Met Lys Val Leu Lys Gly Ser Phe Asp Gln Gly Ser Thr Glu Tyr Val
385                 390                 395                 400

Glu Val Asp Arg Pro Val Ala Tyr Lys Glu Val Leu Lys Thr Trp Ala
                405                 410                 415

Lys Trp Val Asp Arg Asn Ile Asp Pro Asn Arg Thr Thr Val Phe Phe
            420                 425                 430

Met Gly Met Ser Pro Asn His Ile Thr Pro Glu Ala Trp Gly Asn Gln
            435                 440                 445

Gly Gly Ile Lys Cys Ala Met Glu Thr Leu Pro Ile Thr Asn Arg Ser
            450                 455                 460

Ala Ser Leu Asp Val Gly Thr Asp Trp Arg Leu Tyr Ala Gly Ala Arg
465                 470                 475                 480

Glu Val Leu Pro Thr Leu Arg Arg Val Pro Val His Phe Val Asp Ile
                485                 490                 495

Thr Ala Leu Ser Glu Leu Arg Lys Asp Ala His Thr Ser Val His Thr
            500                 505                 510
```

```
Leu Arg Gln Gly Lys Leu Leu Thr Pro Glu Gln Ala Asp Pro Lys
            515                 520                 525

Thr Tyr Ala Asp Cys Ile His Trp Cys Leu Pro Gly Leu Pro Asp Thr
        530                 535                 540

Trp Asn Gln Phe Leu Tyr Ala Arg Ile Ala Ser Ser Pro Trp Pro Ala
545                 550                 555                 560

Ala His Gln Gln

<210> SEQ ID NO 12
<211> LENGTH: 5
<212> TYPE: PRT
<213> ORGANISM: Arabidopsis thaliana

<400> SEQUENCE: 12

His Asp Tyr His Leu
1               5

<210> SEQ ID NO 13
<211> LENGTH: 11
<212> TYPE: PRT
<213> ORGANISM: Arabidopsis thaliana

<400> SEQUENCE: 13

Phe Leu His Ser Pro Phe Pro Ser Ser Glu Ile
1               5                   10

<210> SEQ ID NO 14
<211> LENGTH: 6
<212> TYPE: PRT
<213> ORGANISM: Arabidopsis thaliana

<400> SEQUENCE: 14

Ala Ala Glu His Gly Tyr
1               5

<210> SEQ ID NO 15
<211> LENGTH: 11
<212> TYPE: PRT
<213> ORGANISM: Arabidopsis thaliana

<400> SEQUENCE: 15

Gly Asp Asp Arg Ser Asp Glu Asp Met Phe Glu
1               5                   10

<210> SEQ ID NO 16
<211> LENGTH: 9
<212> TYPE: PRT
<213> ORGANISM: Arabidopsis thaliana

<400> SEQUENCE: 16

Cys Thr Val Gly Gln Lys Pro Ser Lys
1               5

<210> SEQ ID NO 17
<211> LENGTH: 793
<212> TYPE: PRT
<213> ORGANISM: Zea mays

<400> SEQUENCE: 17

Met Glu Val Leu Phe Val Gly Ser Leu Arg Ala Asp Val Pro Ala Ala
1               5                   10                  15

Glu Gln Asp Glu Val Ser Gln Thr Leu Leu Asp Arg Phe Arg Cys Ala
            20                  25                  30
```

Pro Val Phe Leu Pro Asp His Leu Asn Asp Arg Phe Tyr His Gly Phe
         35                  40                  45

Cys Lys Arg Gln Leu Trp Pro Leu Phe His Tyr Met Leu Pro Phe Ser
 50                  55                  60

Ser Pro Ala Ser Ala Ala Ala Thr Ser Ser Ser Val Ala Thr
 65              70                  75                  80

Ser Ser Pro Gly Asn Gly Arg Phe Asp Arg Ser Ala Trp Glu Ala Tyr
                 85                  90                  95

Val Leu Ala Asn Lys Phe Phe Glu Lys Val Val Glu Val Ile Asn
                100             105             110

Pro Glu Asp Asp Tyr Val Trp Val His Asp Tyr His Leu Leu Ala Leu
             115                 120                 125

Pro Thr Phe Leu Arg Arg Arg Phe Asn Arg Leu Arg Ile Gly Phe Phe
         130                 135                 140

Leu His Ser Pro Phe Pro Ser Ser Glu Ile Tyr Arg Thr Leu Pro Val
145                 150                 155                 160

Arg Asp Glu Ile Leu Lys Ala Leu Leu Asn Cys Asp Leu Ile Gly Phe
                 165                 170                 175

His Thr Phe Asp Tyr Ala Arg His Phe Leu Ser Cys Cys Ser Arg Met
             180                 185                 190

Leu Gly Ile Glu Tyr Gln Ser Lys Arg Gly His Ile Gly Leu Asp Tyr
         195                 200                 205

Phe Gly Arg Thr Val Gly Ile Lys Ile Met Pro Val Gly Val His Met
210                 215                 220

Gly Gln Leu Glu Ser Gly Leu Arg Leu Pro Asp Arg Glu Trp Arg Leu
225                 230                 235                 240

Ser Glu Leu Gln Gln Gln Phe Gln Gly Lys Thr Val Leu Leu Gly Val
                 245                 250                 255

Asp Asp Met Asp Ile Phe Lys Gly Ile Asn Leu Lys Leu Leu Ala Phe
             260                 265                 270

Glu Asn Met Leu Arg Thr His Pro Lys Trp Gln Gly Arg Ala Val Leu
         275                 280                 285

Val Gln Ile Ala Asn Pro Ala Arg Gly Arg Gly Lys Asp Leu Glu Ala
290                 295                 300

Ile Gln Ala Glu Ile Glu Glu Ser Cys Gln Arg Ile Asn Gly Asp Phe
305                 310                 315                 320

Gly Gln Ser Gly Tyr Ser Pro Val Val Phe Ile Asp Arg Asp Val Ser
                 325                 330                 335

Ser Val Glu Lys Ile Ala Tyr Tyr Thr Ile Ala Glu Cys Val Val Val
             340                 345                 350

Thr Ala Val Arg Asp Gly Met Asn Leu Thr Pro Tyr Glu Tyr Ile Val
         355                 360                 365

Cys Arg Gln Gly Ala Pro Gly Ser Glu Ser Val Ser Glu Val Gly Gly
370                 375                 380

Pro Lys Lys Ser Met Leu Val Val Ser Glu Phe Ile Gly Cys Ser Pro
385                 390                 395                 400

Ser Leu Ser Gly Ala Ile Arg Val Asn Pro Trp Asn Ile Glu Ala Thr
                 405                 410                 415

Ala Glu Ala Met Asn Glu Ala Ile Ser Met Pro Glu Gln Glu Lys Gln
             420                 425                 430

Leu Arg His Glu Lys His Tyr Arg Tyr Val Ser Ser His Asp Val Ala
         435                 440                 445

```
Tyr Trp Ser Lys Ser Phe Ile Leu Asp Leu Glu Arg Ala Cys Arg Asp
            450                 455                 460

His Phe Lys Arg Thr Cys Trp Gly Ile Gly Leu Gly Phe Gly Phe Arg
465                 470                 475                 480

Val Val Ala Leu Asp Ala His Phe Arg Lys Leu Asn Met Asp Ser Ile
                485                 490                 495

Val Asn Ala Tyr Glu Ile Ser Gly Ser Arg Ala Ile Leu Leu Asp Tyr
            500                 505                 510

Asp Gly Thr Leu Val Pro Gln Thr Ser Ile Asn Lys Glu Pro Ser Pro
            515                 520                 525

Glu Val Leu Asn Ile Ile Asn Thr Leu Cys Ser Asp Ser Arg Asn Ile
530                 535                 540

Val Phe Leu Val Ser Gly Arg Asp Lys Asp Met Leu Gly Lys Trp Phe
545                 550                 555                 560

Ser Ser Cys Pro Lys Leu Gly Ile Ala Ala Glu His Gly Tyr Phe Leu
                565                 570                 575

Arg Trp Ser Ser Glu Glu Glu Trp Gln Thr Cys Thr Gln Ala Met Asp
            580                 585                 590

Phe Gly Trp Met Gln Met Ala Lys Pro Val Met Asn Leu Tyr Thr Glu
            595                 600                 605

Ala Thr Asp Gly Ser Tyr Ile Glu Thr Lys Glu Ser Ala Leu Val Trp
610                 615                 620

His His Gln Asp Ala Asp Pro Gly Phe Gly Ser Ser Gln Ala Lys Glu
625                 630                 635                 640

Leu Leu Asp His Leu Glu Ser Val Leu Ala Asn Glu Pro Val Ser Val
                645                 650                 655

Lys Ser Gly Gln Phe Ile Val Glu Val Lys Pro Gln Gly Val Ser Lys
            660                 665                 670

Gly Ile Val Ala Glu Arg Ile Leu Ala Ser Val Lys Glu Arg Gly Lys
            675                 680                 685

Gln Ala Asp Phe Val Leu Cys Ile Gly Asp Asp Arg Ser Asp Glu Asp
690                 695                 700

Met Phe Glu Asn Ile Ala Asp Ile Ile Lys Arg Asn Met Val Ala Pro
705                 710                 715                 720

Arg Thr Ser Leu Phe Ala Cys Thr Val Gly Gln Lys Pro Ser Lys Ala
                725                 730                 735

Lys Phe Tyr Leu Asp Asp Thr Phe Glu Val Val Ala Met Leu Ser Ala
            740                 745                 750

Leu Ala Asp Ala Thr Gly Ala Glu Leu Glu Ser Asp Ser Ala Asp Glu
            755                 760                 765

Leu Ala Ala Ser Ile Ser Ser Leu Asp Ile Gly Asp Glu Gln Ser Glu
770                 775                 780

Thr Ser Asp Thr Pro Ile Gly Gly Ser
785                 790

<210> SEQ ID NO 18
<211> LENGTH: 913
<212> TYPE: PRT
<213> ORGANISM: Oryza sativa

<400> SEQUENCE: 18

Met Met Ser Arg Ser Tyr Thr Asn Leu Leu Asp Leu Ala Glu Gly Asn
1               5                   10                  15

Phe Ala Ala Leu Gly Pro Gly Gly Gly Gly Gly Arg Arg Ser
            20                  25                  30
```

Gly Ser Phe Gly Leu Lys Arg Met Ser Arg Val Met Thr Val Pro Gly
            35                  40                  45

Thr Leu Ser Glu Leu Asp Gly Glu Asp Ser Glu His Ala Ala Thr
 50                  55                  60

Asn Ser Val Ala Ser Asp Val Pro Ser Ser Val Ala Gly Asp Arg Val
 65                  70                  75                  80

Ile Val Val Ser Asn Gln Leu Pro Val Val Ala Arg Arg Pro Asp
                85                  90                  95

Gly Arg Gly Trp Ser Phe Ser Trp Asp Asp Ser Leu Leu Leu Gln
                100                 105                 110

Leu Arg Asp Gly Ile Pro Asp Glu Met Glu Val Phe Phe Val Gly Ser
            115                 120                 125

Leu Arg Ala Glu Ile Pro Val Ala Asp Gln Glu Glu Val Ser Gln Ala
            130                 135                 140

Leu Leu Asp Arg Phe Arg Cys Ala Pro Val Phe Leu Pro Asp Pro Leu
145                 150                 155                 160

Asn Glu Arg Phe Tyr His Arg Phe Cys Lys Arg His Leu Trp Pro Leu
                165                 170                 175

Phe His Tyr Met Leu Pro Phe Ser Ser Ser Ala Ser Pro Ser Pro Ser
            180                 185                 190

Ser Ser Ser Ser Ser Ser Ser Pro Ser Ser Ser Ser Gly Ser Gly
            195                 200                 205

His Phe Asp Arg Gly Ala Trp Glu Ala Tyr Val Leu Ala Asn Lys Phe
            210                 215                 220

Phe Phe Glu Lys Val Val Glu Val Ile Asn Pro Glu Asp Asp Tyr Val
225                 230                 235                 240

Trp Val His Asp Tyr His Leu Met Ala Leu Pro Thr Phe Leu Arg Arg
                245                 250                 255

Arg Phe Asn Arg Leu Arg Ile Gly Phe Phe Leu His Ser Pro Phe Pro
            260                 265                 270

Ser Ser Glu Ile Tyr Arg Thr Leu Pro Val Arg Glu Glu Ile Leu Lys
            275                 280                 285

Ala Leu Leu Asn Cys Asp Leu Ile Gly Phe His Thr Phe Asp Tyr Ala
            290                 295                 300

Arg His Phe Leu Ser Cys Cys Ser Arg Met Leu Gly Ile Glu Tyr Gln
305                 310                 315                 320

Ser Lys Arg Gly Tyr Ile Gly Leu Asp Tyr Phe Gly Arg Thr Val Gly
                325                 330                 335

Ile Lys Ile Met Pro Val Gly Val His Met Gly Gln Leu Lys Thr Val
            340                 345                 350

Leu Ser Leu Pro Asp Arg Glu Trp Arg Val Ser Glu Leu Gln Gln Gln
            355                 360                 365

Phe Glu Gly Lys Thr Val Leu Leu Gly Val Asp Asp Met Asp Ile Phe
    370                 375                 380

Lys Gly Ile Asn Leu Lys Leu Leu Ala Phe Glu Asn Met Leu Arg Thr
385                 390                 395                 400

His Pro Lys Trp Gln Gly Arg Ala Val Leu Val Gln Ile Ala Asn Pro
                405                 410                 415

Ala Arg Gly Lys Gly Lys Asp Leu Glu Ala Ile Gln Ala Glu Ile His
            420                 425                 430

Glu Ser Cys Lys Arg Ile Asn Gly Glu Phe Gly Gln Ser Gly Tyr Ser
            435                 440                 445

-continued

Pro Val Val Phe Ile Asp Arg Asp Val Ser Ser Val Glu Lys Ile Ala
450                 455                 460

Tyr Tyr Thr Ile Ala Glu Cys Val Val Thr Ala Val Arg Asp Gly
465                 470                 475                 480

Met Asn Leu Thr Pro Tyr Glu Tyr Ile Val Cys Arg Gln Gly Ser Asp
                    485                 490                 495

Ser Thr Ser Glu Val Asn Gly Pro Lys Lys Ser Met Leu Val Val Ser
            500                 505                 510

Glu Phe Ile Gly Cys Ser Pro Ser Leu Ser Gly Ala Ile Arg Val Asn
        515                 520                 525

Pro Trp Asn Ile Glu Ala Thr Glu Ala Leu Asn Glu Ala Ile Ser
530                 535                 540

Met Ser Glu Gln Glu Lys His Leu Arg His Glu Lys His Tyr Arg Tyr
545                 550                 555                 560

Val Ser Thr His Asp Val Ala Tyr Trp Ser Lys Ser Phe Ile Gln Asp
                565                 570                 575

Leu Glu Arg Ala Cys Lys Asp His Phe Arg Arg Thr Cys Trp Gly Ile
            580                 585                 590

Gly Leu Gly Phe Gly Phe Arg Val Val Ala Leu Asp Pro His Phe Thr
        595                 600                 605

Lys Leu Asn Met Asp Ser Ile Val Met Ala Tyr Glu Arg Ser Glu Ser
610                 615                 620

Arg Ala Ile Phe Leu Asp Tyr Asp Gly Thr Leu Val Pro Gln Thr Ser
625                 630                 635                 640

Ile Ser Arg Thr Pro Ser Ala Glu Val Leu Arg Ile Ile Asn Thr Leu
                645                 650                 655

Cys Ser Asp Arg Arg Asn Lys Val Phe Leu Val Ser Gly Arg Arg Arg
            660                 665                 670

Asp Lys Leu Gly Glu Trp Phe Ser Ser Cys Pro Asp Leu Gly Ile Ala
        675                 680                 685

Ala Glu His Gly Tyr Phe Leu Arg Trp Thr Arg Asp Glu Glu Trp Gln
690                 695                 700

Thr Cys Thr Gln Thr Ser Asp Phe Gly Trp Met Glu Met Ala Lys Pro
705                 710                 715                 720

Val Met Asn Leu Tyr Thr Glu Ala Thr Asp Gly Ser Tyr Ile Asp Pro
                725                 730                 735

Lys Glu Ser Ala Leu Val Trp His His Gln Asp Ala Asp Pro Gly Phe
            740                 745                 750

Gly Ser Ser Gln Ala Lys Glu Leu Leu Asp His Leu Glu Ser Val Leu
        755                 760                 765

Ala Asn Glu Pro Val Ser Val Lys Ser Gly Gln Phe Ile Val Glu Val
770                 775                 780

Lys Pro Gln Gly Val Ser Lys Gly Val Val Ala Glu Lys Ile Leu Val
785                 790                 795                 800

Ser Met Lys Glu Arg Gly Lys Gln Ala Asp Phe Val Leu Cys Ile Gly
                805                 810                 815

Asp Asp Arg Ser Asp Glu Asp Met Phe Glu Asn Ile Ala Asp Thr Ile
            820                 825                 830

Lys Lys Gly Met Val Ala Thr Asn Thr Ser Leu Phe Ala Cys Thr Val
        835                 840                 845

Gly Gln Lys Pro Ser Lys Ala Lys Phe Tyr Leu Asp Asp Thr Phe Glu
850                 855                 860

Val Val Thr Met Leu Ser Ala Leu Ala Asp Ala Thr Glu Pro Glu Pro

```
                      865                 870                 875                 880
Glu Thr Asp Leu Thr Asp Glu Phe Asp Glu Leu Ala Val Ser Val Ser
                    885                 890                 895
Ser Val Asp Ile Asp Asp Glu Gln Thr Pro Ser Asp Lys Leu Ile Gly
                900                 905                 910
Gly

<210> SEQ ID NO 19
<211> LENGTH: 855
<212> TYPE: PRT
<213> ORGANISM: Vitis vinifera

<400> SEQUENCE: 19

Met Met Ser Arg Ser Tyr Thr Asn Leu Leu Asp Leu Ala Thr Gly Asn
1               5                   10                  15
Phe Pro Ala Ile Gly Arg Glu Arg Lys Arg Leu Pro Arg Val Met Thr
            20                  25                  30
Val Pro Gly Asn Val Tyr Glu Leu Asp Asp Gln Ala Asn Ser Val
        35                  40                  45
Ser Ser Asp Asn Pro Ser Ser Val Ala Gln Asp Arg Leu Ile Ile Val
    50                  55                  60
Ala Asn Gln Leu Pro Val Lys Ala Asn Arg Arg Ala Asp Asp Arg Gly
65                  70                  75                  80
Trp Val Phe Ser Trp Asn Glu Asp Ser Leu Leu Gln Leu Lys Glu
                85                  90                  95
Gly Leu Pro Glu Asp Met Glu Val Leu Tyr Val Gly Ser Leu Arg Val
            100                 105                 110
Asp Val Asp Leu Glu Glu Gln Glu Val Ser Gln Ile Leu Leu Glu
        115                 120                 125
Thr Phe Lys Cys Val Pro Thr Phe Leu Pro His Asp Val Leu Glu Lys
    130                 135                 140
Phe Tyr His Gly Phe Cys Lys Lys Leu Leu Trp Pro Leu Phe His Tyr
145                 150                 155                 160
Met Leu Pro Phe Ser Ala Asp His Gly Gly Arg Phe Asp Arg Ser Met
                165                 170                 175
Trp Glu Ala Tyr Val Leu Ala Asn Lys Leu Phe Ser Gln Lys Val Ile
            180                 185                 190
Glu Val Ile Asn Pro Asp Asp Asp Tyr Val Trp Ile His Asp Tyr His
        195                 200                 205
Leu Met Val Leu Pro Thr Phe Leu Arg Arg His Phe Asn Gln Leu Arg
    210                 215                 220
Met Gly Phe Phe Leu His Ser Pro Phe Pro Ser Ser Glu Ile Tyr Arg
225                 230                 235                 240
Thr Leu Pro Val Arg Glu Glu Ile Leu Lys Ala Leu Leu Asn Ser Asp
                245                 250                 255
Leu Ile Gly Phe His Thr Phe Asp Tyr Ala Arg His Phe Leu Ser Cys
            260                 265                 270
Cys Ser Arg Met Leu Gly Leu Glu Tyr Gln Ser Lys Arg Gly Tyr Ile
        275                 280                 285
Gly Leu Glu Tyr Tyr Gly Arg Thr Val Gly Ile Lys Ile Met Pro Val
    290                 295                 300
Gly Ile His Met Gly Arg Ile Ala Ser Val Met Lys Leu Ala Asp Lys
305                 310                 315                 320
Gln Lys Lys Val Gly Glu Leu Lys Gln Gln Phe Glu Gly Lys Thr Val
```

-continued

```
                325                 330                 335
Leu Leu Gly Val Asp Asp Met Asp Ile Phe Lys Gly Ile Asn Leu Lys
            340                 345                 350
Leu Leu Ala Met Glu Gln Leu Gln Gln His Ser Lys Trp Gln Gly
        355                 360                 365
Lys Ala Val Leu Val Gln Ile Ala Asn Pro Ala Arg Gly Lys Gly Ala
    370                 375                 380
Asp Leu Glu Glu Ile Gln Ala Glu Ile Arg Glu Ser Cys Arg Arg Ile
385                 390                 395                 400
Asn Glu Glu Phe Gly Glu Pro Gly Tyr Glu Pro Ile Val Phe Val Asp
                405                 410                 415
Arg Pro Val Ser Ile Ser Glu Arg Ile Ala Tyr Tyr Ser Ile Ala Ala
            420                 425                 430
Cys Val Val Val Thr Ala Val Arg Asp Gly Met Asn Leu Thr Pro Tyr
        435                 440                 445
Glu Tyr Ile Val Cys Arg Gln Gly Thr Asp Asp Ser Glu Ser Ser Ser
    450                 455                 460
Asp Leu Ser Gly Pro Lys Lys Ser Met Leu Val Leu Ser Glu Phe Ile
465                 470                 475                 480
Gly Cys Ser Pro Ser Leu Ser Gly Ala Ile Arg Val Asn Pro Trp Asn
                485                 490                 495
Val Glu Ala Thr Ala Glu Ala Met Asn Glu Ala Ile Ser Met Ser Gln
            500                 505                 510
Ser Glu Gln Leu Leu Arg His Glu Lys His Phe Arg Tyr Val Ser Thr
        515                 520                 525
His Asp Val Ala Tyr Trp Ser Arg Ser Phe Leu Gln Asp Met Glu Arg
    530                 535                 540
Thr Cys Ser Glu His Phe Arg Arg Cys Trp Gly Ile Gly Leu Ser
545                 550                 555                 560
Phe Gly Phe Arg Val Ala Leu Asp Pro Asn Phe Arg Lys Leu Ser
                565                 570                 575
Met Glu Ala Ile Val Ser Ala Tyr Cys Arg Ala Lys Ser Arg Ala Ile
            580                 585                 590
Leu Leu Asp Tyr Asp Gly Thr Val Met Pro Gln Asn Ser Ile Asn Lys
        595                 600                 605
Ala Pro Ser Gln Glu Val Ile Ser Ile Leu Asn Thr Leu Cys Trp Asp
    610                 615                 620
Lys Lys Asn Thr Val Phe Ile Val Ser Gly Arg Gly Arg Asp Asn Leu
625                 630                 635                 640
Ser Gln Trp Phe Ser Pro Cys Arg Lys Leu Gly Leu Ala Ala Glu His
                645                 650                 655
Gly Tyr Phe Leu Arg Trp Ser Gln Asp Lys Glu Trp Glu Thr Cys Gly
            660                 665                 670
Gln Ser Ser Asp Phe Gly Trp Lys Gln Ile Ala Glu Pro Val Met Lys
        675                 680                 685
Leu Tyr Thr Glu Thr Thr Asp Gly Ser Ser Ile Glu Ser Lys Glu Ser
    690                 695                 700
Ala Leu Val Trp Gln Tyr Gly Asp Ala Asp Pro Gly Phe Gly Ser Ser
705                 710                 715                 720
Gln Ala Lys Glu Met Leu Asp His Leu Glu Ser Val Leu Ala Asn Glu
                725                 730                 735
Pro Val Ala Val Lys Ser Gly His Phe Ile Val Glu Val Lys Pro Gln
            740                 745                 750
```

```
Gly Val Ser Lys Gly Leu Ala Ala Glu Lys Ile Phe Thr Thr Met Thr
            755                 760                 765

Glu Asn Gly Lys Gln Ala Asp Phe Leu Leu Cys Ile Gly Asp Asp Arg
        770                 775                 780

Ser Asp Glu Asp Met Phe Glu Ile Ile Gly Ser Ala Met Ser Thr Asn
785                 790                 795                 800

Ile Leu Ser Ala Asn Thr Ser Leu Phe Ala Cys Thr Val Gly Gln Lys
                805                 810                 815

Pro Ser Lys Ala Lys Tyr Tyr Leu Asp Asp Ala Ser Glu Val Ile Cys
            820                 825                 830

Met Leu Glu Ser Leu Ala Glu Ala Ser Asp Ser Gly Pro Ser Ser Glu
            835                 840                 845

Glu Glu Thr Gln Val Ser Pro
        850                 855

<210> SEQ ID NO 20
<211> LENGTH: 853
<212> TYPE: PRT
<213> ORGANISM: Populus trichocarpa

<400> SEQUENCE: 20

Met Met Ser Arg Ser Tyr Thr Asn Leu Leu Asp Leu Ala Ser Gly Asn
1               5                   10                  15

Phe Pro Ala Met Gly Gln Pro Arg Glu Arg Lys Arg Leu Pro Arg Val
            20                  25                  30

Met Thr Val Pro Gly Val Ile Ser Glu Leu Asp Asp Asp Val Ala Asn
        35                  40                  45

Ser Val Thr Ser Asp Val Pro Ser Ser Val Val Gln Asp Arg Ile Ile
    50                  55                  60

Ile Val Gly Asn Gln Leu Pro Val Lys Ala Lys Arg Arg Pro Asp Asn
65                  70                  75                  80

Lys Gly Trp Ser Phe Ser Trp Asp Glu Asp Ser Leu Leu Leu Gln Leu
                85                  90                  95

Lys Asp Gly Leu Pro Glu Glu Met Glu Val Leu Tyr Val Gly Ser Leu
            100                 105                 110

Arg Ala Asp Ile Asp Leu Ser Glu Gln Glu Asp Val Ser Gln Ile Leu
        115                 120                 125

Leu Asp Arg Phe Lys Cys Val Pro Ala Phe Leu Pro Pro Asp Ile Leu
    130                 135                 140

Ser Lys Phe Tyr His Gly Phe Cys Lys Gln Tyr Leu Trp Pro Leu Phe
145                 150                 155                 160

His Tyr Met Leu Pro Ile Ser Gly Asn His Gly Gly Arg Phe Asp Arg
                165                 170                 175

Ser Leu Trp Glu Ala Tyr Val Ala Ala Asn Lys Ile Phe Ser Gln Arg
            180                 185                 190

Val Ile Glu Val Ile Asn Pro Gly Asp Asp Tyr Val Trp Ile His Asp
        195                 200                 205

Tyr His Leu Met Val Leu Pro Thr Phe Leu Arg Arg Arg Phe Asn Arg
    210                 215                 220

Leu Arg Met Gly Phe Phe Leu His Ser Pro Phe Pro Ser Ser Glu Ile
225                 230                 235                 240

Tyr Arg Thr Leu Pro Val Arg Glu Glu Ile Leu Lys Ala Leu Leu Asn
                245                 250                 255

Ser Asp Leu Ile Gly Phe His Thr Phe Asp Tyr Ala Arg His Phe Leu
```

```
              260                 265                 270
Ser Cys Cys Ser Arg Met Leu Gly Leu Glu Tyr Gln Ser Lys Arg Gly
            275                 280                 285

Tyr Ile Gly Leu Glu Tyr Tyr Gly Arg Thr Val Gly Ile Lys Ile Met
290                 295                 300

Pro Val Gly Ile His Met Gly Gln Ile Gln Ser Val Leu Lys Leu Ala
305                 310                 315                 320

Asp Lys Asp Trp Arg Val Glu Glu Leu Lys Gln Gln Phe Glu Gly Lys
                325                 330                 335

Thr Val Leu Leu Gly Val Asp Asp Met Asp Ile Phe Lys Gly Val Asn
            340                 345                 350

Leu Lys Leu Leu Ala Met Glu Gln Leu Leu Lys Gln His Pro Lys Trp
        355                 360                 365

Gln Arg Arg Ala Val Leu Val Gln Ile Thr Asn Pro Ala Arg Gly Arg
    370                 375                 380

Gly Arg Asp Leu Glu Glu Val Gln Ala Glu Ile Gln Glu Ser Cys Arg
385                 390                 395                 400

Arg Ile Asn Glu Thr Phe Gly Arg Pro Gly Tyr Glu Pro Val Val Phe
                405                 410                 415

Ile Asp Arg Pro Val Ser Leu Ser Glu Arg Ser Ala Tyr Phe Thr Ile
            420                 425                 430

Ala Glu Cys Val Val Val Ala Ala Val Arg Asp Gly Met Asn Leu Thr
        435                 440                 445

Pro Tyr Glu Tyr Ile Val Cys Arg Gln Gly Val Ser Gly Ser Glu Ser
    450                 455                 460

Ser Ser Gly Ser Ser Gly Pro Lys Lys Ser Met Leu Val Val Ser Glu
465                 470                 475                 480

Phe Ile Gly Cys Ser Pro Ser Leu Ser Gly Ala Ile Arg Val Asn Pro
                485                 490                 495

Trp Asn Ile Glu Ala Thr Ala Glu Ala Met Asn Glu Ala Ile Ser Met
            500                 505                 510

Ala Asp Ser Glu Lys Gln Leu Arg His Glu Lys His Tyr Arg Tyr Val
        515                 520                 525

Ser Thr His Asp Val Ala Tyr Trp Ser Arg Ser Phe Tyr Gln Asp Met
    530                 535                 540

Glu Arg Thr Cys Lys Asp His Phe Arg Arg Cys Trp Gly Ile Gly
545                 550                 555                 560

Leu Ser Phe Gly Phe Arg Val Val Ala Leu Asp Pro Asn Phe Lys Lys
                565                 570                 575

Leu Asn Ile Asp Gln Ile Glu Ser Ala Tyr Ile Lys Ser Lys Asn Arg
            580                 585                 590

Ala Ile Leu Leu Asp Tyr Asp Gly Thr Val Met Pro Gln Thr Thr Ile
        595                 600                 605

Asn Lys Thr Pro Asn Gln Glu Val Ile Ser Ile Asn Thr Leu Cys
    610                 615                 620

Ser Asp Val Lys Asn Thr Val Phe Val Ser Gly Arg Gly Arg Asp
625                 630                 635                 640

Ser Leu Gly Lys Trp Phe Ala His Cys Lys Lys Leu Gly Ile Ala Ala
                645                 650                 655

Glu His Gly Tyr Phe Met Arg Trp Ser Val Asp Glu Asp Trp Glu Asn
            660                 665                 670

Cys Gly Gln Ser Ser Asp Phe Gly Trp Thr Gln Ile Ala Glu Pro Val
        675                 680                 685
```

```
Met Asn Leu Tyr Thr Glu Ala Thr Asp Gly Ser Ser Ile Glu Thr Lys
    690                 695                 700

Glu Ser Ala Leu Val Trp His His Arg Asp Ala Asp Pro Gly Phe Gly
705                 710                 715                 720

Ala Ala Gln Ala Lys Glu Leu Leu Asp His Leu Glu Ser Val Leu Ala
                725                 730                 735

Asn Glu Pro Val Ala Val Lys Ser Gly Gln Cys Ile Val Glu Val Lys
            740                 745                 750

Pro Gln Gly Ile Ser Lys Gly Ser Val Ala Glu Lys Ile Phe Thr Ser
        755                 760                 765

Met Ala Glu Ser Gly Arg Gln Ala Asp Phe Val Leu Cys Ile Gly Asp
770                 775                 780

Asp Arg Ser Asp Glu Asp Met Phe Glu Ser Ile Asp Asn Ala Ile Ala
785                 790                 795                 800

Asn Gly Ile Leu Thr Ser Ser Lys Ser Val Phe Ala Cys Thr Val Gly
                805                 810                 815

Gln Lys Pro Ser Lys Ala Lys Tyr Tyr Leu Asp Asp Thr Thr Asp Val
            820                 825                 830

Ile Asn Met Leu Glu Ala Leu Ala Glu Ala Ser Asp Pro Ser Pro Ser
        835                 840                 845

Ala Gly Ser Ser Pro
    850

<210> SEQ ID NO 21
<211> LENGTH: 910
<212> TYPE: PRT
<213> ORGANISM: Sorghum bicolor

<400> SEQUENCE: 21

Met Met Ser Arg Ser Tyr Thr Asn Leu Leu Asp Leu Ala Glu Gly Asn
1               5                   10                  15

Phe Ala Ala Leu Gly Pro Ala Gly Gly Ser Gly Arg Gln Arg Gln Gly
            20                  25                  30

Ser Phe Gly Met Arg Arg Met Ser Arg Val Met Thr Val Pro Gly Thr
        35                  40                  45

Leu Ser Glu Leu Asp Gly Glu Asp Glu Ser Glu Pro Ala Ala Thr Asn
    50                  55                  60

Ser Val Ala Ser Asp Ala Pro Ser Ser Leu Ala Ala Asp Arg Val Ile
65                  70                  75                  80

Val Val Ser Asn Gln Leu Pro Ile Val Ala Arg Arg Arg Pro Asp Gly
                85                  90                  95

Arg Gly Trp Ser Phe Ser Trp Asp Asp Asp Ser Leu Leu Leu Gln Leu
            100                 105                 110

Arg Asp Gly Ile Pro Asp Glu Met Glu Val Leu Phe Val Gly Ser Leu
        115                 120                 125

Arg Ala Asp Val Pro Val Ala Glu Gln Asp Glu Val Ser Gln Ala Leu
    130                 135                 140

Leu Asp Arg Phe Arg Cys Ala Pro Val Phe Leu Pro Asp His Leu Asn
145                 150                 155                 160

Asp Arg Phe Tyr His Gly Phe Cys Lys Arg Gln Leu Trp Pro Leu Phe
                165                 170                 175

His Tyr Met Leu Pro Phe Ser Ser Ala Ser Ala Ala Thr Thr Ser
            180                 185                 190

Ser Ser Val Ala Pro Ser Ser Pro Gly Asn Gly Arg Phe Asp Arg Ser
```

-continued

```
            195                 200                 205
Ala Trp Glu Ala Tyr Val Leu Ala Asn Lys Phe Phe Glu Lys Val
210                 215                 220
Val Glu Val Ile Asn Pro Glu Glu Asp Tyr Val Trp Val His Asp Tyr
225                 230                 235                 240
His Leu Met Ala Leu Pro Thr Phe Leu Arg Arg Phe Asn Arg Leu
                245                 250                 255
Arg Ile Gly Phe Phe Leu His Ser Pro Phe Pro Ser Ser Glu Ile Tyr
                260                 265                 270
Arg Thr Leu Pro Val Arg Glu Glu Ile Leu Lys Ala Leu Leu Asn Cys
                275                 280                 285
Asp Leu Ile Gly Phe His Thr Phe Asp Tyr Ala Arg His Phe Leu Ser
                290                 295                 300
Cys Cys Ser Arg Met Leu Gly Ile Glu Tyr Gln Ser Lys Arg Gly Tyr
305                 310                 315                 320
Ile Gly Leu Asp Tyr Phe Gly Arg Thr Val Gly Ile Lys Ile Met Pro
                            325                 330                 335
Val Gly Ile His Met Gly Gln Leu Glu Ser Gly Leu Arg Leu Pro Asp
                340                 345                 350
Arg Glu Trp Arg Leu Ser Glu Leu Gln Gln Gln Phe Glu Gly Arg Thr
                355                 360                 365
Val Leu Leu Gly Val Asp Asp Met Asp Ile Phe Lys Gly Ile Asn Leu
370                 375                 380
Lys Leu Leu Ala Phe Glu Asn Met Leu Arg Thr His Pro Lys Trp Gln
385                 390                 395                 400
Gly Arg Ala Val Leu Val Gln Ile Ala Asn Pro Ala Arg Gly Arg Gly
                            405                 410                 415
Lys Asp Leu Glu Ala Ile Gln Ala Glu Ile Glu Glu Ser Cys Arg Arg
                            420                 425                 430
Ile Asn Gly Asp Phe Gly Gln Ser Gly Tyr Ser Pro Val Val Phe Ile
                435                 440                 445
Asp Arg Asp Val Ser Ser Val Glu Lys Ile Ala Tyr Tyr Thr Ile Ala
                450                 455                 460
Glu Cys Val Val Val Thr Ala Val Arg Asp Gly Met Asn Leu Thr Pro
465                 470                 475                 480
Tyr Glu Tyr Ile Val Ser Arg Gln Gly Ala Pro Gly Ser Glu Ser Val
                            485                 490                 495
Ser Glu Val Ser Gly Pro Lys Lys Ser Met Leu Val Val Ser Glu Phe
                500                 505                 510
Ile Gly Cys Ser Pro Ser Leu Ser Gly Ala Ile Arg Val Asn Pro Trp
                515                 520                 525
Asn Ile Glu Ala Thr Ala Glu Ala Met Asn Glu Ala Ile Ser Met Pro
                530                 535                 540
Glu Gln Glu Lys Gln Leu Arg His Glu Lys His Tyr Arg Tyr Val Ser
545                 550                 555                 560
Ser His Asp Val Ala Phe Trp Ser Arg Ser Phe Ile Leu Asp Leu Gln
                            565                 570                 575
Arg Ala Cys Gln Asp His Phe Lys Arg Thr Cys Trp Gly Ile Gly Leu
                            580                 585                 590
Gly Phe Gly Phe Arg Val Val Ala Leu Asp Pro His Phe Thr Lys Leu
                595                 600                 605
Asn Met Asp Leu Ile Val Asn Ala Tyr Glu Ile Ser Glu Ser Arg Ala
610                 615                 620
```

Ile Leu Leu Asp Tyr Asp Gly Thr Leu Val Pro Gln Thr Ser Ile Asn
625                 630                 635                 640

Lys Glu Pro Ser Pro Glu Val Leu Ser Ile Ile Asn Thr Leu Cys Ser
            645                 650                 655

Asp Ser Arg Asn Thr Val Phe Leu Val Ser Gly Arg Asp Lys Asp Thr
                660                 665                 670

Leu Gly Lys Trp Phe Ser Ser Cys Pro Lys Leu Gly Ile Ala Ala Glu
            675                 680                 685

His Gly Tyr Phe Leu Arg Trp Ser Arg Glu Glu Trp Gln Thr Cys
            690                 695                 700

Thr Gln Ala Leu Asp Phe Gly Trp Met Gln Met Ala Arg Pro Val Met
705                 710                 715                 720

Asn Leu Tyr Thr Glu Ala Thr Asp Gly Ser Tyr Ile Glu Thr Lys Glu
                725                 730                 735

Ser Ala Leu Val Trp His His Gln Asp Ala Asp Pro Gly Phe Gly Ser
            740                 745                 750

Ser Gln Ala Lys Glu Met Leu Asp His Leu Glu Ser Val Leu Ala Asn
            755                 760                 765

Glu Pro Val Ser Val Lys Ser Gly Gln Phe Ile Val Glu Val Lys Pro
770                 775                 780

Gln Gly Val Thr Lys Gly Ile Val Ala Glu Arg Ile Leu Ala Ser Val
785                 790                 795                 800

Lys Glu Arg Gly Lys Gln Ala Asp Phe Val Leu Cys Ile Gly Asp Asp
            805                 810                 815

Arg Ser Asp Glu Asp Met Phe Glu Asn Ile Ala Asp Ile Ile Asn Arg
            820                 825                 830

Asn Val Val Asp Pro Arg Thr Ser Leu Phe Ala Cys Thr Val Gly Gln
            835                 840                 845

Lys Pro Ser Lys Ala Lys Phe Tyr Leu Asp Asp Thr Phe Glu Val Val
850                 855                 860

Thr Met Leu Ser Ala Leu Ala Asp Ala Thr Gly Pro Glu Leu Glu Thr
865                 870                 875                 880

Asp Ser Ala Asp Glu Leu Ala Ala Ser Ile Ser Ser Leu Asp Ile Gly
            885                 890                 895

Asp Glu Gln Ser Glu Ser Ser Asp Arg Pro Ile Gly Gly Ser
            900                 905                 910

<210> SEQ ID NO 22
<211> LENGTH: 19
<212> TYPE: PRT
<213> ORGANISM: Arabidopsis thaliana

<400> SEQUENCE: 22

Thr Ile Glu Tyr Met Asp Leu Ala Glu Gln Ser Leu Gln Ala Leu Lys
1               5                   10                  15

Lys Ile Ser

<210> SEQ ID NO 23
<211> LENGTH: 31
<212> TYPE: PRT
<213> ORGANISM: Arabidopsis thaliana

<400> SEQUENCE: 23

Glu His Pro Thr Ala Cys Leu Arg Ala Gly Ala Leu Met Ala Val Leu
1               5                   10                  15

```
Ser Tyr Leu Asp Phe Phe Ser Thr Gly Val Gln Arg Val Ala Leu
            20                  25                  30
```

<210> SEQ ID NO 24
<211> LENGTH: 23
<212> TYPE: PRT
<213> ORGANISM: Arabidopsis thaliana

<400> SEQUENCE: 24

```
Ala Asp Asp Leu Pro Ser Val Met Thr Cys Ala Asn Tyr Leu Lys
1               5                   10                  15

Leu Pro Pro Tyr Ser Thr Lys
            20
```

<210> SEQ ID NO 25
<211> LENGTH: 25
<212> TYPE: PRT
<213> ORGANISM: Arabidopsis thaliana

<400> SEQUENCE: 25

```
Gly Arg Leu Gln Arg Gln Lys Val Arg Val Ser Arg Asn Arg Ile Leu
1               5                   10                  15

Asp Ser Ala Ala Lys Val Met Glu Met
            20                  25
```

<210> SEQ ID NO 26
<211> LENGTH: 26
<212> TYPE: PRT
<213> ORGANISM: Arabidopsis thaliana

<400> SEQUENCE: 26

```
Ala Val Leu Glu Val Glu Tyr Phe Gly Glu Val Gly Thr Gly Leu Gly
1               5                   10                  15

Pro Thr Leu Glu Phe Tyr Thr Leu Leu Ser
            20                  25
```

<210> SEQ ID NO 27
<211> LENGTH: 1877
<212> TYPE: PRT
<213> ORGANISM: Zea mays

<400> SEQUENCE: 27

```
Met Glu Thr Arg Ser Arg Lys Arg Ala Glu Ala Ser Ser Ser Ser Ala
1               5                   10                  15

Thr Ser Ser Ser Arg Ser Ser Lys Arg Ser Arg His Asn Pro Asn Pro
            20                  25                  30

Asn Pro Pro Ala Gly Pro Ser Pro Ala Pro Lys Leu Val Pro Leu Pro
        35                  40                  45

Pro Arg Thr Arg Arg Ser Thr Ala Val Asn Pro Leu Pro Pro Met Asp
    50                  55                  60

Ser Ser Gly Asp Asn Asn Ser Asn Pro Val Pro Pro Arg Arg Arg
65                  70                  75                  80

Gly Arg Pro Ser Asn Thr Asp Lys Gly Lys Glu Gln Gln Gln Pro Glu
                85                  90                  95

Pro Ser His Ser Ser Arg Val Arg Glu Ala Glu Arg Leu Leu Gly Leu
            100                 105                 110

Gly Phe Glu Gly Ile Asp Asp Asp Glu Asp Ser Gly Phe Gly Ala Gly
        115                 120                 125

Ala Ile Pro His Ser Leu Thr Ser Ala Ser Thr Ala Leu Gln Gly Leu
    130                 135                 140
```

```
Leu Arg Lys Leu Gly Ala Gly Leu Asp Asp Ile Leu Pro Ser Ser Ala
145                 150                 155                 160

Leu Ser Ala Ala Ala Ala Ala Ser Ser Ser Ala Ser Gly Gln
            165                 170                 175

Leu Ser Gly Arg Leu Lys Asn Ile Leu Ala Gly Leu Arg Ala Asp Gly
                180                 185                 190

Glu Asp Gly Arg Gln Val Glu Ala Leu Thr Gln Leu Cys Glu Met Leu
            195                 200                 205

Ser Ile Gly Thr Glu Glu Ser Leu Gly Ala Phe Ser Val Asp Ser Phe
        210                 215                 220

Val Pro Val Leu Val Gly Leu Leu Asn His Glu Ser Asn Pro Asp Ile
225                 230                 235                 240

Met Leu Leu Ala Ala Arg Ala Leu Thr His Leu Cys Asp Val Leu Pro
                245                 250                 255

Ser Ser Cys Ser Ala Val Val His Tyr Gly Ala Val Pro Cys Phe Cys
            260                 265                 270

Ala Arg Leu Leu Thr Ile Glu Tyr Met Asp Leu Ala Glu Gln Ser Leu
            275                 280                 285

Gln Ala Leu Lys Lys Ile Ser Leu Glu His Pro Thr Ala Cys Leu Arg
            290                 295                 300

Ala Gly Ala Leu Met Ala Val Leu Ser Tyr Leu Asp Phe Phe Ser Thr
305                 310                 315                 320

Gly Val Gln Arg Val Ala Leu Ser Thr Ala Ala Asn Met Cys Arg Lys
                325                 330                 335

Leu Pro Ser Asp Ala Ser Asp Phe Val Met Glu Ala Val Pro Leu Leu
            340                 345                 350

Thr Asn Leu Leu Asn Tyr His Asp Ser Lys Val Leu Glu His Ala Ser
            355                 360                 365

Val Cys Leu Thr Arg Ile Ala Glu Ser Phe Ser Pro Phe Pro Glu Lys
            370                 375                 380

Leu Asp Glu Leu Cys Ser His Gly Leu Val Ala Gln Ala Ala Ser Leu
385                 390                 395                 400

Val Ser Val Ser Asn Ser Ala Gly Gln Ala Ser Leu Ser Thr Ser Thr
                405                 410                 415

Tyr Thr Gly Val Ile Arg Leu Leu Ser Ile Cys Ala Ser Gly Ser Pro
            420                 425                 430

Leu Ala Ala Lys Thr Leu Leu Leu Gly Ile Ser Gly Ile Leu Lys
            435                 440                 445

Asp Ile Leu Ser Gly Ser Gly Leu Val Ala Gly Thr Thr Val Ser Pro
            450                 455                 460

Ala Leu Thr Arg Pro Ala Asp Gln Met Asn Glu Ile Val Lys Leu Ala
465                 470                 475                 480

Asp Glu Leu Leu Pro Ser Leu Pro Val Gly Thr Ile Ser Leu Pro Val
            485                 490                 495

Tyr Ser Gly Val His Met Lys Gly Cys Ser Val Lys Lys Ser Thr Ser
            500                 505                 510

Ser Lys Gln Gly Glu His Gly Ser Thr Ala Asn Glu Leu Ser Gly Arg
            515                 520                 525

Glu Lys Leu Leu Arg Asp Gln Pro Glu Leu Leu Gln Gln Phe Gly Met
            530                 535                 540

Asp Leu Leu Pro Thr Met Thr Gln Val Tyr Gly Ser Ser Val Ser Gly
545                 550                 555                 560
```

-continued

Pro Ile Arg His Arg Cys Leu Ser Val Ile Gly Lys Leu Met Tyr Tyr
          565                 570                 575

Ser Ser Ala Glu Met Ile Gln Ser Leu Leu Ser Thr Thr Asn Ile Ser
        580                 585                 590

Ser Phe Leu Ala Gly Ile Leu Ala Trp Lys Asp Pro Gln Val Leu Ile
    595                 600                 605

Pro Ala Leu Gln Ile Ala Glu Val Leu Met Glu Lys Leu Pro Glu Ile
610                 615                 620

Phe Leu Lys Met Phe Val Arg Glu Gly Val Val His Ala Val Glu Ser
625                 630                 635                 640

Leu Ile Cys Pro Glu Leu Ser Gly Gln Val Thr Pro His Val Asp Ser
                645                 650                 655

Ile Thr Ser Ser His Asn Arg Arg Asn Arg Arg Asn Asn Ala Val
            660                 665                 670

Asn Thr Gly Asn Asn Leu Pro Asp Gly Pro Lys Gly Ser Asn Ser Met
        675                 680                 685

Ile Ala Asn Ser Pro Pro Ser Met Ala Glu Val Pro Asn Asn Ser Leu
        690                 695                 700

Arg Ala Leu Val Ser Asn His Ala Lys Ser Phe Lys Asp Lys Tyr Phe
705                 710                 715                 720

Pro Ser Glu Pro Gly Ser Ser Asp Ile Ala Val Thr Asp Asp Leu Leu
                725                 730                 735

Lys Leu Arg Ala Leu Cys Ala Lys Leu Asn Thr Thr Ala Asp Thr Ile
                740                 745                 750

Lys Thr Lys Ala Lys Gly Lys Ser Lys Val Val Ser Asp Asn Ser Phe
            755                 760                 765

Asp Val Leu Cys Asn Ile Glu Glu Gln Leu Asp Asp Ile Ile Ala Glu
        770                 775                 780

Met Leu Ser Glu Leu Ser Lys Gly Asp Gly Val Ser Thr Phe Glu Phe
785                 790                 795                 800

Ile Gly Ser Gly Val Val Thr Ala Leu Leu Thr Tyr Leu Ser Cys Gly
                805                 810                 815

Thr Phe Gly Arg Glu Lys Val Ser Glu Ala Asn Ile Pro Asn Leu Arg
            820                 825                 830

His Gln Ala Val Arg Arg Tyr Lys Thr Phe Ile Ser Phe Ala Leu Pro
        835                 840                 845

Asn Asp Lys Asp Gly Asn Lys Thr Pro Met Ala Phe Leu Val His Lys
        850                 855                 860

Leu Gln Ser Ala Leu Ser Ser Leu Glu Arg Phe Pro Val Val Leu Ser
865                 870                 875                 880

His Ser Gly Arg Ala Ser Thr Leu Gly Gly Ser Arg Leu Thr Thr Gly
                885                 890                 895

Leu Gly Ser Leu Ser Gln Pro Ile Lys Leu Arg Leu Cys Arg Ala Pro
            900                 905                 910

Gly Glu Lys Ser Leu Lys Asp Phe Ser Asn Val Val Leu Ile Asp
        915                 920                 925

Ser Leu Ala Ser Leu Ala Ala Val Glu Asp Phe Leu Trp Pro Arg Val
    930                 935                 940

Gln Arg Thr Glu Pro Val Leu Lys Pro Pro Met Ser Ser Ala Asn Asn
945                 950                 955                 960

Ser Gly Ser Gly Ala Ala Ser Ser Thr Ala Cys Ala Pro Ser Ile Pro
                965                 970                 975

Ser Glu Thr Gln Ser Val Arg Arg Thr Ser Leu Arg Ser Lys Ser Ser

-continued

```
              980             985             990
Ala Ala Thr Ser Gly Ala Ile Lys  Lys Asp Tyr Gln Glu  Gly Ser Ile
              995            1000            1005
Asn Thr  Ser Lys Gly Lys Gly  Lys Ala Val Leu Lys  Leu Ser Leu
             1010            1015            1020
Asp Glu  Pro Lys Gly Pro His  Thr Arg Asn Ala Ala  Arg Arg Lys
             1025            1030            1035
Ala Thr  Ser Glu Lys Asp Val  Glu Leu Lys Pro Ser  His Gly His
             1040            1045            1050
Ile Thr  Ser Glu Asp Glu Asp  Leu Asp Ala Ser Pro  Val Glu Ile
             1055            1060            1065
Asp Asp  Ala Leu Ile Leu Asp  Asp Asp Glu Asp  Val Pro Asp
             1070            1075            1080
Asp Glu  Asp Asp Asp His Glu  Ala Val Leu Arg Gly  Ser Leu Pro
             1085            1090            1095
Ser Cys  Val Pro Glu Arg Val  His Asp Val Lys Leu  Gly Asp Ala
             1100            1105            1110
Asp Asp  Ser Ser Val Ala Ser  Leu Ala Asn Asp Asn  Gln Ala Gln
             1115            1120            1125
Pro Ser  Ser Gly Ser Ser Thr  Lys Asn Thr Ser Ser  Arg Gly Leu
             1130            1135            1140
Asp Thr  Ala Glu Phe Arg Ser  Pro Ala Thr Phe Gly  Ser Arg Gly
             1145            1150            1155
Ala Met  Ser Phe Ala Ala Ala  Ala Met Ala Gly Leu  Thr Pro Val
             1160            1165            1170
Gly Gly  Arg Gly Ile Arg Gly  Ser Arg Asp Arg Asn  Gly Leu Pro
             1175            1180            1185
Leu Gly  Ala Arg Ala Thr Glu  His Tyr Asn Lys Leu  Ile Phe Thr
             1190            1195            1200
Ala Ala  Gly Lys Gln Leu Asn  Lys His Leu Thr Val  Tyr Gln Ala
             1205            1210            1215
Val Gln  Arg Gln Val Val His  Ala Glu Asp Asp Glu  Asp Arg Phe
             1220            1225            1230
Gly Gly  Ser Asp Leu Pro Asp  Asp Gly Asn His Phe  Trp Asp Asp
             1235            1240            1245
Ile Arg  Gly Asp Val Phe Thr  Ile Thr Tyr Gln Lys  Ala Asp Asn
             1250            1255            1260
Thr Ala  Glu Lys Gly Ser Val  Gly Gly Ser Ala Ser  Val Pro Lys
             1265            1270            1275
Ser Ser  Lys Ser Asp Ser Cys  Arg Thr Leu Ser Glu  Lys Gln Cys
             1280            1285            1290
Thr Ser  Leu Leu Asp Ser Ile  Leu Gln Gly Glu Leu  Pro Cys Asp
             1295            1300            1305
Leu Glu  Lys Ser Asn Gln Thr  Tyr Asn Ile Leu Ser  Leu Leu His
             1310            1315            1320
Val Leu  Glu Gly Leu Asn Gln  Leu Ser Pro Arg Leu  Arg Leu Gln
             1325            1330            1335
Ser Ala  Cys Asp Asp Phe Ala  Glu Gly Lys Val Ala  Thr Leu Asn
             1340            1345            1350
Gly Leu  Tyr Asp Val Gly Ala  Lys Val Pro Ser Lys  Glu Phe Ile
             1355            1360            1365
Asn Ser  Lys Met Thr Pro Lys  Leu Ala Arg Gln Ile  Gln Asp Val
             1370            1375            1380
```

```
Leu Ala Leu Cys Ser Gly Ser Leu Pro Ser Trp Cys Tyr Gln Leu
1385             1390                1395

Thr Lys Ala Cys Pro Phe Leu Phe Pro Phe Glu Thr Arg Arg Gln
1400             1405                1410

Tyr Phe Tyr Ser Thr Ala Phe Gly Leu Ser Arg Ala Leu His Arg
1415             1420                1425

Leu Gln Gln Gln Pro Gly Asn Asp Asn Asn Thr Ala Phe Glu Arg
1430             1435                1440

Glu Val Arg Ile Gly Arg Leu Gln Arg Gln Lys Val Arg Val Ser
1445             1450                1455

Arg Asn Arg Ile Leu Asp Ser Ala Ala Lys Val Met Glu Met Phe
1460             1465                1470

Ser Asn Gln Lys Ala Val Leu Glu Val Glu Tyr Phe Gly Glu Val
1475             1480                1485

Gly Thr Gly Leu Gly Pro Thr Leu Glu Phe Tyr Thr Leu Leu Ser
1490             1495                1500

Arg Glu Leu Gln Arg Val Asp Leu Gly Leu Trp Arg Ser His Ser
1505             1510                1515

Ser Asp Asn Ser Gly Met Gln Ile Asp Ala Asn Ala Asp Asp Leu
1520             1525                1530

Ile Arg Ser Lys Asn His Glu Ser Glu Ser Leu Thr Glu Ser Arg
1535             1540                1545

Asn Ile Val Gln Ser Pro Leu Gly Leu Phe Pro Gln Pro Trp Pro
1550             1555                1560

Pro Thr Ala Ala Ala Ser Glu Gly Ser Lys Phe Phe Lys Val Val
1565             1570                1575

Glu Tyr Phe Arg Leu Val Gly Arg Val Met Ala Lys Ala Leu Gln
1580             1585                1590

Asp Gly Arg Leu Leu Asp Leu Pro Leu Ser Thr Ala Phe Tyr Lys
1595             1600                1605

Leu Leu Leu Gly Gln Glu Leu Asp Leu Tyr Asp Ile Leu Ser Phe
1610             1615                1620

Asp Thr Glu Phe Gly Lys Thr Leu Gln Glu Leu Gln Ile Leu Val
1625             1630                1635

Ala Arg Lys Gln Phe Leu Asp Ser Cys Ser Ser Glu Ser Gln Lys
1640             1645                1650

Ile Asp Leu Cys Phe Arg Gly Ala Pro Val Glu Asp Leu Tyr Leu
1655             1660                1665

Asp Phe Thr Leu Pro Gly Tyr Pro Glu Tyr Val Leu Lys Glu Gly
1670             1675                1680

Gly Glu Asn Ala Glu Val Asn Ile Cys Asn Leu Glu Glu Tyr Ile
1685             1690                1695

Ser Leu Val Val Asp Ala Thr Val Lys Thr Gly Ile Met Arg Gln
1700             1705                1710

Val Glu Ala Phe Lys Ala Gly Phe Asn Gln Val Phe Asp Ile Ser
1715             1720                1725

Ser Leu Gln Ile Phe Ser Pro Gln Glu Leu Asp Tyr Leu Ile Cys
1730             1735                1740

Gly Arg Cys Glu Leu Trp Glu Pro Glu Thr Leu Pro Glu His Ile
1745             1750                1755

Lys Phe Asp His Gly Tyr Thr Ser Lys Ser Pro Ala Ile Ile Asn
1760             1765                1770
```

```
Phe Leu Glu Ile Met Ala Glu Phe Thr Pro Glu Gln Gln His Ala
    1775                1780                1785

Phe Cys Gln Phe Val Thr Gly Ala Pro Arg Leu Pro Pro Gly Gly
    1790                1795                1800

Leu Ala Ala Leu Asn Pro Lys Leu Thr Ile Val Arg Lys His Ser
    1805                1810                1815

Ser Val Ala Asn Asn Ser Asn Ala Thr Gly Ala Thr Glu Ser
    1820                1825                1830

Ala Asp Asp Asp Leu Pro Ser Val Met Thr Cys Ala Asn Tyr Leu
    1835                1840                1845

Lys Leu Pro Pro Tyr Ser Thr Lys Ala Ile Met Leu Lys Lys Leu
    1850                1855                1860

Leu Tyr Ala Ile Asn Glu Gly Gln Gly Ser Phe Asp Leu Ser
    1865                1870                1875

<210> SEQ ID NO 28
<211> LENGTH: 1896
<212> TYPE: PRT
<213> ORGANISM: Vitis vinifera

<400> SEQUENCE: 28

Met Glu Thr Arg Ser Arg Lys Arg Ala Glu Ala Ser Ser Ala Ala Pro
1               5                   10                  15

Ser Ser Gly Pro Thr Thr Arg Ser Ser Lys Arg Pro Arg Ile Ser Ser
                20                  25                  30

Ser Ser Ser Ser Thr Ile Pro Ile Ser Ser Ile Ser Thr Arg Ser Arg
                35                  40                  45

Val Ser Arg Ser Gln Asp Ser Leu Ala Ser Ser Thr Pro Met Asp Ser
50                  55                  60

Thr Asn Glu Ser Ser Gly Ser Ala Ala Arg Gly Arg Gly Arg Asn
65                  70                  75                  80

Gln Gly Gly Asp Lys Asp Asn Ser Asp Lys Gly Lys Glu Lys Glu His
                85                  90                  95

Glu Val Arg Val Arg Asp Arg Asp Arg Asp Arg Asp Arg Glu
                100                 105                 110

Ala Ala Glu Arg Ala Leu Gly Leu Asn Ile Asp Gly Gly Gly Gly
                115                 120                 125

Asp Asp Asp Asp Asn Asp Ser Glu Gly Gly Ala Gly Ile Leu His Gln
130                 135                 140

Asn Phe Thr Ser Ala Ser Ser Ala Leu Gln Gly Leu Leu Arg Lys Leu
145                 150                 155                 160

Gly Ala Gly Leu Asp Asp Leu Leu Pro Ser Ser Ala Met Gly Ser Ala
                165                 170                 175

Ser Ser Ser His Gln Ser Gly Arg Leu Lys Lys Ile Leu Ser Gly Leu
                180                 185                 190

Arg Ala Asp Gly Glu Glu Gly Arg Gln Val Glu Ala Leu Thr Gln Leu
                195                 200                 205

Cys Glu Met Leu Ser Ile Gly Thr Glu Glu Leu Ser Thr Phe Ser
            210                 215                 220

Val Asp Ser Phe Val Pro Val Leu Val Gly Leu Leu Asn His Glu Ser
225                 230                 235                 240

Asn Pro Asp Ile Met Leu Leu Ala Ala Arg Ala Leu Thr His Leu Cys
                245                 250                 255

Asp Val Leu Pro Ser Ser Cys Ala Ala Val Val His Tyr Gly Ala Val
                260                 265                 270
```

```
Ser Cys Phe Cys Ala Arg Leu Leu Thr Ile Glu Tyr Met Asp Leu Ala
    275                 280                 285

Glu Gln Ser Leu Gln Ala Leu Lys Lys Ile Ser Gln Glu His Pro Thr
290                 295                 300

Ala Cys Leu Arg Ala Gly Ala Leu Met Ala Val Leu Ser Tyr Leu Asp
305                 310                 315                 320

Phe Phe Ser Thr Gly Val Gln Arg Val Ala Leu Ser Thr Ala Ala Asn
                325                 330                 335

Met Cys Lys Lys Leu Pro Ser Asp Ala Ala Asp Phe Val Met Glu Ala
                340                 345                 350

Val Pro Leu Leu Thr Asn Leu Leu Gln Tyr His Asp Ala Lys Val Leu
                355                 360                 365

Glu His Ala Ser Val Cys Leu Thr Arg Ile Ala Glu Ala Phe Ala Ser
    370                 375                 380

Ser Pro Asp Lys Leu Asp Glu Leu Cys Asn His Gly Leu Val Asp Gln
385                 390                 395                 400

Ala Ala Ser Leu Ile Ser Thr Ser Asn Ser Gly Gly Gln Ala Ser
                405                 410                 415

Leu Ser Thr Pro Thr Tyr Thr Gly Leu Ile Arg Leu Leu Ser Thr Cys
                420                 425                 430

Ala Ser Gly Ser Pro Leu Gly Ala Lys Thr Leu Leu Leu Leu Gly Ile
                435                 440                 445

Ser Gly Ile Leu Lys Asp Ile Leu Ser Gly Ser Gly Leu Val Ala Ser
                450                 455                 460

Ile Ser Val Ser Pro Ala Ile Ser Arg Pro Pro Glu Gln Ile Phe Glu
465                 470                 475                 480

Ile Val Asn Leu Ala Asn Glu Leu Leu Pro Pro Leu Pro Glu Gly Ile
                485                 490                 495

Ile Ser Leu Pro Ala Ser Ser Asn Leu Leu Val Lys Gly Thr Leu Val
                500                 505                 510

Lys Lys Ala Pro Ser Ser Ser Gly Lys Gln Glu Asp Val Asn Gly
                515                 520                 525

Asn Val Pro Glu Val Ser Ala Arg Glu Lys Leu Leu Asn Asp Gln Pro
                530                 535                 540

Glu Leu Leu Gln Gln Phe Gly Met Asp Leu Leu Pro Val Leu Ile Gln
545                 550                 555                 560

Ile Tyr Gly Ser Ser Val Asn Gly Pro Val Arg His Lys Cys Leu Ser
                565                 570                 575

Val Ile Gly Lys Leu Met Tyr Phe Ser Thr Ala Asp Met Ile Gln Ser
                580                 585                 590

Leu Ile Ser Val Thr Asn Ile Ser Ser Phe Leu Ala Gly Val Leu Ala
                595                 600                 605

Trp Lys Asp Pro Gln Val Leu Val Pro Ala Leu Gln Ile Ala Glu Ile
                610                 615                 620

Leu Met Glu Lys Leu Pro Gly Thr Phe Ser Lys Met Phe Val Arg Glu
625                 630                 635                 640

Gly Val Val His Ala Ile Asp Thr Leu Ile Leu Ala Gly Ser Gln Asn
                645                 650                 655

Ala Val Ser Val Gln Pro Ser Ser Asn Glu Lys Asp Asn Asp Ser Ile
                660                 665                 670

Thr Gly Thr Ser Arg Ser Arg Arg Tyr Arg Lys Arg Gly Gly Asn Pro
                675                 680                 685
```

```
Asn Pro Asp Ala Asn Ser Leu Glu Glu Pro Lys Thr Ser Val Ser Val
    690                 695                 700
Thr Ile Gly Ser Pro Pro Ser Val Glu Ile Pro Thr Ser Asn Ser
705                 710                 715                 720
Asn Leu Arg Thr Thr Val Ser Ala Cys Ala Lys Ala Phe Lys Asp Lys
                725                 730                 735
Tyr Phe Pro Ser Asp Pro Gly Cys Ala Glu Ala Gly Val Thr Asp Asp
            740                 745                 750
Leu Leu His Leu Lys Asn Leu Cys Met Arg Leu Ser Ser Gly Ile Asp
        755                 760                 765
Asp His Lys Thr Lys Ala Lys Gly Lys Ser Lys Ala Ser Gly His Arg
    770                 775                 780
Leu Ile Asp Thr Ser Thr Asn Lys Glu Glu Asn Leu Thr Ala Val Leu
785                 790                 795                 800
Ser Glu Met Leu Ala Glu Leu Ser Lys Gly Asp Gly Val Ser Thr Phe
                805                 810                 815
Glu Phe Ile Gly Ser Gly Val Val Ala Ala Leu Leu Asn Tyr Phe Ser
            820                 825                 830
Cys Gly His Phe Ser Lys Glu Arg Ile Ser Glu Ala Asn Leu Ser Lys
        835                 840                 845
Phe Arg Thr Gln Ala Leu Lys Arg Phe Lys Ser Phe Val Ala Ile Ala
    850                 855                 860
Leu Pro Ser Asn Ile Asp Gly Arg Asn Ala Ala Pro Met Thr Val Leu
865                 870                 875                 880
Val Gln Lys Leu Gln Asn Ala Leu Ser Ser Leu Glu Arg Phe Pro Val
                885                 890                 895
Val Leu Ser His Ser Ser Arg Ser Ser Ser Gly Asn Ala Arg Leu Ser
            900                 905                 910
Ser Gly Leu Ser Ala Leu Ser Gln Pro Phe Lys Leu Arg Leu Cys Arg
        915                 920                 925
Ala Gln Gly Glu Lys Ser Leu Arg Asp Tyr Ser Ser Asn Val Val Leu
    930                 935                 940
Ile Asp Pro Leu Ala Ser Leu Ala Ala Val Glu Asp Phe Leu Trp Pro
945                 950                 955                 960
Arg Val Gln Arg Gly Asp Thr Gly Gln Lys Pro Ser Ala Ser Ala Gly
                965                 970                 975
Asn Ser Glu Ser Gly Thr Thr Pro Thr Gly Ala Gly Ala Ser Ser Pro
            980                 985                 990
Ser Thr Ser Thr Pro Ala Ser Thr  Ala Arg Arg His Ser  Thr Arg Ser
        995                 1000                1005
Arg Thr  Ser Val Asn Ile Ala  Asp Thr Ala Arg Lys  Glu Pro Pro
    1010                1015                1020
Leu Glu  Lys Thr Pro Ser Ser  Ser Lys Gly Lys Gly  Lys Ala Val
    1025                1030                1035
Leu Lys  Pro Ala Gln Glu Asp  Ala Arg Gly Pro Gln  Thr Arg Asn
    1040                1045                1050
Ala Ala  Arg Arg Arg Ala Ser  Leu Asp Lys Asp Ala  Gln Leu Lys
    1055                1060                1065
Pro Val  Gly Asp Ser Ser Ser  Glu Asp Glu Glu Leu  Asp Ile Ser
    1070                1075                1080
Pro Val  Glu Ile Asp Asp Ala  Leu Val Ile Glu Asp  Asp Asp Ile
    1085                1090                1095
Ser Asp  Asp Glu Asp Asp Asp  His Asp Asp Val Leu  Arg Asp Asp
```

```
            1100                1105                1110
Ser Leu Pro Val Cys Met Pro Asp Lys Val His Asp Val Lys Leu
        1115                1120                1125
Gly Asp Ser Ala Glu Asp Ser Asn Asn Ala Pro Ala Thr Ser Asp
        1130                1135                1140
Ser Gln Thr Asn Ala Ala Ser Gly Ser Ser Arg Ala Ala Ala
        1145                1150                1155
Val Lys Gly Leu Asp Ser Thr Glu Phe Arg Ser Gly Asn Ser Phe
        1160                1165                1170
Gly Ser Arg Gly Ala Met Ser Phe Ala Ala Ala Met Ala Gly
        1175                1180                1185
Leu Ala Ser Ala Asn Gly Arg Gly Ile Arg Gly Gly Arg Asp Arg
        1190                1195                1200
His Gly Arg Pro Leu Phe Gly Ser Ser Asp Pro Arg Leu Ile
        1205                1210                1215
Phe Ser Ala Gly Gly Lys Gln Leu Asn Arg His Leu Thr Ile Tyr
        1220                1225                1230
Gln Ala Ile Gln Arg Gln Leu Val Leu Asp Glu Asp Asp Glu
        1235                1240                1245
Arg Tyr Asn Gly Ser Asp Phe Ile Ser Ser Asp Gly Ser Arg Leu
        1250                1255                1260
Trp Ser Asp Ile Tyr Thr Ile Thr Tyr Gln Arg Ala Asp Ala Gln
        1265                1270                1275
Ala Asp Arg Ala Leu Val Gly Gly Ser Ser Ala Thr Gln Ser
        1280                1285                1290
Arg Ser Thr Arg Ala Gly Ser Gly Ser Ser Ser Asn Thr Asp Met
        1295                1300                1305
Ser Leu His Arg Met Ser Leu Leu Asp Ser Ile Leu Gln Gly Glu
        1310                1315                1320
Leu Pro Cys Asp Leu Glu Lys Ser Asn Pro Thr Tyr Asn Ile Met
        1325                1330                1335
Ala Leu Leu Arg Val Leu Glu Gly Leu Asn Gln Leu Ala Pro Arg
        1340                1345                1350
Leu Arg Val Gln Ala Val Ser Asp Asp Phe Ser Glu Gly Lys Ile
        1355                1360                1365
Ser Cys Leu Asp Glu Leu Ser Ala Thr Gly Ala Arg Val Pro Tyr
        1370                1375                1380
Glu Glu Phe Ile Asn Ser Lys Leu Thr Pro Lys Leu Ala Arg Gln
        1385                1390                1395
Ile Gln Asp Ala Leu Ala Leu Cys Ser Gly Ser Leu Pro Ser Trp
        1400                1405                1410
Cys Tyr Gln Val Thr Lys Ala Cys Pro Phe Leu Phe Pro Phe Glu
        1415                1420                1425
Thr Arg Arg Gln Tyr Phe Tyr Ser Thr Ala Phe Gly Leu Ser Arg
        1430                1435                1440
Ala Leu Tyr Arg Leu Gln Gln Gln Gln Gly Ala Asp Gly His Gly
        1445                1450                1455
Ser Thr Asn Glu Arg Ile Gly Arg Leu Gln Arg Gln Lys Val Arg
        1460                1465                1470
Val Ser Arg Asn Arg Ile Leu Asp Ser Ala Ala Lys Val Met Glu
        1475                1480                1485
Met Tyr Ser Ser Gln Lys Ala Val Leu Glu Val Glu Tyr Phe Gly
        1490                1495                1500
```

```
Glu Val Gly Thr Gly Leu Gly Pro Thr Leu Glu Phe Tyr Thr Leu
    1505                1510                1515

Leu Ser His Asp Leu Gln Lys Val Gly Leu Gly Met Trp Arg Ser
    1520                1525                1530

Asn Phe Ser Pro Asp Lys Gln Ser Met Glu Ile Asp Gly Asp Glu
    1535                1540                1545

Leu Lys Asn Gly Lys Thr Asp Asn Ile Ser Arg Leu Ser Pro Ala
    1550                1555                1560

Ala Ser Asp Ile Val Gln Ala Pro Leu Gly Leu Phe Pro Arg Pro
    1565                1570                1575

Trp Pro Pro Asn Ala Asp Ala Ser Asp Gly Ser Gln Phe Ser Lys
    1580                1585                1590

Val Ile Glu His Phe Arg Leu Val Gly Arg Val Ile Ala Lys Ala
    1595                1600                1605

Leu Gln Asp Gly Arg Leu Leu Asp Leu Pro Leu Ser Thr Ala Leu
    1610                1615                1620

Tyr Lys Leu Val Leu Gly Gln Glu Leu Asp Leu His Asp Ile Leu
    1625                1630                1635

Ser Phe Asp Ala Asp Phe Gly Lys Ile Leu Gln Glu Leu Gln Val
    1640                1645                1650

Leu Val Ser Arg Lys Gln Tyr Leu Glu Ser Thr Gly Gly Asp Asn
    1655                1660                1665

Gln Asp Ala Ile Ala Asn Leu Cys Phe Arg Gly Ala Pro Ile Glu
    1670                1675                1680

Asp Leu Cys Leu Asp Phe Thr Leu Pro Gly Tyr Pro Asp Tyr Ile
    1685                1690                1695

Leu Lys Pro Gly Glu Glu Asn Val Asp Ile Asn Asn Leu Glu Glu
    1700                1705                1710

Tyr Ile Ser Leu Val Val Asp Ala Thr Val Lys Thr Gly Ile Met
    1715                1720                1725

Arg Gln Met Glu Ala Phe Arg Ser Gly Phe Asn Gln Val Phe Asp
    1730                1735                1740

Ile Thr Ser Leu Gln Ile Phe Ser Pro Asp Glu Leu Asp Tyr Leu
    1745                1750                1755

Leu Cys Gly Arg Arg Glu Leu Trp Glu Ala Glu Thr Leu Val Asp
    1760                1765                1770

His Ile Lys Phe Asp His Gly Tyr Thr Ala Lys Ser Pro Ala Ile
    1775                1780                1785

Ile Asn Leu Leu Glu Ile Met Gly Glu Phe Asn Pro Glu Gln Gln
    1790                1795                1800

Arg Ala Phe Cys Gln Phe Val Thr Gly Ala Pro Arg Leu Pro Pro
    1805                1810                1815

Gly Gly Leu Ala Val Leu Asn Pro Lys Leu Thr Ile Val Arg Lys
    1820                1825                1830

His Ser Ser Ser Thr Val Ser Thr Ala Ala Asn Gly Ser Ser Gly
    1835                1840                1845

Pro Ser Glu Ser Ala Asp Asp Asp Leu Pro Ser Val Met Thr Cys
    1850                1855                1860

Ala Asn Tyr Leu Lys Leu Pro Pro Tyr Ser Thr Lys Glu Ile Met
    1865                1870                1875

Tyr Lys Lys Leu Leu Tyr Ala Ile Ser Glu Gly Gln Gly Ser Phe
    1880                1885                1890
```

Asp Leu Ser
    1895

<210> SEQ ID NO 29
<211> LENGTH: 1895
<212> TYPE: PRT
<213> ORGANISM: Populus trichocarpa

<400> SEQUENCE: 29

Met Glu Thr Arg Ser Arg Lys Arg Ala Glu Ala Ser Ser Ser Ala Ala
1               5                   10                  15

Thr Asn Thr Thr Gly Thr Thr Thr Arg Ser Asn Lys Arg Ser Arg Thr
            20                  25                  30

Asn Ala Ala Thr Ala Thr Ala Thr Thr Thr Ala Thr Ala Thr Arg
        35                  40                  45

Ser Arg Ser Thr Arg Ala His Pro Leu Pro Met Asp Ser Thr Pro Val
    50                  55                  60

Glu Ser Ser Ser Ser Arg Ser Arg Arg Asn Arg Asn Asn Asn Ser
65                  70                  75                  80

Asn Ser Glu Ser Glu Lys Gly Lys Glu Lys Glu His Glu Val Arg Val
                85                  90                  95

Ser Arg Glu Asn Arg Glu Ile Thr Asn Asn Leu Asp Ser Gly Asn Asp
            100                 105                 110

Asn Asn Asn Pro Asn Val Asp Asp Asp Asp Asp Asp Ser Glu Gly
        115                 120                 125

Gly Gly Ile Ala Ala Phe His Gln Asn Leu Thr Ser Ala Ser Ser Ala
    130                 135                 140

Leu Gln Gly Leu Leu Arg Lys Leu Gly Ala Gly Leu Asp Asp Leu Leu
145                 150                 155                 160

Pro Ser Pro Val Met Gly Ser Gly Ser Ser His Gln Ser Gly Arg
                165                 170                 175

Leu Lys Lys Ile Leu Ser Gly Leu Arg Ala Asp Gly Glu Glu Gly Lys
            180                 185                 190

Gln Val Glu Ala Leu Thr Gln Leu Cys Glu Met Leu Ser Ile Gly Thr
        195                 200                 205

Glu Glu Ser Leu Ser Thr Phe Ser Val Asp Ser Phe Val Pro Val Leu
    210                 215                 220

Val Gly Leu Leu Asn Asn Glu Ser Asn Pro Asp Ile Met Leu Leu Ala
225                 230                 235                 240

Ala Arg Ala Ile Thr His Leu Cys Asp Val Leu Pro Ser Ser Cys Ala
                245                 250                 255

Ala Val His Tyr Gly Ala Val Ser Cys Phe Val Ala Arg Leu Ile
            260                 265                 270

Thr Ile Glu Tyr Met Asp Leu Ala Glu Gln Ser Leu Gln Ala Leu Lys
        275                 280                 285

Lys Ile Ser Gln Glu His Pro Thr Ala Cys Leu Arg Ala Gly Ala Leu
    290                 295                 300

Met Ala Val Leu Ser Tyr Leu Asp Phe Phe Ser Thr Gly Val Gln Arg
305                 310                 315                 320

Val Ala Leu Ser Thr Ala Ala Asn Met Cys Lys Lys Leu Pro Ser Asp
                325                 330                 335

Ala Ala Asp Phe Val Met Glu Ala Val Pro Leu Leu Thr Asn Leu Leu
            340                 345                 350

Gln Tyr His Asp Ala Lys Val Leu Glu His Ala Ser Val Cys Leu Thr
        355                 360                 365

```
Arg Ile Ala Glu Ala Phe Ala Ser Ser Pro Asp Lys Leu Asp Glu Leu
    370                 375                 380
Cys Asn His Gly Leu Val Thr Gln Ala Ser Leu Ile Ser Thr Ser
385                 390                 395                 400
Ser Ser Gly Gly Gly Gln Ala Ser Leu Ser Thr Pro Thr Tyr Thr Gly
                405                 410                 415
Leu Ile Arg Leu Leu Ser Thr Cys Ala Ser Gly Ser Pro Leu Gly Ala
            420                 425                 430
Lys Thr Leu Leu Leu Leu Gly Val Ser Gly Ile Leu Lys Glu Ile Leu
        435                 440                 445
Ser Gly Ser Gly Val Ser Ala Asn Ser Pro Val Pro Ala Leu Ser
    450                 455                 460
Arg Pro Ala Asp Gln Ile Phe Glu Ile Val Asn Leu Ala Asn Glu Leu
465                 470                 475                 480
Leu Pro Pro Leu Pro Gln Gly Thr Ile Ser Leu Pro Thr Ser Ser Ser
                485                 490                 495
Met Leu Val Lys Gly Ser Val Val Lys Lys Cys Pro Ser Ser Ser Ser
            500                 505                 510
Gly Lys Gln Asp Ile Asn Gly Asn Val Pro Glu Val Ser Ala Arg
    515                 520                 525
Glu Lys Leu Leu Asn Asp Gln Pro Glu Leu Leu Gln Gln Phe Gly Met
530                 535                 540
Asp Leu Leu Pro Val Leu Ile Gln Ile Tyr Gly Ser Ser Val Asn Ser
545                 550                 555                 560
Pro Val Arg His Lys Cys Leu Ser Val Ile Gly Lys Leu Met His Phe
                565                 570                 575
Ser Asn Ala Glu Met Ile Gln Ser Leu Leu Ser Met Thr Asn Ile Ser
            580                 585                 590
Ser Phe Leu Ala Gly Val Leu Ala Trp Lys Asp Pro His Val Leu Val
    595                 600                 605
Pro Ala Leu Gln Val Ala Glu Ile Leu Met Glu Lys Leu Pro Gly Thr
610                 615                 620
Phe Ser Lys Ile Phe Val Arg Glu Gly Val Val Tyr Ala Val Asp Gln
625                 630                 635                 640
Leu Ile Leu Ala Gly Asn Pro Asn Thr Ala Pro Thr His Gly Ser Ser
                645                 650                 655
Ala Glu Lys Asp Asn Glu Ser Val Pro Gly Thr Ser Ser Arg Ser Arg
            660                 665                 670
Arg Tyr Lys Arg Arg Ser Gly Ser Ser Asn Pro Glu Ala Asn Ser Ser
        675                 680                 685
Glu Glu Ser Lys Asn Pro Ile Ser Ala Asn Ala Gly Ser Pro Pro Ser
    690                 695                 700
Ser Ile Glu Ile Pro Met Val Asn Ser Asn Leu Arg Met Ala Val Ser
705                 710                 715                 720
Ala Cys Ala Lys Ala Phe Arg Asp Lys Tyr Phe Pro Ser Asp Pro Gly
                725                 730                 735
Ala Ala Glu Asp Gly Val Thr Asp Asp Leu Leu His Leu Lys Asn Leu
            740                 745                 750
Cys Thr Lys Leu Asn Ala Gly Val Asp Asp Gln Lys Thr Lys Ala Lys
        755                 760                 765
Gly Lys Ser Lys Ala Ser Ala Ser Arg Leu Ile Asp Ser Ser Thr Asn
    770                 775                 780
```

```
Lys Glu Glu Tyr Leu Ile Gly Val Ile Ser Glu Met Leu Ala Glu Leu
785                 790                 795                 800

Gly Lys Gly Asp Gly Val Ser Thr Phe Glu Phe Ile Gly Ser Gly Val
            805                 810                 815

Val Ala Thr Leu Leu Asn Phe Phe Ser Cys Gly Tyr Ser Thr Lys Glu
        820                 825                 830

Lys Ile Ser Glu Ala Asn Leu Pro Lys Leu Arg Gln Gln Ala Leu Arg
            835                 840                 845

Arg Phe Lys Ser Phe Ala Ile Leu Ala Leu Pro Ser Ser Ile Asp Glu
    850                 855                 860

Gly Gly Ala Ala Pro Met Ala Val Leu Val Gln Lys Leu Gln Asn Ala
865                 870                 875                 880

Leu Ser Ser Leu Glu Arg Phe Pro Val Val Leu Ser His Ser Ser Arg
                885                 890                 895

Ser Ser Ser Gly Gly Ala Arg Leu Ser Ser Gly Leu Ser Ala Leu Ser
            900                 905                 910

Gln Pro Phe Lys Leu Arg Leu Cys Arg Ala Gln Gly Glu Lys Ala Leu
        915                 920                 925

Arg Asp Tyr Ser Ser Asn Val Val Leu Ile Asp Pro Leu Ala Ser Leu
    930                 935                 940

Ala Ala Val Glu Glu Phe Leu Trp Pro Arg Val Gln Arg Ser Glu Thr
945                 950                 955                 960

Gly His Lys Ala Ser Ala Ser Ala Gly Asn Ser Glu Ser Gly Asn Ala
                965                 970                 975

Gln Pro Gly Ala Gly Ala Ser Ser Pro Ser Thr Ser Ile Pro Ala Ser
            980                 985                 990

Ala Thr Arg Arg His Ser Ser Arg  Ser Arg Ser Ser Val  Asn Ile Gly
            995                 1000                 1005

Asp Ser  Ala Arg Lys Glu Pro  Ile Pro Glu Lys Ser  Thr Ser Thr
    1010                 1015                 1020

Ser Thr  Ser Lys Gly Lys Gly  Lys Ala Val Leu Lys  Pro Pro Leu
    1025                 1030                 1035

Glu Glu  Thr Lys Gly Pro Gln  Thr Arg Asn Ala Ala  Arg Arg Arg
    1040                 1045                 1050

Ala Ala  Ile Asp Lys Asp Ala  Gln Met Lys Pro Val  His Gly Asp
    1055                 1060                 1065

Ser Ser  Ser Glu Asp Glu Glu  Leu Asp Ile Ser Pro  Val Glu Ile
    1070                 1075                 1080

Asp Asp  Ala Leu Val Ile Glu  Asp Asp Asp Ile Ser  Asp Asp Asp
    1085                 1090                 1095

Asp Asp  Asp Asp Asp Asp His  Glu Asp Val Leu Arg  Asp Asp Ser
    1100                 1105                 1110

Leu Pro  Val Cys Met Pro Glu  Lys Val His Asp Val  Lys Leu Gly
    1115                 1120                 1125

Ala Ala  Ser Glu Asp Ser Asn  Val Ala Pro Pro Ala  Ser Asp Ser
    1130                 1135                 1140

Gln Ser  Asn Pro Ala Ser Gly  Ser Ser Ser Arg Ala  Val Ala Val
    1145                 1150                 1155

Arg Gly  Ser Asp Ser Thr Asp  Phe Arg Ser Gly Ser  Ser Tyr Gly
    1160                 1165                 1170

Ser Arg  Gly Ala Met Ser Phe  Ala Ala Ala Ala Met  Ala Gly Leu
    1175                 1180                 1185

Gly Ser  Ala Asn Gly Arg Gly  Ile Arg Gly Gly Arg  Asp Arg Gln
```

-continued

```
            1190                1195                1200
Gly Arg Pro Leu Phe Gly Ser Ser Asp Pro Lys Leu Ile
    1205                1210                1215
Phe Thr Ala Ala Gly Lys Gln Leu Asn Arg His Leu Thr Ile Tyr
    1220                1225                1230
Gln Ala Ile Gln Arg Gln Leu Val Leu Glu Glu Asp Asp Glu Asp
    1235                1240                1245
Arg Tyr Gly Gly Arg Asp Phe Ile Ser Ser Asp Gly Ser Arg Leu
    1250                1255                1260
Trp Ser Asp Ile Tyr Thr Leu Thr Tyr Gln Arg Ala Asp Gly Gln
    1265                1270                1275
Ala Asp Arg Ala Ser Val Gly Gly Pro Ser Ser Ala Ser Lys
    1280                1285                1290
Ser Ile Lys Gly Gly Ser Ser Asn Ser Asn Ser Asp Thr Gln Val
    1295                1300                1305
His Arg Met Ser Leu Leu Asp Ser Ile Leu Gln Ala Asp Leu Pro
    1310                1315                1320
Cys Asp Leu Glu Lys Ser Asn Pro Thr Tyr Asn Ile Leu Ala Leu
    1325                1330                1335
Leu Arg Ile Leu Glu Gly Leu Asn Gln Leu Ala Pro Arg Leu Arg
    1340                1345                1350
Val Gln Leu Val Ser Asp Asn Phe Ser Glu Gly Lys Ile Ser Ser
    1355                1360                1365
Leu Asp Glu Leu Met Thr Ala Thr Gly Val Arg Val Pro Ala Glu
    1370                1375                1380
Glu Phe Ile Asn Ser Lys Leu Thr Pro Lys Leu Ala Arg Gln Ile
    1385                1390                1395
Gln Asp Ala Leu Ala Leu Cys Ser Gly Ser Leu Pro Ser Trp Cys
    1400                1405                1410
Tyr Gln Leu Thr Lys Ala Cys Pro Phe Leu Phe Pro Phe Glu Thr
    1415                1420                1425
Arg Arg Gln Tyr Phe Tyr Ser Thr Ala Phe Gly Leu Ser Arg Ala
    1430                1435                1440
Leu Tyr Arg Leu Gln Gln Gln Gln Gly Ala Asp Gly His Gly Ser
    1445                1450                1455
Ala Asn Glu Arg Glu Val Arg Val Gly Arg Leu Gln Arg Gln Lys
    1460                1465                1470
Val Arg Val Ser Arg Asn Arg Ile Leu Asp Ser Ala Ala Lys Val
    1475                1480                1485
Met Glu Met Tyr Ser Ser Gln Lys Ala Val Leu Glu Val Glu Tyr
    1490                1495                1500
Phe Gly Glu Val Gly Thr Gly Leu Gly Pro Thr Leu Glu Phe Tyr
    1505                1510                1515
Thr Leu Leu Ser His Asp Leu Gln Lys Val Thr Leu Gly Met Trp
    1520                1525                1530
Arg Ser Asn Ser Ala Ala Glu Lys Pro Ser Met Glu Ile Asp Gly
    1535                1540                1545
Asp Asp Asp Lys Asn Gly Lys Ser Asn Asn Glu Ser Gly Thr Ala
    1550                1555                1560
Val Ala Ala Asp Leu Val Gln Thr Pro Leu Gly Leu Phe Pro Arg
    1565                1570                1575
Pro Trp Pro Pro Thr Ala Ser Ala Ser Glu Gly Ser Gln Ile Tyr
    1580                1585                1590
```

Lys Thr Ile Glu Tyr Phe Arg Leu Val Gly Arg Val Met Ala Lys
    1595                1600                1605

Ala Leu Gln Asp Gly Arg Leu Leu Asp Leu Pro Leu Ser Met Ala
    1610                1615                1620

Phe Tyr Lys Leu Val Leu Gly Gln Glu Leu Asp Leu Tyr Asp Ile
    1625                1630                1635

Leu Ser Phe Asp Ala Glu Phe Gly Lys Thr Leu Gln Glu Leu His
    1640                1645                1650

Ala Leu Val Cys Arg Lys His Tyr Leu Glu Ser Ile Gly Ser Asp
    1655                1660                1665

His Glu Ala Ile Ala Asp Leu His Phe His Gly Thr Pro Ile Glu
    1670                1675                1680

Asp Leu Cys Leu Asp Phe Thr Leu Pro Gly Tyr Pro Asp Tyr Ile
    1685                1690                1695

Leu Lys Pro Gly Asp Glu Thr Val Asp Ile Asn Asn Leu Glu Glu
    1700                1705                1710

Phe Ile Ser Leu Val Val Asp Ala Thr Val Lys Thr Gly Ile Thr
    1715                1720                1725

Arg Gln Met Glu Ala Phe Arg Glu Gly Phe Asn Gln Val Phe Asp
    1730                1735                1740

Ile Ser Ser Leu Gln Ile Phe Thr Pro Gln Glu Leu Asp Tyr Leu
    1745                1750                1755

Leu Cys Gly Arg Arg Glu Leu Trp Glu Pro Asp Thr Leu Val Asp
    1760                1765                1770

His Ile Lys Phe Asp His Gly Tyr Thr Ala Lys Ser Pro Ala Ile
    1775                1780                1785

Val Asn Leu Leu Glu Ile Met Gly Glu Phe Thr Pro Asp Gln Gln
    1790                1795                1800

Arg Ala Phe Cys Gln Phe Val Thr Gly Ala Pro Arg Leu Pro Pro
    1805                1810                1815

Gly Gly Leu Ala Val Leu Asn Pro Lys Leu Thr Ile Val Arg Lys
    1820                1825                1830

His Ser Ser Ser Ala Gly Asn Ala Met Pro Asn Gly Thr Gly Pro
    1835                1840                1845

Ser Glu Ser Ala Asp Asp Asp Leu Pro Ser Val Met Thr Cys Ala
    1850                1855                1860

Asn Tyr Leu Lys Leu Pro Pro Tyr Ser Thr Lys Glu Val Met Tyr
    1865                1870                1875

Lys Lys Leu Leu Tyr Ala Ile Ser Glu Gly Gln Gly Ser Phe Asp
    1880                1885                1890

Leu Ser
    1895

<210> SEQ ID NO 30
<211> LENGTH: 1887
<212> TYPE: PRT
<213> ORGANISM: Sorghum bicolor

<400> SEQUENCE: 30

Met Glu Thr Arg Ser Arg Lys Arg Ala Glu Ala Ser Ser Ser Ser Ala
1               5                   10                  15

Thr Ser Ser Ser Ser Arg Ser Ser Lys Arg Ser Arg Pro Asn Pro Asn
            20                  25                  30

Pro Asn Pro Asn Pro Asn Pro Pro Ala Ala Ser Ser Ser Pro Ala Pro

```
                    35                  40                  45
Asn Pro Val Pro Leu Pro Pro Arg Thr Arg Ser Ala Ala Val Asn
                50                  55                  60
Pro Leu Pro Ala Met Asp Ser Ser Gly Asp Asn Ser Asn Pro Asn
65                  70                  75                  80
Pro Pro Pro Arg Arg Gly Arg Pro Ser Asn Ala Asp Lys Gly Lys
                85                  90                  95
Glu Gln Gln Gln Pro Glu Pro Ser His Ser Ser Arg Val Arg Glu Ala
                100                 105                 110
Glu Arg Leu Leu Gly Leu Gly Phe Glu Gly Ile Glu Asp Asp Asp
                115                 120                 125
Ala Gly Phe Gly Ala Gly Ala Ile Pro His Ser Leu Thr Ser Ala Ser
                130                 135                 140
Thr Ala Leu Gln Gly Leu Leu Arg Lys Leu Gly Ala Gly Leu Asp Asp
145                 150                 155                 160
Ile Leu Pro Ser Ser Ala Leu Ser Ala Ala Ala Ala Ala Ala Ala
                165                 170                 175
Ser Ser Ser Ser Ala Ser Gly Gln Leu Gly Gly Arg Leu Lys Lys Ile
                180                 185                 190
Leu Ala Gly Leu Arg Ala Asp Gly Glu Asp Gly Arg Gln Ile Glu Ala
                195                 200                 205
Leu Thr Gln Leu Cys Glu Met Leu Ser Ile Gly Thr Glu Glu Ser Leu
                210                 215                 220
Gly Ala Phe Ser Val Asp Ser Phe Val Pro Val Leu Gly Leu Leu
225                 230                 235                 240
Asn His Glu Ser Asn Pro Asp Ile Met Leu Leu Ala Ala Arg Ala Leu
                245                 250                 255
Thr His Leu Cys Asp Val Leu Pro Ser Ser Cys Ser Ala Val Val His
                260                 265                 270
Tyr Gly Ala Val Pro Cys Phe Cys Ala Arg Leu Leu Thr Ile Glu Tyr
                275                 280                 285
Met Asp Leu Ala Glu Gln Ser Leu Gln Ala Leu Lys Lys Ile Ser Leu
                290                 295                 300
Glu His Pro Thr Ala Cys Leu Arg Ala Gly Ala Leu Met Ala Val Leu
305                 310                 315                 320
Ser Tyr Leu Asp Phe Phe Ser Thr Gly Val Gln Arg Val Ala Leu Ser
                325                 330                 335
Thr Ala Ala Asn Met Cys Arg Lys Leu Pro Ser Asp Ala Ser Asp Phe
                340                 345                 350
Val Met Glu Ala Val Pro Leu Leu Thr Asn Leu Leu Asn Tyr His Asp
                355                 360                 365
Ser Lys Val Leu Glu His Ala Ser Val Cys Leu Thr Arg Ile Ala Glu
                370                 375                 380
Ala Phe Ser Pro Phe Pro Glu Lys Leu Asp Glu Leu Cys Asn His Gly
385                 390                 395                 400
Leu Val Ala Gln Ala Ala Ser Leu Val Ser Val Ser Asn Leu Ala Gly
                405                 410                 415
Gln Ala Ser Leu Ser Thr Ser Thr Tyr Thr Gly Val Ile Arg Leu Leu
                420                 425                 430
Ser Ile Cys Ala Ser Gly Ser Pro Leu Ala Ala Lys Thr Leu Leu Leu
                435                 440                 445
Leu Gly Ile Ser Gly Thr Leu Lys Asp Ile Leu Ser Gly Ser Gly Leu
                450                 455                 460
```

```
Val Ala Gly Thr Thr Val Ser Pro Ala Leu Thr Arg Pro Ala Asp Gln
465                 470                 475                 480

Met Asn Glu Ile Val Lys Leu Ala Asp Glu Leu Leu Pro Pro Leu Pro
                485                 490                 495

Val Gly Thr Ile Ser Leu Pro Met Tyr Ser Asp Ile His Met Lys Gly
                500                 505                 510

Ser Ser Val Lys Lys Ser Thr Ser Asn Lys Gln Gly Glu His Gly Ser
            515                 520                 525

Thr Gly Ile Glu Leu Ser Gly Arg Glu Lys Leu Leu Arg Asp Gln Pro
        530                 535                 540

Glu Leu Leu Gln Gln Phe Gly Met Asp Leu Leu Pro Thr Met Thr Gln
545                 550                 555                 560

Val Tyr Gly Ser Ser Val Ser Gly Pro Ile Arg His Lys Cys Leu Ser
                565                 570                 575

Val Ile Gly Lys Leu Met Tyr Phe Ser Ser Ala Glu Met Ile Gln Ser
                580                 585                 590

Leu Leu Ser Thr Thr Asn Ile Ser Ser Phe Leu Ala Gly Ile Leu Ala
            595                 600                 605

Trp Lys Asp Pro Gln Val Leu Ile Pro Ala Leu Gln Ile Ala Glu Val
        610                 615                 620

Leu Met Glu Lys Leu Pro Glu Ile Phe Val Lys Met Phe Val Arg Glu
625                 630                 635                 640

Gly Val Val His Ala Val Glu Ser Leu Ile Cys Pro Glu Phe Ser Gly
                645                 650                 655

Gln Val Thr Pro Gln Val Ser Gln Leu Asp Asn His Val Asp Ser Ile
                660                 665                 670

Thr Ser Ser Gln Asn Arg Arg Asn Arg Arg Asn Asn Ala Val Ser
            675                 680                 685

Thr Glu Asn Asn Leu Pro Asp Gly Ser Lys Gly Ser His Ser Val Ile
        690                 695                 700

Ala Asn Ser Pro Pro Ser Thr Ala Glu Val Pro Asn Asn Ser Leu Arg
705                 710                 715                 720

Ala Leu Val Ser Asn His Ala Lys Ser Phe Lys Asp Lys Tyr Phe Pro
                725                 730                 735

Ser Glu Pro Gly Ser Ser Asp Ile Ala Val Thr Asp Asp Leu Leu Lys
            740                 745                 750

Leu Arg Ala Leu Cys Ala Lys Leu Asn Thr Thr Ala Asp Thr Ile Lys
        755                 760                 765

Thr Lys Ala Lys Gly Lys Ser Lys Ala Val Val Gly Asn Asn Phe Asp
        770                 775                 780

Val Leu Cys Asn Val Glu Glu Gln Leu Asp Gly Ile Ile Ala Glu Met
785                 790                 795                 800

Leu Ser Glu Leu Ser Lys Gly Asp Gly Val Ser Thr Phe Glu Phe Ile
                805                 810                 815

Gly Ser Gly Val Val Ser Ala Leu Leu Thr Tyr Leu Ser Cys Gly Thr
                820                 825                 830

Phe Gly Arg Glu Lys Val Ser Glu Ala Asn Ile Pro Asn Leu Arg His
            835                 840                 845

Gln Ala Val Arg Arg Tyr Lys Ala Phe Ile Ser Leu Ala Leu Pro Asn
        850                 855                 860

Asp Lys Asn Gly Asn Lys Thr Pro Met Thr Phe Leu Val His Lys Leu
865                 870                 875                 880
```

```
Gln Ser Ala Leu Ser Ser Leu Glu Arg Phe Pro Val Val Leu Ser His
                885                 890                 895
Ser Gly Arg Ala Pro Thr Leu Gly Gly Ser Arg Leu Thr Thr Gly Leu
            900                 905                 910
Gly Ala Leu Ser Gln Pro Phe Lys Leu Arg Leu Cys Arg Ala Pro Gly
        915                 920                 925
Glu Lys Ser Leu Lys Asp Tyr Ser Ser Asn Ile Val Leu Ile Asp Pro
    930                 935                 940
Leu Ala Ser Leu Ala Ala Val Glu Asp Phe Leu Trp Pro Arg Val Gln
945                 950                 955                 960
Arg Thr Glu Pro Val Ser Lys Pro Pro Val Ser Ala Asn Asn Ser Glu
                965                 970                 975
Ser Gly Ala Ala Ser Ser Thr Ala Cys Ala Pro Ser Ile Pro Pro Gly
            980                 985                 990
Thr Gln Ser Gly Arg Arg Ala Ser Leu Arg Ser Gln Ser Ser Ala Ala
        995                 1000                1005
Thr Ser Gly Ala Ile Lys Lys Asp Tyr Gln Glu Gly Ser Ile Asn
    1010                1015                1020
Thr Ser Lys Gly Lys Gly Lys Ala Val Leu Lys Ser Ser Leu Asp
    1025                1030                1035
Glu Pro Lys Gly Pro His Thr Arg Asn Ala Glu Arg Arg Lys Ala
    1040                1045                1050
Ala Ser Glu Lys Asp Val Glu Leu Lys Pro Ser His Asp His Ser
    1055                1060                1065
Thr Ser Glu Asp Glu Asp Leu Asp Ala Ser Pro Val Glu Ile Asp
    1070                1075                1080
Asp Ala Leu Met Leu Asp Asp Asp Glu Asp Val Ser Glu Asp
    1085                1090                1095
Glu Asp Asp Asp His Glu Ala Val Leu Arg Gly Ser Leu Pro Ser
    1100                1105                1110
Cys Val Pro Glu Gly Val His Asp Val Lys Leu Gly Asp Ala Asp
    1115                1120                1125
Asp Ser Ser Val Ala Ser Leu Ala Asn Asp Asn Gln Ala Gln Pro
    1130                1135                1140
Ser Ser Gly Ser Ser Thr Lys Asn Ala Ser Gly Arg Gly Leu Asp
    1145                1150                1155
Ala Ala Glu Phe Arg Ser Pro Ser Thr Phe Gly Ser Arg Gly Ala
    1160                1165                1170
Met Ser Phe Ala Ala Ala Met Ala Gly Leu Thr Ser Val Gly
    1175                1180                1185
Ser Arg Gly Ile Arg Gly Ser Arg Asp Arg Ser Gly Leu Pro Leu
    1190                1195                1200
Gly Ala Arg Thr Thr Glu His Tyr Asn Lys Leu Ile Phe Thr Ala
    1205                1210                1215
Gly Gly Lys Gln Leu Asn Lys His Leu Thr Val Tyr Gln Ala Val
    1220                1225                1230
Gln Arg Gln Val Val His Asp Glu Asp Glu Asp Gln Leu Gly
    1235                1240                1245
Gly Ser Asp Leu Pro Asp Asp Gly Asn His Phe Trp Gly Asp Val
    1250                1255                1260
Phe Thr Ile Thr Tyr Gln Lys Ala Asp Asn Thr Ala Glu Lys Gly
    1265                1270                1275
Ser Val Gly Gly Ser Ala Ser Val Pro Lys Pro Ser Lys Ser Asp
```

```
              1280                1285                1290

Ser Cys Arg Thr Ser Ser Gln Lys Ser Phe Thr Ser Leu Leu Asp
    1295                1300                1305

Ser Ile Leu Gln Gly Glu Leu Pro Cys Asp Leu Glu Lys Ser Asn
    1310                1315                1320

Gln Thr Tyr Asn Ile Leu Ser Leu Leu Arg Val Leu Glu Gly Leu
    1325                1330                1335

Asn Gln Leu Ser Pro Arg Leu Lys Leu Gln Ala Thr Arg Asp Asp
    1340                1345                1350

Phe Ala Glu Gly Lys Val Ala Thr Leu Asp Gly Leu Tyr Asp Val
    1355                1360                1365

Gly Val Lys Val Pro Ser Glu Glu Phe Val Asn Ser Lys Met Thr
    1370                1375                1380

Pro Lys Leu Ala Arg Gln Ile Gln Asp Val Leu Ala Leu Cys Ser
    1385                1390                1395

Gly Ser Leu Pro Ser Trp Cys Tyr Gln Leu Thr Lys Ala Cys Pro
    1400                1405                1410

Phe Leu Phe Pro Phe Glu Thr Arg Arg Gln Tyr Phe Tyr Ser Thr
    1415                1420                1425

Ala Phe Gly Leu Ser Arg Ala Leu His Arg Leu Gln Gln Gln Pro
    1430                1435                1440

Gly Asp Asn Asn Asn Thr Ala Phe Glu Arg Glu Val Arg Val Gly
    1445                1450                1455

Arg Leu Gln Arg Gln Lys Val Arg Val Ser Arg Asn Arg Ile Leu
    1460                1465                1470

Asp Ser Ala Ala Lys Val Met Glu Met Phe Ser Asn Gln Lys Ala
    1475                1480                1485

Val Leu Glu Val Glu Tyr Phe Gly Glu Val Gly Thr Gly Leu Gly
    1490                1495                1500

Pro Thr Leu Glu Phe Tyr Thr Leu Leu Ser Arg Glu Leu Gln Arg
    1505                1510                1515

Val Asp Leu Gly Leu Trp Arg Ser His Ser Pro Asp Asp Ser Gly
    1520                1525                1530

Met Gln Leu Asp Gly Asn Ala Asp Asp Leu Thr Ser Glu Lys Arg
    1535                1540                1545

Glu Ser Glu Ser Leu Val Glu Ser Arg Asn Ile Val Gln Ala Pro
    1550                1555                1560

Leu Gly Leu Phe Pro Gln Pro Trp Pro Pro Ser Ala Ala Ala Ser
    1565                1570                1575

Glu Gly Ser Lys Phe Phe Lys Val Val Glu Tyr Phe Arg Leu Val
    1580                1585                1590

Gly Arg Thr Met Ala Lys Ala Leu Gln Asp Gly Arg Leu Leu Asp
    1595                1600                1605

Leu Pro Leu Ser Thr Ala Phe Tyr Lys Leu Leu Leu Gly Gln Glu
    1610                1615                1620

Leu Asp Leu Tyr Asp Ile Leu Ser Phe Asp Thr Glu Phe Gly Lys
    1625                1630                1635

Thr Leu Gln Glu Leu Gln Ile Leu Val Ala Arg Lys Gln Phe Leu
    1640                1645                1650

Glu Ser Cys Ser Ser Glu Asn Gln Lys Ile Glu Glu Leu Cys Phe
    1655                1660                1665

Arg Gly Ala Pro Ile Glu Asp Leu Cys Leu Asp Phe Thr Leu Pro
    1670                1675                1680
```

-continued

```
Gly Tyr Pro Asp Tyr Val Leu Lys Glu Gly Gly Glu Asn Ala Val
    1685                1690                1695

Val Asn Ile Tyr Asn Leu Glu Glu Tyr Ile Ser Leu Val Val Asp
    1700                1705                1710

Ala Thr Val Lys Thr Gly Ile Met Arg Gln Val Glu Ala Leu Lys
    1715                1720                1725

Ala Gly Phe Asn Gln Val Phe Asp Ile Ser Thr Leu Gln Ile Phe
    1730                1735                1740

Ser Pro Gln Glu Leu Asp Tyr Leu Phe Cys Gly Arg Arg Glu Leu
    1745                1750                1755

Trp Glu Pro Glu Thr Leu Pro Glu His Ile Lys Phe Asp His Gly
    1760                1765                1770

Tyr Thr Ser Lys Ser Pro Ala Ile Val Asn Phe Leu Glu Ile Met
    1775                1780                1785

Ala Glu Phe Thr Pro Glu Gln Gln His Ala Phe Cys Gln Phe Val
    1790                1795                1800

Thr Gly Ala Pro Arg Leu Pro Pro Gly Gly Leu Ala Ala Leu Asn
    1805                1810                1815

Pro Lys Leu Thr Ile Val Arg Lys His Ser Ser Ala Ala Asn Asn
    1820                1825                1830

Thr Ser Asn Pro Thr Gly Ala Thr Glu Ser Ala Asp Asp Asp Leu
    1835                1840                1845

Pro Ser Val Met Thr Cys Ala Asn Tyr Leu Lys Leu Pro Pro Tyr
    1850                1855                1860

Ser Thr Lys Ala Ile Met Leu Lys Lys Leu Leu Tyr Ala Ile Asn
    1865                1870                1875

Glu Gly Gln Gly Ser Phe Asp Leu Ser
    1880                1885

<210> SEQ ID NO 31
<211> LENGTH: 20
<212> TYPE: DNA
<213> ORGANISM: Arabidopsis thaliana

<400> SEQUENCE: 31
caatggactc aggcattatt                                              20

<210> SEQ ID NO 32
<211> LENGTH: 18
<212> TYPE: DNA
<213> ORGANISM: Arabidopsis thaliana

<400> SEQUENCE: 32
gagtttcctt tctccacc                                                18

<210> SEQ ID NO 33
<211> LENGTH: 21
<212> TYPE: DNA
<213> ORGANISM: Arabidopsis thaliana

<400> SEQUENCE: 33
gctttcttcc cttcctttct c                                            21

<210> SEQ ID NO 34
<211> LENGTH: 21
<212> TYPE: DNA
<213> ORGANISM: Arabidopsis thaliana
```

```
<400> SEQUENCE: 34
caataccgtg cattgtgtca g                                              21

<210> SEQ ID NO 35
<211> LENGTH: 21
<212> TYPE: DNA
<213> ORGANISM: Arabidopsis thaliana

<400> SEQUENCE: 35
gagggtaaaa cctggcaaaa g                                              21

<210> SEQ ID NO 36
<211> LENGTH: 21
<212> TYPE: DNA
<213> ORGANISM: Arabidopsis thaliana

<400> SEQUENCE: 36
ttcattgtca gtggaagagg g                                              21

<210> SEQ ID NO 37
<211> LENGTH: 21
<212> TYPE: DNA
<213> ORGANISM: Arabidopsis thaliana

<400> SEQUENCE: 37
cagaccaaca aactcccagt c                                              21

<210> SEQ ID NO 38
<211> LENGTH: 23
<212> TYPE: DNA
<213> ORGANISM: Arabidopsis thaliana

<400> SEQUENCE: 38
atattgacca tcatactcat tgc                                            23

<210> SEQ ID NO 39
<211> LENGTH: 21
<212> TYPE: DNA
<213> ORGANISM: Arabidopsis thaliana

<400> SEQUENCE: 39
gctggagtat tacgggagga c                                              21

<210> SEQ ID NO 40
<211> LENGTH: 21
<212> TYPE: DNA
<213> ORGANISM: Arabidopsis thaliana

<400> SEQUENCE: 40
ttcactgcct gaccacctaa g                                              21

<210> SEQ ID NO 41
<211> LENGTH: 20
<212> TYPE: DNA
<213> ORGANISM: Arabidopsis thaliana

<400> SEQUENCE: 41
tcaatggccg gaaagggaaa                                                20

<210> SEQ ID NO 42
<211> LENGTH: 20
<212> TYPE: DNA
<213> ORGANISM: Arabidopsis thaliana
```

```
<400> SEQUENCE: 42
gggcttcatc aagttcacgc                                               20

<210> SEQ ID NO 43
<211> LENGTH: 20
<212> TYPE: DNA
<213> ORGANISM: Arabidopsis thaliana

<400> SEQUENCE: 43
catcaaacag gattttcgcc                                               20

<210> SEQ ID NO 44
<211> LENGTH: 21
<212> TYPE: DNA
<213> ORGANISM: Arabidopsis thaliana

<400> SEQUENCE: 44
caatctcctg aagctagccg t                                             21

<210> SEQ ID NO 45
<211> LENGTH: 22
<212> TYPE: DNA
<213> ORGANISM: Arabidopsis thaliana

<400> SEQUENCE: 45
cgagagtacg ttcttcgtgt tc                                            22

<210> SEQ ID NO 46
<211> LENGTH: 16
<212> TYPE: DNA
<213> ORGANISM: Arabidopsis thaliana

<400> SEQUENCE: 46
tccgtggtag cagcag                                                   16

<210> SEQ ID NO 47
<211> LENGTH: 21
<212> TYPE: DNA
<213> ORGANISM: Arabidopsis thaliana

<400> SEQUENCE: 47
taacaataga ggcaaaagca t                                             21

<210> SEQ ID NO 48
<211> LENGTH: 20
<212> TYPE: DNA
<213> ORGANISM: Arabidopsis thaliana

<400> SEQUENCE: 48
gggcttcatc aagttcacgc                                               20

<210> SEQ ID NO 49
<211> LENGTH: 20
<212> TYPE: DNA
<213> ORGANISM: Arabidopsis thaliana

<400> SEQUENCE: 49
tcaatggccg gaaagggaaa                                               20

<210> SEQ ID NO 50
<211> LENGTH: 20
<212> TYPE: DNA
```

<213> ORGANISM: Arabidopsis thaliana

<400> SEQUENCE: 50
tggtgtccag ggtttagctg					20

<210> SEQ ID NO 51
<211> LENGTH: 23
<212> TYPE: DNA
<213> ORGANISM: Arabidopsis thaliana

<400> SEQUENCE: 51
tgatagctag aaagagtcgg agt				23

<210> SEQ ID NO 52
<211> LENGTH: 20
<212> TYPE: DNA
<213> ORGANISM: Arabidopsis thaliana

<400> SEQUENCE: 52
agagactttc cggcaaccag					20

<210> SEQ ID NO 53
<211> LENGTH: 20
<212> TYPE: DNA
<213> ORGANISM: Arabidopsis thaliana

<400> SEQUENCE: 53
gtgatacggc ggatcgagtt					20

<210> SEQ ID NO 54
<211> LENGTH: 20
<212> TYPE: DNA
<213> ORGANISM: Arabidopsis thaliana

<400> SEQUENCE: 54
agccggtgat gtcaagatcg					20

<210> SEQ ID NO 55
<211> LENGTH: 20
<212> TYPE: DNA
<213> ORGANISM: Arabidopsis thaliana

<400> SEQUENCE: 55
tcattcatct gctgagggcg					20

<210> SEQ ID NO 56
<211> LENGTH: 20
<212> TYPE: DNA
<213> ORGANISM: Arabidopsis thaliana

<400> SEQUENCE: 56
tcttcgcctt tgtttccggt					20

<210> SEQ ID NO 57
<211> LENGTH: 20
<212> TYPE: DNA
<213> ORGANISM: Arabidopsis thaliana

<400> SEQUENCE: 57
cgttaatggc atctgcgagg					20

<210> SEQ ID NO 58
<211> LENGTH: 20

```
<212> TYPE: DNA
<213> ORGANISM: Arabidopsis thaliana

<400> SEQUENCE: 58
ctggaccttc ccctagaccc                                            20

<210> SEQ ID NO 59
<211> LENGTH: 20
<212> TYPE: DNA
<213> ORGANISM: Arabidopsis thaliana

<400> SEQUENCE: 59
caacttcggg ctcaaaggac                                            20

<210> SEQ ID NO 60
<211> LENGTH: 20
<212> TYPE: DNA
<213> ORGANISM: Arabidopsis thaliana

<400> SEQUENCE: 60
cccatggacc ttgtgagcta                                            20

<210> SEQ ID NO 61
<211> LENGTH: 20
<212> TYPE: DNA
<213> ORGANISM: Arabidopsis thaliana

<400> SEQUENCE: 61
gtccaatgtt gcaggggaga                                            20

<210> SEQ ID NO 62
<211> LENGTH: 18
<212> TYPE: DNA
<213> ORGANISM: Arabidopsis thaliana

<400> SEQUENCE: 62
gagtttcctt tctccacc                                              18

<210> SEQ ID NO 63
<211> LENGTH: 20
<212> TYPE: DNA
<213> ORGANISM: Arabidopsis thaliana

<400> SEQUENCE: 63
caatggactc aggcattatt                                            20

<210> SEQ ID NO 64
<211> LENGTH: 21
<212> TYPE: DNA
<213> ORGANISM: Arabidopsis thaliana

<400> SEQUENCE: 64
gctttcttcc cttcctttct c                                          21

<210> SEQ ID NO 65
<211> LENGTH: 860
<212> TYPE: PRT
<213> ORGANISM: Arabidopsis thaliana

<400> SEQUENCE: 65

Met Val Ser Arg Ser Tyr Ser Asn Leu Leu Glu Leu Ala Ser Gly Asp
1               5                   10                  15

Ser Pro Thr Phe Gly Arg Met Asn Arg Gln Ile Pro Arg Ile Met Ala
```

```
                    20                  25                  30
Val Ala Gly Ile Met Ser Asn Ile Asp Asn Asp Ser Lys Asp Thr Asp
            35                  40                  45

Leu Ser Pro Lys Asp Arg Ile Ile Val Ala Asn Glu Leu Pro Ile
50                  55                  60

Arg Ala Gln Arg Arg Val Asp Gly Asn Gly Ser Gly Ser Ser Ser Ser
65                  70                  75                  80

Ser Thr Cys Cys Ser Lys Gly Trp Asn Phe Ser Trp Asp Glu Asn Ser
                85                  90                  95

Leu Leu Leu Gln Leu Lys Asp Gly Leu Gly Asp Glu Ala Ile Glu Val
                100                 105                 110

Ile Tyr Val Gly Cys Leu Lys Glu Glu Ile Pro Leu Asn Glu Gln Glu
            115                 120                 125

Glu Val Tyr Gln Ile Leu Leu Glu Ser Phe Lys Cys Val Pro Thr Phe
            130                 135                 140

Leu Pro Leu Asp Leu Tyr Thr Arg Tyr Tyr His Gly Phe Cys Lys Gln
145                 150                 155                 160

Gln Leu Trp Pro Leu Phe His Tyr Met Leu Pro Leu Ser Pro Asp Leu
                165                 170                 175

Gly Gly Arg Phe Asp Arg Thr Leu Trp Gln Ala Tyr Val Ser Val Asn
                180                 185                 190

Lys Ile Phe Ala Asp Arg Ile Met Glu Val Ile Asn Pro Glu Asp Asp
            195                 200                 205

Phe Val Trp Ile His Asp Tyr His Leu Met Val Leu Pro Thr Phe Leu
            210                 215                 220

Arg Lys Arg Phe Asn Arg Val Lys Leu Gly Phe Phe Leu His Ser Pro
225                 230                 235                 240

Phe Pro Ser Ser Glu Ile Tyr Lys Thr Leu Pro Ile Arg Glu Glu Leu
                245                 250                 255

Leu Arg Ala Leu Leu Asn Ser Asp Leu Ile Gly Phe His Thr Phe Asp
                260                 265                 270

Tyr Ala Arg His Phe Leu Ser Cys Cys Ser Arg Met Leu Gly Leu Thr
            275                 280                 285

Tyr Glu Ser Lys Arg Gly Tyr Ile Gly Leu Glu Tyr Tyr Gly Arg Thr
            290                 295                 300

Val Ser Ile Lys Ile Leu Pro Val Gly Ile His Met Gly Gln Leu Gln
305                 310                 315                 320

Ser Val Leu Ser Leu Pro Glu Thr Glu Arg Lys Val Gly Glu Leu Ile
                325                 330                 335

Glu Arg Tyr Gly Arg Lys Gly Arg Thr Met Leu Leu Gly Val Asp Asp
                340                 345                 350

Met Asp Ile Phe Lys Gly Ile Thr Leu Lys Leu Leu Ala Met Glu Gln
            355                 360                 365

Leu Leu Met Gln His Pro Glu Trp Gln Gly Lys Val Val Leu Val Gln
            370                 375                 380

Ile Ala Asn Pro Ala Arg Gly Lys Gly Lys Asp Val Lys Glu Met Gln
385                 390                 395                 400

Ala Glu Thr Tyr Ser Thr Val Lys Arg Ile Asn Glu Thr Phe Gly Arg
                405                 410                 415

Pro Gly Tyr Asp Pro Ile Val Leu Ile Asp Ala Pro Leu Lys Phe Tyr
                420                 425                 430

Glu Arg Val Ala Tyr Tyr Val Val Ala Glu Cys Cys Leu Val Thr Ala
            435                 440                 445
```

```
Val Arg Asp Gly Met Asn Leu Ile Pro Tyr Glu Tyr Ile Val Ser Arg
    450                 455                 460
Gln Gly Asn Glu Lys Leu Asp Lys Ile Leu Lys Leu Glu Ala Asn Asn
465                 470                 475                 480
Arg Asn Lys Lys Ser Met Leu Val Val Ser Glu Phe Ile Gly Cys Ser
                485                 490                 495
Pro Ser Leu Ser Gly Ala Ile Arg Val Asn Pro Trp Asn Val Asp Ala
            500                 505                 510
Val Ala Asp Ala Met Asp Ser Ala Leu Glu Val Ala Glu Pro Glu Lys
        515                 520                 525
Gln Leu Arg His Glu Lys His Tyr Lys Tyr Val Ser Thr His Asp Val
    530                 535                 540
Gly Tyr Trp Ala Arg Ser Phe Leu Gln Asp Leu Glu Arg Ser Cys Gly
545                 550                 555                 560
Glu His Gly Arg Arg Cys Trp Gly Ile Gly Phe Gly Leu Ser Phe
                565                 570                 575
Arg Val Val Ala Leu Asp Gln Ser Phe Arg Lys Leu Ser Met Glu His
                580                 585                 590
Ile Val Ser Ala Tyr Lys Arg Thr Lys Thr Arg Ala Ile Leu Leu Asp
    595                 600                 605
Tyr Asp Asp Thr Leu Met Pro Gln Gly Ser Ile Asp Lys Arg Pro Ser
610                 615                 620
Ser Lys Ser Ile Asp Ile Leu Asn Thr Leu Cys Arg Asp Lys Gly Asn
625                 630                 635                 640
Leu Val Phe Ile Val Ser Ala Lys Ser Arg Glu Thr Leu Ser Asp Trp
                645                 650                 655
Phe Ser Pro Cys Glu Lys Leu Gly Ile Ala Ala Glu His Gly Tyr Phe
                660                 665                 670
Leu Arg Leu Arg Lys Ala Val Glu Trp Glu Asn Cys Val Ala Ala Val
        675                 680                 685
Asp Cys Ser Trp Lys Gln Ile Ala Glu Pro Val Met Glu Leu Tyr Thr
    690                 695                 700
Glu Thr Thr Asp Gly Ser Thr Ile Glu Asp Lys Glu Thr Ala Leu Val
705                 710                 715                 720
Trp Ser Tyr Glu Asp Ala Asp Pro Asp Phe Gly Ser Cys Gln Ala Lys
                725                 730                 735
Glu Leu Leu Asp His Leu Glu Ser Val Leu Ala Asn Glu Pro Val Thr
                740                 745                 750
Val Lys Arg Gly Gln Asn Tyr Val Glu Val Lys Pro Gln Gly Val Ser
        755                 760                 765
Lys Gly Leu Ile Ala Arg Arg Met Leu Ser Met Met Gln Glu Arg Gly
    770                 775                 780
Thr Leu Pro Glu Phe Val Leu Cys Ile Gly Asp Asp Arg Ser Asp Glu
785                 790                 795                 800
Asp Met Phe Glu Val Ile Cys Ser Ser Thr Glu Gly Pro Ser Ile Ala
                805                 810                 815
Pro Arg Ala Glu Ile Phe Ala Cys Thr Val Gly Gln Lys Pro Ser Lys
                820                 825                 830
Ala Lys Tyr Tyr Leu Asp Asp Thr Thr Glu Ile Val Arg Leu Met His
        835                 840                 845
Gly Leu Ala Ser Val Thr Asp Gln Ile Thr Pro Val
850                 855                 860
```

<210> SEQ ID NO 66
<211> LENGTH: 796
<212> TYPE: PRT
<213> ORGANISM: Zea mays

<400> SEQUENCE: 66

```
Met Ala Ser Arg Ser Tyr Ser Asn Leu Leu Asp Leu Ala Thr Gly Ala
1               5                   10                  15

Ala Asp Gln Ala Pro Ala Val Ala Ala Leu Gly Ala Leu Arg Arg Arg
            20                  25                  30

Leu Pro Arg Val Val Thr Thr Pro Gly Leu Ile Asp Asp Ser Pro Ala
        35                  40                  45

Ser Pro Ser Thr Pro Pro Arg Pro Arg Thr Ile Ile Val Ala Asn Gln
    50                  55                  60

Leu Pro Ile Arg Ser His Arg Pro Glu Ser Pro Glu Glu Pro Trp Thr
65                  70                  75                  80

Phe Glu Trp Asp Glu Asp Ser Leu Leu Arg His Leu His His Ser Ser
                85                  90                  95

Ser Pro Leu Met Glu Phe Ile Tyr Ile Gly Cys Leu Arg Asp Asp Ile
            100                 105                 110

Pro Gln Ala Glu Gln Asp Ala Val Ala Gln Ala Leu Leu Glu Thr His
        115                 120                 125

Asn Cys Val Pro Ala Phe Leu Pro Thr Asp Ile Ala Glu Arg Tyr Tyr
    130                 135                 140

His Gly Phe Cys Lys Gln His Leu Trp Pro Leu Phe His Tyr Met Leu
145                 150                 155                 160

Pro Leu Ser Pro Asp Leu Gly Gly Arg Phe Asp Arg Ala Leu Trp Gln
                165                 170                 175

Ala Tyr Val Ser Ala Asn Lys Ile Phe Ala Asp Lys Val Leu Glu Val
            180                 185                 190

Ile Asn Pro Asp Asp Asp Phe Val Trp Val His Asp Tyr His Leu Met
        195                 200                 205

Val Leu Pro Thr Phe Leu Arg Lys Arg Phe Asn Arg Ile Lys Leu Gly
    210                 215                 220

Phe Phe Leu His Ser Pro Phe Pro Ser Ser Glu Ile Tyr Lys Thr Leu
225                 230                 235                 240

Pro Val Arg Glu Glu Leu Leu Arg Ala Leu Leu Asn Ser Asp Leu Ile
                245                 250                 255

Gly Phe His Thr Phe Asp Tyr Ala Arg His Phe Leu Ser Cys Cys Gly
            260                 265                 270

Arg Met Leu Gly Leu Ser Tyr Glu Ser Lys Arg Gly His Ile Cys Leu
        275                 280                 285

Glu Tyr Tyr Gly Arg Thr Val Ser Ile Lys Ile Leu Pro Val Gly Val
    290                 295                 300

His Met Glu Gln Leu Lys Thr Val Leu Gly Leu Pro Glu Thr Glu Ala
305                 310                 315                 320

Lys Val Ser Glu Leu Met Glu Met Tyr Ser Gly Lys Gly Arg Val Val
                325                 330                 335

Met Leu Gly Val Asp Asp Met Asp Ile Phe Lys Gly Ile Ser Leu Lys
            340                 345                 350

Leu Leu Ala Met Glu Glu Leu Leu Arg Gln His Pro Glu Trp Arg Gly
        355                 360                 365

Lys Leu Val Leu Val Gln Val Ala Asn Pro Ala Arg Gly Arg Gly Lys
    370                 375                 380
```

-continued

```
Asp Val Ala Glu Val Gln Thr Glu Thr Tyr Ala Met Val Arg Arg Ile
385                 390                 395                 400

Asn Glu Val Tyr Gly Glu Pro Gly Tyr Glu Pro Val Val Leu Ile Asp
            405                 410                 415

Glu Pro Leu Gln Phe Tyr Glu Arg Val Ala Tyr Tyr Val Ile Ala Glu
        420                 425                 430

Val Cys Leu Val Thr Ala Val Arg Asp Gly Met Asn Leu Ile Pro Tyr
    435                 440                 445

Glu Tyr Ile Val Ser Arg Gln Gly Asn Glu Lys Leu Asp Arg Met Leu
450                 455                 460

Arg Gln Gly Lys Pro Glu Lys Lys Ser Met Leu Val Val Ser Glu
465                 470                 475                 480

Phe Ile Gly Cys Ser Pro Ser Leu Ser Gly Ala Ile Arg Val Asn Pro
                485                 490                 495

Trp Asn Ile Glu Ala Val Ala Asp Ala Met Glu Thr Ala Leu Val Leu
            500                 505                 510

Pro Glu Asn Glu Lys Arg Leu Arg His Asp Lys His Phe Arg Tyr Val
        515                 520                 525

Ser Thr His Asp Val Gly Tyr Trp Ala Asn Ser Phe Leu Leu Asp Leu
    530                 535                 540

Glu Arg Thr Cys Lys Tyr His Ser Gln Lys Arg Cys Trp Gly Ile Gly
545                 550                 555                 560

Phe Gly Leu Arg Phe Arg Val Val Ser Leu Asp Leu Thr Phe Arg Lys
                565                 570                 575

Leu Ser Leu Glu Asn Ile Leu Met Ala Tyr Arg Arg Ala Lys Thr Arg
            580                 585                 590

Ala Ile Leu Leu Asp Tyr Asp Gly Thr Leu Met Pro Gln Ala Ile Asn
        595                 600                 605

Lys Ser Pro Ser Thr Glu Ser Val Arg Ile Leu Asn Ser Leu Cys Arg
610                 615                 620

Asp Lys Asp Asn Val Val Tyr Leu Cys Ser Gly Tyr Asp Arg Arg Thr
625                 630                 635                 640

Leu His Glu Trp Phe Pro Cys Glu Asn Leu Gly Ile Ala Ala Glu His
                645                 650                 655

Gly Tyr Phe Leu Arg Cys Lys Arg Asp Ala Glu Trp Lys Thr Cys Val
            660                 665                 670

Ala Ala Thr Asp Cys Ser Trp Lys Gln Ile Ala Glu Pro Gly Val Ser
        675                 680                 685

Lys Gly Leu Val Ala Arg Arg Met Leu Val Ser Met Lys Glu Arg Gly
690                 695                 700

Gln Cys Pro Asp Phe Val Leu Cys Ile Gly Asp Asp Lys Ser Asp Glu
705                 710                 715                 720

Asp Met Phe Gln Leu Ile Ala Thr Ala Ala Cys Gly Asp Ser Leu Ala
                725                 730                 735

Ser Lys Ala Glu Val Phe Ala Cys Thr Val Gly Arg Lys Pro Ser Lys
            740                 745                 750

Ala Lys Tyr Tyr Leu Asp Asp Ala Ala Glu Val Val Arg Leu Met Gln
        755                 760                 765

Gly Leu Ser Tyr Val Ser Glu Glu Leu Ala Leu Ala Asn Gln Arg Asp
770                 775                 780

Glu Asp Glu Asp Ser Ser Leu Asp Asp Val Trp Glu
785                 790                 795
```

-continued

```
<210> SEQ ID NO 67
<211> LENGTH: 756
<212> TYPE: PRT
<213> ORGANISM: Sorghum bicolor

<400> SEQUENCE: 67

Glu Phe Ile Tyr Ile Gly Cys Leu Arg Asp Asp Ile Pro Leu Ala Asp
1               5                   10                  15

Gln Asp Ala Val Ala Gln Ala Leu Leu Glu Ser Tyr Asn Cys Val Pro
            20                  25                  30

Ala Phe Leu Pro Pro Asp Ile Ala Glu Arg Tyr Tyr His Gly Phe Cys
        35                  40                  45

Lys Gln His Leu Trp Pro Leu Phe His Tyr Met Leu Pro Leu Ser Pro
    50                  55                  60

Asp Leu Gly Gly Arg Phe Asp Arg Ala Leu Trp Gln Ser Tyr Val Ser
65                  70                  75                  80

Ala Asn Lys Ile Phe Ala Asp Lys Val Leu Glu Val Ile Asn Pro Asp
                85                  90                  95

Asp Asp Phe Val Trp Val His Asp Tyr His Leu Met Val Leu Pro Thr
            100                 105                 110

Phe Leu Arg Lys Arg Phe Asn Arg Ile Lys Leu Gly Phe Phe Leu His
        115                 120                 125

Ser Pro Phe Pro Ser Ser Glu Ile Tyr Lys Thr Leu Pro Val Arg Glu
    130                 135                 140

Glu Leu Leu Arg Ala Leu Leu Asn Ser Asp Leu Ile Gly Phe His Thr
145                 150                 155                 160

Phe Asp Tyr Ala Arg His Phe Leu Ser Cys Cys Gly Arg Met Leu Gly
                165                 170                 175

Leu Ser Tyr Glu Ser Lys Arg Gly His Ile Cys Leu Glu Tyr Tyr Gly
            180                 185                 190

Arg Thr Val Ser Ile Lys Ile Leu Pro Val Gly Val Asn Met Gly Gln
        195                 200                 205

Leu Lys Thr Val Leu Ala Leu Pro Glu Thr Glu Ala Lys Val Ala Glu
    210                 215                 220

Leu Met Ala Thr Tyr Ser Gly Lys Gly Arg Val Val Met Leu Gly Val
225                 230                 235                 240

Asp Asp Met Asp Ile Phe Lys Gly Ile Ser Leu Lys Leu Leu Ala Met
                245                 250                 255

Glu Glu Leu Leu Arg Gln His Pro Glu Trp Arg Gly Lys Leu Val Leu
            260                 265                 270

Val Gln Val Ala Asn Pro Ala Arg Gly Arg Gly Lys Asp Val Asp Glu
        275                 280                 285

Val Lys Gly Glu Thr Tyr Ala Met Val Arg Arg Ile Asn Glu Ala Tyr
    290                 295                 300

Gly Ala Pro Gly Tyr Glu Pro Val Val Leu Ile Asp Glu Pro Leu Gln
305                 310                 315                 320

Phe Tyr Glu Arg Val Ala Tyr Tyr Val Ala Glu Val Cys Leu Val
                325                 330                 335

Thr Ala Val Arg Asp Gly Met Asn Leu Ile Pro Tyr Glu Tyr Ile Val
            340                 345                 350

Ser Arg Gln Gly Asn Glu Ala Leu Asp Arg Met Leu Gln Pro Ser Lys
        355                 360                 365

Pro Glu Glu Lys Lys Ser Met Leu Val Val Ser Glu Phe Ile Gly Cys
    370                 375                 380
```

Ser Pro Ser Leu Ser Gly Ala Val Arg Val Asn Pro Trp Asn Ile Glu
385                 390                 395                 400

Ala Val Ala Asp Ala Met Glu Ser Ala Leu Val Leu Pro Glu Lys Glu
            405                 410                 415

Lys Arg Met Arg His Asp Lys His Tyr Arg Tyr Val Asp Thr His Asp
        420                 425                 430

Val Gly Tyr Trp Ala Thr Ser Phe Leu Gln Asp Leu Glu Arg Thr Cys
    435                 440                 445

Lys Asp His Ala Gln Arg Arg Cys Trp Gly Ile Gly Phe Gly Leu Arg
450                 455                 460

Phe Arg Val Val Ser Leu Asp Leu Ser Phe Arg Lys Leu Ala Met Glu
465                 470                 475                 480

His Ile Val Met Ala Tyr Arg Arg Ala Lys Thr Arg Ala Ile Leu Leu
            485                 490                 495

Asp Tyr Asp Gly Thr Leu Met Pro Gln Ala Ile Asn Lys Ser Pro Ser
            500                 505                 510

Ala Asn Ser Val Glu Thr Leu Thr Ser Leu Cys Arg Asp Lys Ser Asn
        515                 520                 525

Lys Val Phe Leu Cys Ser Gly Phe Glu Lys Gly Thr Leu His Asp Trp
530                 535                 540

Phe Pro Cys Glu Asn Leu Gly Leu Ala Ala Glu His Gly Tyr Phe Leu
545                 550                 555                 560

Arg Ser Ser Arg Asp Ala Glu Trp Glu Ile Ser Ile Pro Pro Ala Asp
            565                 570                 575

Cys Ser Trp Lys Gln Ile Ala Glu Pro Val Met Cys Leu Tyr Arg Glu
            580                 585                 590

Thr Thr Asp Gly Ser Ile Ile Glu Asn Arg Glu Thr Val Leu Val Trp
            595                 600                 605

Asn Tyr Glu Asp Ala Asp Pro Asp Phe Gly Ser Cys Gln Ala Lys Glu
610                 615                 620

Leu Val Asp His Leu Glu Ser Val Leu Ala Asn Glu Pro Val Ser Val
625                 630                 635                 640

Lys Ser Thr Gly His Ser Val Glu Val Lys Pro Gln Gly Val Ser Lys
            645                 650                 655

Gly Leu Val Ala Arg Arg Leu Leu Ala Ser Met Gln Glu Arg Gly Met
            660                 665                 670

Cys Thr Asp Phe Val Leu Cys Ile Gly Asp Asp Arg Ser Asp Glu Glu
            675                 680                 685

Met Phe Gln Met Ile Thr Ser Ser Thr Cys Gly Glu Ser Leu Ala Ala
            690                 695                 700

Thr Ala Glu Val Phe Ala Cys Thr Val Gly Arg Lys Pro Ser Lys Ala
705                 710                 715                 720

Lys Tyr Tyr Leu Asp Asp Thr Ala Glu Val Val Arg Leu Met Gln Gly
            725                 730                 735

Leu Ala Ser Val Ser Asn Glu Leu Ala Arg Ala Ala Ser Pro Pro Glu
            740                 745                 750

Asp Asp Asp Glu
        755

<210> SEQ ID NO 68
<211> LENGTH: 854
<212> TYPE: PRT
<213> ORGANISM: Vitis vinifera

<400> SEQUENCE: 68

```
Met Val Ser Arg Ser Tyr Ser Asn Leu Leu Glu Leu Ala Ser Gly Glu
1               5                   10                  15

Ser Pro Ser Phe Gly Arg Met Ser Arg Arg Ile Pro Arg Ile Met Thr
            20                  25                  30

Val Ala Gly Ile Ile Ser Asp Leu Asp Asp Pro Ser Glu Ser Val
        35                  40                  45

Cys Ser Asp Pro Ser Ser Ser Val Gln Arg Asp Arg Leu Ile Ile
    50                  55                  60

Val Ala Asn Gln Leu Pro Ile Arg Ala Gln Arg Lys Ser Glu Asn Asn
65                  70                  75                  80

Asn Gly Trp Ile Phe Ser Trp Asp Glu Asn Ser Leu Leu Gln Leu
                85                  90                  95

Lys Asp Gly Leu Gly Asp Asp Glu Ile Glu Val Ile Tyr Val Gly Cys
            100                 105                 110

Leu Lys Glu Glu Ile His Pro Cys Glu Gln Asp Glu Val Ser Gln Ile
        115                 120                 125

Leu Leu Glu Thr Phe Lys Cys Val Pro Thr Phe Leu Pro Pro Asp Leu
    130                 135                 140

Phe Thr Arg Tyr Tyr His Gly Phe Cys Lys Gln Gln Leu Trp Pro Leu
145                 150                 155                 160

Phe His Tyr Met Leu Pro Leu Ser Pro Asp Leu Gly Gly Arg Phe Asn
                165                 170                 175

Arg Ser Leu Trp Gln Ala Tyr Val Ser Val Asn Lys Ile Phe Ala Asp
            180                 185                 190

Arg Ile Met Glu Val Ile Asn Pro Glu Asp Asp Phe Val Trp Ile His
        195                 200                 205

Asp Tyr His Leu Met Val Leu Pro Thr Phe Leu Arg Lys Arg Phe Asn
    210                 215                 220

Arg Val Lys Leu Gly Phe Phe Leu His Ser Pro Phe Pro Ser Ser Glu
225                 230                 235                 240

Ile Tyr Arg Thr Leu Pro Ile Arg Glu Glu Leu Leu Arg Ala Leu Leu
                245                 250                 255

Asn Ser Asp Leu Ile Gly Phe His Thr Phe Asp Tyr Ala Arg His Phe
            260                 265                 270

Leu Ser Cys Cys Ser Arg Met Leu Gly Leu Ser Tyr Glu Ser Lys Arg
        275                 280                 285

Gly Tyr Ile Gly Leu Glu Tyr Tyr Gly Arg Thr Val Ser Ile Lys Ile
    290                 295                 300

Leu Pro Val Gly Ile His Met Gly Gln Leu Gln Ser Val Leu Ser Leu
305                 310                 315                 320

Pro Glu Thr Glu Glu Lys Val Ala Glu Leu Ile Lys Gln Phe Cys Asp
                325                 330                 335

Gln Asp Arg Ile Met Leu Leu Gly Val Asp Asp Met Asp Ile Phe Lys
            340                 345                 350

Gly Ile Ser Leu Lys Leu Leu Ala Met Glu Gln Leu Leu Val Gln His
        355                 360                 365

Pro Glu Trp Gln Gly Lys Val Val Leu Val Gln Ile Ala Asn Pro Ala
    370                 375                 380

Arg Gly Arg Gly Lys Asp Val Lys Glu Val Gln Thr Glu Thr Phe Ser
385                 390                 395                 400

Thr Val Lys Arg Ile Asn Glu Thr Phe Gly Lys Pro Gly Tyr Asp Pro
                405                 410                 415
```

```
Val Val Leu Ile Asp Glu Pro Leu Lys Phe Tyr Glu Arg Ile Ala Tyr
            420                 425                 430

Tyr Val Ala Glu Cys Cys Leu Val Thr Ala Val Arg Asp Gly Met
        435                 440                 445

Asn Leu Ile Pro Tyr Glu Tyr Ile Ile Ser Arg Gln Gly Asn Glu Lys
        450                 455                 460

Leu Asp Lys Val Leu Gly Leu Glu Ser Ser Ile Pro Lys Lys Ser Met
465                 470                 475                 480

Leu Val Val Ser Glu Phe Ile Gly Cys Ser Pro Ser Leu Ser Gly Ala
                485                 490                 495

Ile Arg Val Asn Pro Trp Asn Ile Asp Ala Val Ala Asp Ala Met Asp
                500                 505                 510

Ser Ala Leu Glu Met Leu Glu Pro Glu Lys Gln Leu Arg His Glu Lys
            515                 520                 525

His Tyr Arg Tyr Val Ser Thr His Asp Val Gly Tyr Trp Ala Arg Ser
            530                 535                 540

Phe Leu Gln Asp Leu Glu Arg Thr Cys Arg Asp His Val Arg Arg Arg
545                 550                 555                 560

Cys Trp Gly Ile Gly Phe Gly Leu Ser Phe Arg Val Val Ala Leu Asp
                565                 570                 575

Pro Asn Phe Arg Lys Leu Ser Met Glu His Ile Val Ser Ala Tyr Lys
                580                 585                 590

Arg Thr Thr Thr Arg Ala Ile Leu Leu Asp Tyr Asp Gly Thr Leu Met
            595                 600                 605

Pro Gln Ala Ser Ile Asp Lys Gly Pro Thr Pro Lys Ser Ile Glu Met
610                 615                 620

Leu Lys Thr Leu Cys Arg Asp Glu Asn Asn Met Val Leu Ile Val Ser
625                 630                 635                 640

Ala Arg Ser Arg Lys Lys Leu Glu Asp Trp Phe Ser Pro Cys Glu Asn
                645                 650                 655

Leu Gly Ile Ala Ala Glu His Gly Tyr Phe Leu Arg Pro Lys Gly Asp
                660                 665                 670

Val Glu Trp Glu Thr Cys Val Pro Val Ala Asp Cys Ser Trp Lys Gln
            675                 680                 685

Ile Ala Glu Pro Val Met Lys Leu Tyr Thr Glu Thr Thr Asp Gly Ser
            690                 695                 700

Thr Ile Glu Asp Lys Glu Thr Ala Leu Ala Trp Cys Tyr Glu Asp Ala
705                 710                 715                 720

Asp Pro Asp Phe Gly Ser Cys Gln Ala Lys Glu Leu Leu Asp His Leu
                725                 730                 735

Glu Ser Val Leu Ala Asn Glu Pro Val Thr Val Lys Ser Gly Gln Ser
            740                 745                 750

Leu Val Glu Val Lys Pro Gln Gly Val Ser Lys Gly Ile Val Ala Lys
            755                 760                 765

Arg Leu Leu Ser Thr Met Gln Glu Arg Gly Met Leu Pro Asp Phe Val
            770                 775                 780

Leu Cys Ile Gly Asp Asp Arg Ser Asp Glu Asp Met Phe Glu Ala Ile
785                 790                 795                 800

Thr Ser Ser Met Ala Gly Ser Ser Ile Ala Pro Arg Ala Glu Val Phe
                805                 810                 815

Ala Cys Thr Val Gly Arg Lys Pro Ser Lys Ala Lys Tyr Tyr Leu Asp
                820                 825                 830
```

```
Asp Thr Gly Glu Ile Val Arg Leu Met Gln Gly Leu Ala Ser Val Ser
            835                 840                 845

Glu Gln Pro Val Pro Leu
    850

<210> SEQ ID NO 69
<211> LENGTH: 854
<212> TYPE: PRT
<213> ORGANISM: Populus balsamifera subsp. trichocarpa

<400> SEQUENCE: 69

Met Val Ser Arg Ser Tyr Ser Asn Leu Leu Glu Leu Ala Ser Gly Glu
1               5                   10                  15

Ser Pro Ser Phe Gly Arg Met Ser Arg Arg Ile Pro Arg Ile Met Thr
            20                  25                  30

Val Ala Gly Ile Met Ser Asp Ile Asp Asp Pro Ser Glu Ser Val
        35                  40                  45

Cys Ser Asp Pro Ser Ser Ser Thr Pro Lys Asp Arg Ile Ile Ile
    50                  55                  60

Val Ala Asn Gln Leu Pro Ile Arg Ala Gln Arg Lys Ser Asp Gly Ser
65                  70                  75                  80

Lys Ser Trp Ile Phe Ser Trp Asp Glu Asn Ser Leu Leu Leu Gln Leu
                85                  90                  95

Lys Asp Gly Leu Gly Asp Asp Glu Ile Glu Val Ile Tyr Val Gly Cys
            100                 105                 110

Leu Lys Glu Glu Val His Pro Asn Glu Gln Asp Glu Val Ser Gln Ile
        115                 120                 125

Leu Leu Glu Thr Phe Lys Cys Val Pro Thr Phe Leu Pro Pro Asp Leu
    130                 135                 140

Phe Ser Arg Tyr Tyr His Gly Phe Cys Lys Gln Leu Trp Pro Leu
145                 150                 155                 160

Phe His Tyr Met Leu Pro Leu Ser Pro Asp Leu Gly Gly Arg Phe Asn
                165                 170                 175

Arg Ser Leu Trp Gln Ala Tyr Val Ser Val Asn Lys Ile Phe Ala Asp
            180                 185                 190

Arg Ile Met Glu Val Ile Asn Pro Glu Asp Asp Phe Val Trp Val His
        195                 200                 205

Asp Tyr His Leu Met Ala Leu Pro Thr Phe Leu Arg Lys Arg Phe Asn
    210                 215                 220

Lys Val Lys Leu Gly Phe Phe Leu His Ser Pro Phe Pro Ser Ser Glu
225                 230                 235                 240

Ile Tyr Lys Thr Leu Pro Ile Arg Glu Glu Leu Leu Arg Ala Leu Leu
                245                 250                 255

Asn Ser Asp Leu Ile Gly Phe His Thr Phe Asp Tyr Ala Arg His Phe
            260                 265                 270

Leu Ser Cys Cys Ser Arg Met Leu Gly Leu Ser Tyr Glu Ser Lys Arg
        275                 280                 285

Gly Tyr Ile Gly Ile Glu Tyr Cys Gly Arg Thr Val Ser Ile Lys Ile
    290                 295                 300

Leu Pro Val Gly Ile His Met Gly Gln Leu Gln Ser Val Leu Ser Leu
305                 310                 315                 320

Pro Glu Thr Glu Ala Lys Val Lys Glu Leu Ile Lys Gln Phe Ser Asp
                325                 330                 335

Gln Asp Arg Ile Met Leu Leu Gly Val Asp Asp Met Asp Ile Phe Lys
            340                 345                 350
```

```
Gly Ile Ser Leu Lys Leu Leu Ala Met Glu Gln Leu Met Gln His
        355                 360                 365

Pro Glu Trp Gln Gly Lys Ile Val Leu Val Gln Ile Ala Asn Pro Ala
    370                 375                 380

Arg Gly Lys Gly Lys Asp Val Lys Glu Val Gln Ala Glu Thr His Ala
385                 390                 395                 400

Ala Val Lys Arg Ile Asn Glu Thr Phe Gly Lys Pro Gly Tyr Asp Pro
                405                 410                 415

Ile Val Leu Ile Asp Ala Pro Leu Lys Phe Tyr Glu Lys Val Ala Tyr
                420                 425                 430

Tyr Val Val Ala Glu Cys Cys Leu Val Thr Ala Val Arg Asp Gly Met
            435                 440                 445

Asn Leu Ile Pro Tyr Glu Tyr Ile Ile Ser Arg Gln Gly Asn Asp Arg
    450                 455                 460

Leu Asn Lys Leu Leu Gly Gln Glu Pro Ser Thr Pro Lys Lys Ser Met
465                 470                 475                 480

Leu Val Ile Ser Glu Phe Ile Gly Cys Ser Pro Ser Leu Ser Gly Ala
                485                 490                 495

Ile Arg Val Asn Pro Trp Asn Ile Asp Ala Val Ala Asp Ala Met Asp
                500                 505                 510

Phe Ala Leu Glu Met Ala Glu Pro Glu Lys Gln Leu Arg His Glu Lys
            515                 520                 525

His Tyr Arg Tyr Val Ser Thr His Asp Val Gly Tyr Trp Ala Arg Ser
    530                 535                 540

Phe Leu Gln Asp Leu Glu Arg Thr Cys Arg Asp His Ser Arg Arg Arg
545                 550                 555                 560

Cys Trp Gly Ile Gly Phe Gly Leu Ser Phe Arg Val Val Ala Leu Asp
                565                 570                 575

Pro Asn Phe Lys Lys Leu Ser Met Glu Arg Ile Val Ser Ala Tyr Lys
                580                 585                 590

Arg Thr Thr Thr Arg Ala Ile Leu Leu Asp Tyr Asp Gly Thr Leu Met
            595                 600                 605

Pro Gln Ala Ser Ile Asp Lys Ser Pro Ser Ser Lys Ser Ile Asp Ile
    610                 615                 620

Ile Asn Asn Leu Cys Arg Asp Lys Asn Asn Met Val Phe Leu Val Ser
625                 630                 635                 640

Ala Arg Ser Arg Asn Thr Val Ala Glu Trp Phe Ser Glu Cys Glu Lys
                645                 650                 655

Leu Gly Leu Ala Ala Glu His Gly Tyr Phe Leu Arg Leu Lys Arg Asp
                660                 665                 670

Ala Glu Trp Glu Thr Arg Val Pro Val Ala Asp Thr Thr Trp Lys Gln
            675                 680                 685

Ile Ala Glu Pro Val Met Gln Leu Tyr Thr Glu Thr Thr Asp Gly Ser
    690                 695                 700

Thr Ile Glu Asp Lys Glu Thr Ser Leu Val Trp Cys Tyr Glu Asp Ala
705                 710                 715                 720

Asp Pro Asp Phe Gly Ser Cys Gln Ala Lys Glu Leu Leu Asp His Leu
                725                 730                 735

Glu Ser Val Leu Ala Asn Glu Pro Val Thr Val Lys Ser Gly Gln Asn
                740                 745                 750

Ile Val Glu Val Lys Pro Gln Gly Val Ser Lys Gly Leu Val Ala Lys
            755                 760                 765
```

```
Arg Leu Leu Ser Ile Met Gln Glu Asn Glu Met Ser Pro Asp Phe Val
        770                 775                 780

Leu Cys Ile Gly Asp Asp Arg Ser Asp Glu Asp Met Phe Glu Val Ile
785                 790                 795                 800

Thr Thr Ser Met Ala Gly Pro Ser Ile Ala Glu Asn Ala Glu Val Phe
                805                 810                 815

Ala Cys Thr Val Gly Arg Lys Pro Ser Lys Ala Lys Tyr Tyr Leu Asp
                820                 825                 830

Asp Thr Ala Glu Ile Val Arg Leu Met Gln Gly Leu Ala Ser Val Ser
            835                 840                 845

Glu Gln Thr Val Thr Val
    850

<210> SEQ ID NO 70
<211> LENGTH: 21
<212> TYPE: DNA
<213> ORGANISM: Arabidopsis thaliana

<400> SEQUENCE: 70
tgatcgttct ttatggcaag c                                           21

<210> SEQ ID NO 71
<211> LENGTH: 21
<212> TYPE: DNA
<213> ORGANISM: Arabidopsis thaliana

<400> SEQUENCE: 71
gcatttgctt ctctgcttct g                                           21

<210> SEQ ID NO 72
<211> LENGTH: 21
<212> TYPE: DNA
<213> ORGANISM: Arabidopsis thaliana

<400> SEQUENCE: 72
tgtcaccaaa caacactcag c                                           21

<210> SEQ ID NO 73
<211> LENGTH: 21
<212> TYPE: DNA
<213> ORGANISM: Arabidopsis thaliana

<400> SEQUENCE: 73
tacgagctca gagaagggtt g                                           21

<210> SEQ ID NO 74
<211> LENGTH: 21
<212> TYPE: DNA
<213> ORGANISM: Arabidopsis thaliana

<400> SEQUENCE: 74
ttcgtgatag ccactaccgt c                                           21

<210> SEQ ID NO 75
<211> LENGTH: 21
<212> TYPE: DNA
<213> ORGANISM: Arabidopsis thaliana

<400> SEQUENCE: 75
acagagtgga ggtcaatggt g                                           21
```

-continued

```
<210> SEQ ID NO 76
<211> LENGTH: 20
<212> TYPE: DNA
<213> ORGANISM: Arabidopsis thaliana

<400> SEQUENCE: 76
cacacatttg attatgcacg                                               20

<210> SEQ ID NO 77
<211> LENGTH: 21
<212> TYPE: DNA
<213> ORGANISM: Arabidopsis thaliana

<400> SEQUENCE: 77
gagactccca tcctcttcca c                                             21

<210> SEQ ID NO 78
<211> LENGTH: 21
<212> TYPE: DNA
<213> ORGANISM: Arabidopsis thaliana

<400> SEQUENCE: 78
ttgctctctt gctcgatctt c                                             21

<210> SEQ ID NO 79
<211> LENGTH: 21
<212> TYPE: DNA
<213> ORGANISM: Arabidopsis thaliana

<400> SEQUENCE: 79
tgtcatgctg ctgtagaatg c                                             21

<210> SEQ ID NO 80
<211> LENGTH: 21
<212> TYPE: DNA
<213> ORGANISM: Arabidopsis thaliana

<400> SEQUENCE: 80
gacgtgtgcc acaaattatc c                                             21

<210> SEQ ID NO 81
<211> LENGTH: 21
<212> TYPE: DNA
<213> ORGANISM: Arabidopsis thaliana

<400> SEQUENCE: 81
gtcgtgtacg ctctccaatt c                                             21
```